(12) United States Patent
Fedeles et al.

(10) Patent No.: US 9,982,009 B2
(45) Date of Patent: May 29, 2018

(54) METHODS FOR TREATING POLYCYSTIC KIDNEY DISEASE AND POLYCYSTIC LIVER DISEASE

(71) Applicants: Massachusetts Institute of Technology, Cambridge, MA (US); Yale University, New Haven, CT (US)

(72) Inventors: Bogdan I. Fedeles, Cambridge, MA (US); Sorin V. Fedeles, Hamden, CT (US); Robert G. Croy, Belmont, MA (US); Stefan Somlo, Westport, CT (US); John M. Essigmann, Cambridge, MA (US)

(73) Assignees: Massachusetts Institute of Technology, Cambridge, MA (US); Yale University, New Haven, CT (US)

( * ) Notice: Subject to any disclaimer, the term of this patent is extended or adjusted under 35 U.S.C. 154(b) by 0 days. days.

(21) Appl. No.: 14/515,441

(22) Filed: Oct. 15, 2014

(65) Prior Publication Data
US 2015/0105361 A1 Apr. 16, 2015

Related U.S. Application Data

(60) Provisional application No. 61/891,377, filed on Oct. 15, 2013.

(51) Int. Cl.
| | |
|---|---|
| A61K 31/56 | (2006.01) |
| C07J 41/00 | (2006.01) |
| A61K 31/122 | (2006.01) |
| A61K 31/567 | (2006.01) |

(52) U.S. Cl.
CPC ......... *C07J 41/0077* (2013.01); *A61K 31/122* (2013.01); *A61K 31/567* (2013.01)

(58) Field of Classification Search
CPC . A61K 31/122; A61K 31/567; C07J 41/0077; C12N 2501/48; C12N 5/0686
See application file for complete search history.

(56) References Cited

U.S. PATENT DOCUMENTS

| | | | |
|---|---|---|---|
| 3,502,699 A | 3/1970 | Hughes et al. | |
| 2006/0019936 A1* | 1/2006 | Eissigmann | A61K 31/573 514/179 |

OTHER PUBLICATIONS

Wahl et al, Nephrol Dial Transplant (2006) 21: 598-604.*
Patani et al, Chem. Rev. 1996, 96, 3147-3176.*
Fedeles et al, Nature Genetics 2001, 43(7):639-648.*
J. G. Cannon Chapter Nineteen in Burger's Medicinal Chemistry and Drug Discovery, Fifth Edition, vol. I: Principles and Practice, Wiley-Inter-science 1995, pp. 783-802, 784.*
International Search Report and Written Opinion dated Apr. 1, 2015 for Application No. PCT/US2014/060774.
Distefano et al., Polycystin-1 regulates extracellular signal-regulated kinase-dependent phosphorylation of tuberin to control cell size through mTOR and its downstream effectors S6K and 4EBP1. Mol Cell Biol. May 2009;29(9):2359-71. doi: 10.1128/MCB.01259-08. Epub Mar. 2, 2009.
Kaser et al., XBP1 links ER stress to intestinal inflammation and confers genetic risk for human inflammatory bowel disease. Cell. Sep. 5, 2008;134(5):743-56. doi: 10.1016/j.cell.2008.07.021.
Shillingford et al., The mTOR pathway is regulated by polycystin-1, and its inhibition reverses renal cystogenesis in polycystic kidney disease. Proc Natl Acad Sci U S A. Apr. 4, 2006;103(14):5466-71. Epub Mar. 27, 2006.
Tao et al., Rapamycin markedly slows disease progression in a rat model of polycystic kidney disease. J Am Soc Nephrol. Jan. 2005;16(1):46-51. Epub Nov. 24, 2004.
Wahl et al., Inhibition of mTOR with sirolimus slows disease progression in Han:SPRD rats with autosomal dominant polycystic kidney disease (ADPKD). Nephrol Dial Transplant. Mar. 2006;21(3):598-604. Epub Oct. 12, 2005.
Zhang et al., The unfolded protein response: a stress signaling pathway critical for health and disease. Neurology. Jan. 24, 2006;66(2 Suppl 1):S102-9.
Ma et al., Loss of cilia suppresses cyst growth in genetic models of autosomal dominant polycystic kidney disease. Nat Genet. Sep. 2013;45(9):1004-12. doi: 10.1038/ng.2715. Epub Jul. 28, 2013.
Novalic et al., Dose-dependent effects of sirolimus on mTOR signaling and polycystic kidney disease. J Am Soc Nephrol. May 2012;23(5):842-53. doi:10.1681/ASN.2011040340. Epub Feb. 16, 2012.
Ruggenenti et al., Effect of Sirolimus on Disease Progression in Patients with Autosomal Dominant Polycystic Kidney Disease and CKD Stages 3b-4. Clin J Am Soc Nephrol. May 6, 2016;11(5):785-94. doi:10.2215/CJN.09900915. Epub Feb. 22, 2016.

(Continued)

*Primary Examiner* — Jean P Cornet
(74) *Attorney, Agent, or Firm* — Wolf, Greenfield & Sacks, P.C.

(57) ABSTRACT

The present invention provides compounds of Formula (I) or (II), which are thought to be able to inhibit mTOR (mammalian target of rapamycin) signaling pathway, induce UPR (unfolded protein response), and/or perturb mitochondrial function of a cyst cell (e.g., a cyst cell causing polycystic kidney disease (PKD, e.g., autosomal dominant PKD (AD-PKD) or autosomal recessive PKD (ARPKD)) or polycystic liver disease (PLD, e.g., autosomal dominant PLD (AD-PLD) or autosomal recessive PLD (ARPLD)). The invention also provides pharmaceutical compositions, kits, and methods involving the compounds described herein for use in treating PKD or PLD, inhibiting the growth of a cyst cell, and/or killing a cyst cell.

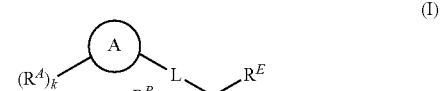

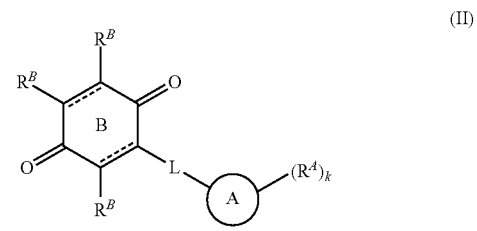

6 Claims, 11 Drawing Sheets

(56) References Cited

OTHER PUBLICATIONS

Serra et al., Sirolimus and kidney growth in autosomal dominant polycystic kidney disease. N Engl J Med. Aug. 26, 2010;363(9):820-9. doi: 10.1056/NEJMoa0907419. Epub Jun. 26, 2010.

Shillingford et al., Folate-conjugated rapamycin slows progression of polycystic kidney disease. J Am Soc Nephrol. Oct. 2012;23(10):1674-81. Epub Aug. 2, 2012.

Shillingford et al., Rapamycin ameliorates PKD resulting from conditional inactivation of Pkd1. J Am Soc Nephrol. Mar. 2010;21(3):489-97. doi: 10.1681/ASN.2009040421. Epub Jan. 14, 2010.

Walz et al., Everolimus in patients with autosomal dominant polycystic kidney disease. N Engl J Med. Aug. 26, 2010;363(9):830-40. doi:10.1056/NEJMoa1003491. Epub Jun. 26, 2010. Erratum in: N Engl J Med. Sep. 16, 2010;363(12):1190. N Engl J Med. Nov. 11, 2010;363(20):1977.

Watnick et al., mTOR inhibitors in polycystic kidney disease. N Engl J Med. Aug. 26, 2010;363(9):879-81. doi: 10.1056/NEJMe1006925. Epub Jun. 26, 2010.

Fingar et al., Target of rapamycin (TOR): an integrator of nutrient and growth factor signals and coordinator of cell growth and cell cycle progression. Oncogene. Apr. 19, 2004;23(18):3151-71.

Reiling et al., Stress and mTORture signaling. Oncogene. Oct. 16, 2006;25(48):6373-83.

Chembank Accession No. 1177150-34-3. Aug. 28, 2009.

Cheung et al., Further acidic constituents and neutral components of pinus massoniana Resin. Tetrahedron. Sep. 1993;49(36):7903-7915.

Peces et al., Nephrotic syndrome and idiopathic membranous nephropathy associated with autosomal-dominant polycystic kidney disease. Scientific World Journal. May 5, 2011;11:1041-7. doi: 10.1100/tsw.2011.94.

Singh et al., Rational design of novel antiandrogens for neutralizing androgen receptor function in hormone refractory prostate cancer. Prostate. Oct. 1, 2008;68(14):1570-81. doi: 10.1002/pros.20821.

Fedeles et al., Chemical genetics analysis of an aniline mustard anticancer agent reveals complex I of the electron transport chain as a target. J Biol Chem. Sep. 30, 2011;286(39):33910-20. doi: 10.1074/jbc.M111.278390. Epub Aug. 10, 2011.

Marquis et al., Disruption of gene expression and induction of apoptosis in prostate cancer cells by a DNA-damaging agent tethered to an androgen receptor ligand. Chem Biol. Jul. 2005 ; 12(7):779-87.

Ozcan et al., Loss of the tuberous sclerosis complex tumor suppressors triggers the unfolded protein response to regulate insulin signaling and apoptosis. Mol Cell. Mar. 14, 2008;29(5):541-51. doi: 10.1016/j.molcel.2007.12.023.

Wilson, Molecular mechanisms of polycystic kidney disease. Biochim Biophys Acta. Oct. 2011;1812(10):1201. doi: 10.1016/j.bbadis.2011.08.004.

\* cited by examiner

Compound I-1        thapsigargin (Tg)

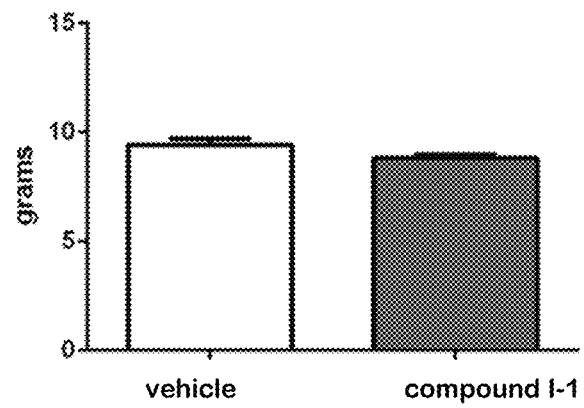
FIG. 3B Body Weight
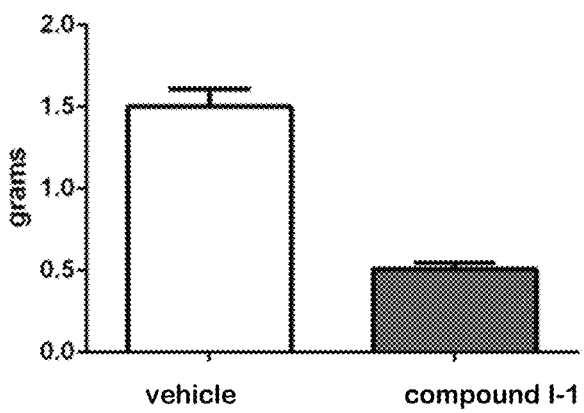
FIG. 3C Kidney Weight
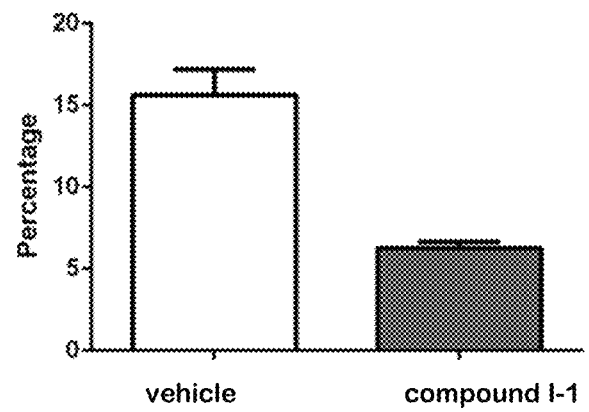
FIG. 3D Kidney/Body Weight Ratio

*P24;Pkd1<sup>fl/fl</sup>;Pkhd1Cre*

FIG. 6A  Pkd1fl/fl;Pax8rtta;tet-OCre

Vehicle     11beta

Vehicle | Compound I-3

METHODS FOR TREATING POLYCYSTIC KIDNEY DISEASE AND POLYCYSTIC LIVER DISEASE

RELATED APPLICATIONS

The present application claims priority under 35 U.S.C. § 119(e) to U.S. provisional patent application, U.S. Ser. No. 61/891,377, filed Oct. 15, 2013, which is incorporated herein by reference.

GOVERNMENT SUPPORT

This invention was made with government support under Grant Nos. DK079310, CA07743, and DK007276 awarded by the National Institutes of Health and under Contract No. W81XWH-06-0183 awarded by the Army Medical Research and Material Command. The government has certain rights in the invention.

BACKGROUND OF THE INVENTION

Polycystic kidney disease (PKD) is a genetic disorder characterized by the growth of numerous cysts in the kidneys of a subject. PKD is among the most common life-threatening genetic diseases in the world and is a leading cause of end-stage renal failure and a common indication for dialysis or renal transplantation (Wilson, *N. Engl. J. Med.* 2004, 350, 151-164). The kidneys filter wastes and extra fluid from the blood to form urine and also regulate amounts of certain vital substances in the subject. When cysts form in the kidneys, they are filled with fluid. PKD cysts can profoundly enlarge the kidneys while replacing much of the normal structure, resulting in reduced kidney function and leading to kidney failure. PKS includes autosomal dominant PKD (ADPKD) and autosomal recessive PKD (ARPKD). ADPKD is the more common inherited form of PKD, whereas ARPKD is a rare inherited form. It has been reported that mutations in two genes, PKD1 and PKD2, which encode polycystin-1 (PC1) and polycystin-2 (PC2), respectively, may be responsible for ADPKD (Gallagher et al., *Adv. Chronic Kidney Dis.* 2010, 17(2): 118-130; The European Polycystic Kidney Disease Consortium, *Cell* 1994, 78:725; The International Polycystic Kidney Disease Consortium, *Cell* 1995, 81:289-298; Mochizuki et al., *Science* 1996, 272:1339-1342; The European Polycystic Kidney Disease Consortium, *Cell* 1994, 77, 881-894). A causative gene ARPKD has been thought to be PKHD1, which encodes fibrocystin/polyductin (FPC).

PKD can also cause cysts in the liver and problems in other organs, such as blood vessels in the brain and heart. For example, polycystic liver disease (PLD) is an inherited condition characterized by the presence of multiple scattered cysts of biliary origin throughout the liver parenchyma (Fedeles et al., *Nature Genetics* 2011, 43(7):639-648; Qian et al., *Hepatology* 2003, 37, 164-171). PLD occurs frequently as an extra-renal manifestation of ADPKD, but it also exists as a distinct dominantly inherited genetic entity without kidney cysts (autosomal dominant PLD (ADPLD)). Mutations in PRKCSH or SEC63 may underlie isolated ADPLD (Reynolds et al., *Am. J. Hum. Genet.* 2000, 67, 1598-1604; Li et al., *Am. J. Hum. Genet.* 2003, 72, 691-703; Davila et al., *Nat. Genet.* 2004, 36, 575-577; Drenth et al., *Nat. Genet.* 2003, 33, 345-347).

PC1, PC2, and FPC, along with one Meckel syndrome gene product (MKS3) (Smith et al., *Nat. Genet.* 2006, 38, 191-196), have been reported to be the only integral membrane proteins mutated in cilia-associated fibrocystic diseases (Sharma et al., *Curr. Top. Dev. Biol.* 2008, 85, 371-427). ADPKD and ADPLD are also unique in that they may be the only dominantly inherited traits among the cilia-associated diseases (Menezes et al., *Methods Cell Biol.* 2009, 94, 273-297).

Subjects with PKD (e.g., ADPKD) may be treated by hemodialysis, peritoneal dialysis, or renal transplantation. Treatment of PLD (e.g., ADPLD) may include cyst aspiration, cyst fenestration, liver resection, and liver transplantation. Currently, there are no FDA-approved therapeutic drugs that directly target PKD. Several clinical trials are underway testing the cAMP inhibitor (Tolvaptan) or excessive intake of water as means to slow down the progression of PKD. Certain mTOR inhibitors, such as rapamycin, have been studied in clinical trials, but those mTOR inhibitors have not shown significant clinical effectiveness. Therefore, there remains a need for improved treatment of PKD and PLD.

SUMMARY OF THE INVENTION

The present invention provides compounds of Formula (I) or (II), which are thought to be able to inhibit mTOR (mammalian target of rapamycin) signaling pathway, induce UPR (unfolded protein response), and/or perturb mitochondrial function of a cyst cell (e.g., a cyst cell causing polycystic kidney disease (PKD, e.g., autosomal dominant PKD (ADPKD) or autosomal recessive PKD (ARPKD)) or polycystic liver disease (PLD, e.g., autosomal dominant PLD (ADPLD) or autosomal recessive PLD (ARPLD)). The invention also provides pharmaceutical compositions, kits, and methods involving the compounds described herein for use in treating and/or preventing PKD or PLD, inhibiting the growth of a cyst cell, and/or killing a cyst cell.

In one aspect, the present invention provides compounds of Formula (I) or (II):

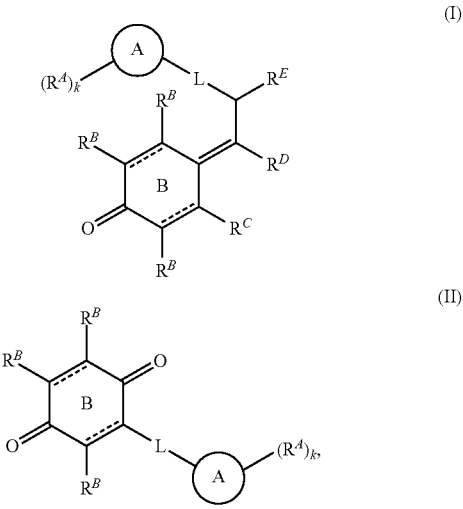

and pharmaceutically acceptable salts, hydrates, solvates, polymorphs, co-crystals, tautomers, and isotopically labeled derivatives thereof, wherein Ring A, L, $R^A$, $R^B$, $R^C$, $R^D$, $R^E$, k, and === are as described herein.

Exemplary compounds of Formula (I) include, but are not limited to:

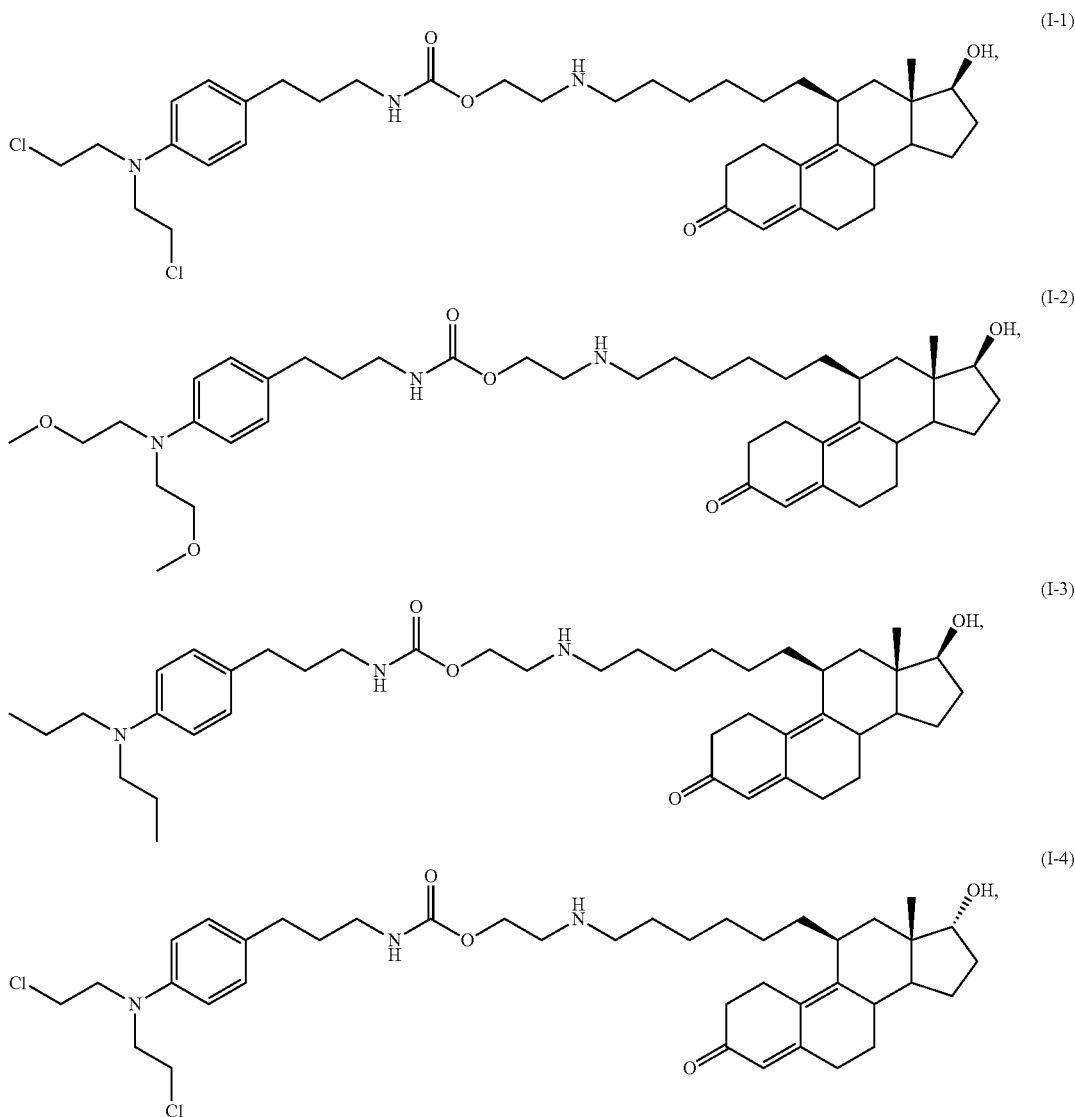

and pharmaceutically acceptable salts, hydrates, solvates, polymorphs, co-crystals, tautomers, and isotopically labeled derivatives thereof. In certain embodiments, a compound of the invention is not a compound of Formula (I-1), (I-2), or (I-3), or a pharmaceutically acceptable salt, hydrate, solvate, polymorph, co-crystal, tautomer, or isotopically labeled derivative thereof.

In another aspect, the present invention provides pharmaceutical compositions including a compound described herein, and optionally a pharmaceutically acceptable excipient. In certain embodiments, the inventive pharmaceutical compositions include a therapeutically or prophylactically effective amount of a compound described herein. The pharmaceutical composition may be useful for treating and/or preventing PKD or PLD in a subject in need thereof, inhibiting the growth of a cyst cell, and/or killing a cyst cell.

Another aspect of the present invention relates to methods of treating and/or preventing PKD (e.g., ADPKD or ARPKD) in a subject in need thereof.

In another aspect, the present invention provides methods of treating and/or preventing PLD (e.g., ADPLD or ARPLD) in a subject in need thereof.

In yet another aspect, the present invention provides methods of inhibiting the growth of a cyst cell.

In still another aspect, the present invention provides methods of killing a cyst cell.

In certain embodiments, the methods of the present invention include administering to the subject an effective amount of a compound or pharmaceutical composition described herein. In certain embodiments, the methods of the present invention include contacting the cyst cell with an effective amount of a compound or pharmaceutical composition described herein. In certain embodiments, the effective amount is a therapeutically effective amount. In certain embodiments, the effective amount is a prophylactically effective amount.

In certain embodiments, the subject is a human. In certain embodiments, the subject is a non-human mammal. In certain embodiments, the cyst cell is a cyst cell that causes PKD. In certain embodiments, the cyst cell is a cyst cell that causes PLD. In certain embodiments, the cyst cell is an in vitro cyst cell.

Another aspect of the invention relates to methods of screening a library of compounds to identify a compound that is useful in the methods of the invention (e.g., useful for treating PKD or PLD).

Another aspect of the present invention relates to kits comprising a container with a compound or pharmaceutical composition described herein. The kits of the invention may include a single dose or multiple doses of the compound or pharmaceutical composition. The provided kits may be useful in treating and/or preventing PDK or PLD in a subject in need thereof. The kits may also be useful in inhibiting the growth of a cyst cell or killing a cyst cell. In certain embodiments, the kit further includes instructions for administering to the subject or contacting the cyst cell with the compound or pharmaceutical composition.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers". When a compound has an asymmetric center, for example, a carbon atom of the compound is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates plane polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGrawHill, NY, 1962); Wilen, *Tables of Resolving Agents and Optical Resolutions* p. 268 (E.L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched" means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E.L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}$C or $^{14}$C are within the scope of this invention. Such compounds are useful, for example, as analytical tools, as probes in biological assays, or as therapeutic agents in accordance with the present invention.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=O)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "aliphatic" includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more sustitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl" denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl" refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, (=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —O(R$^{cc}$)$_2$, —P(R$^{cc}$)$_3$, —B(R$^{aa}$)$_2$, —B(OR$^{cc}$)$_2$, —BR$^{aa}$(OR$^{cc}$), C$_{1\text{-}10}$ alkyl, C$_{1\text{-}10}$ perhaloalkyl, C$_{2\text{-}10}$ alkenyl, C$_{2\text{-}10}$ alkynyl, C$_{3\text{-}10}$ carbocyclyl, 3-14 membered heterocyclyl, C$_{6\text{-}14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1\text{-}10}$ alkyl, C$_{1\text{-}10}$ perhaloalkyl, C$_{2\text{-}10}$ alkenyl, C$_{2\text{-}10}$ alkynyl, C$_{3\text{-}10}$ carbocyclyl, 3-14 membered heterocyclyl, C$_{6\text{-}14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —(=O)$_2$N(R$^{cc}$)$_2$, —P(=O)(NR$^{cc}$)$_2$, C$_{1\text{-}10}$ alkyl, C$_{1\text{-}10}$ perhaloalkyl, C$_{2\text{-}10}$ alkenyl, C$_{2\text{-}10}$ alkynyl, C$_{3\text{-}10}$ carbocyclyl, 3-14 membered heterocyclyl, C$_{6\text{-}14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1\text{-}10}$ alkyl, C$_{1\text{-}10}$ perhaloalkyl, C$_{2\text{-}10}$ alkenyl, C$_{2\text{-}10}$ alkynyl, C$_{3\text{-}10}$ carbocyclyl, 3-14 membered heterocyclyl, C$_{6\text{-}14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3$$^+$X$^-$, —N(OR$^{cc}$) R$^{ff}$, —SH, —SR$^{cc}$, —SSR$^{ee}$, —C(=O)R$^{ee}$, —CO$_2$H, —CO$_2$R$^{cc}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_1$ alkyl, C$_{1\text{-}6}$ perhaloalkyl, C$_{2\text{-}6}$ alkenyl, C$_{2\text{-}6}$ alkynyl, C$_{3\text{-}10}$ carbocyclyl, 3-10 membered heterocyclyl, C$_{6\text{-}10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1\text{-}6}$ alkyl, C$_1$ perhaloalkyl, C$_{2\text{-}6}$ alkenyl, C$_{2\text{-}6}$ alkynyl, C$_{3\text{-}10}$ carbocyclyl, C$_{6\text{-}10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1\text{-}6}$ alkyl, C$_{1\text{-}6}$ perhaloalkyl, C$_{2\text{-}6}$ alkenyl, C$_{2\text{-}6}$ alkynyl, C$_{3\text{-}10}$ carbocyclyl, 3-10 membered heterocyclyl, C$_{6\text{-}10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1\text{-}6}$ alkyl, —ON(C$_{1\text{-}6}$ alkyl)$_2$, —N(C$_{1\text{-}6}$ alkyl)$_2$, —N(C$_{1\text{-}6}$ alkyl)$_3$$^+$X$^-$, —NH(C$_{1\text{-}6}$ alkyl)$_2$$^+$X$^-$, —NH$_2$(C$_{1\text{-}6}$ alkyl)$^+$X$_3$$^-$, —NH$_3$$^+$X$^-$, —N(OC$_{1\text{-}6}$ alkyl)(C$_{1\text{-}6}$ alkyl), —N(OH)(C$_{1\text{-}6}$ alkyl), —NH(OH), —SH, —SC$_{1\text{-}6}$ alkyl, —SS(C$_{1\text{-}6}$ alkyl), —C(=O)(C$_{1\text{-}6}$ alkyl), —CO$_2$H, —CO$_2$(C$_{1\text{-}6}$ alkyl), —OC(=O)(C$_{1\text{-}6}$ alkyl), —OCO$_2$(C$_{1\text{-}6}$ alkyl), —C(=O)NH$_2$, —C(=O)N(C$_{1\text{-}6}$ alkyl)$_2$, —OC(=O)NH(C$_{1\text{-}6}$ alkyl), —NHC(=O)(C$_{1\text{-}6}$ alkyl), —N(C$_{1\text{-}6}$ alkyl)C(=O)(C$_{1\text{-}6}$ alkyl), —NHCO$_2$(C$_{1\text{-}6}$ alkyl), —NHC(=O)N(C$_{1\text{-}6}$ alkyl)$_2$, —NHC(=O)NH(C$_{1\text{-}6}$ alkyl), —NHC(=O)NH$_2$, —C(=NH)O(C$_{1\text{-}6}$ alkyl), —OC(=NH)(C$_{1\text{-}6}$ alkyl), —OC(=NH)OC$_{1\text{-}6}$ alkyl, —C(=NH)N(C$_{1\text{-}6}$ alkyl)$_2$, —C(=NH)NH(C$_{1\text{-}6}$ alkyl), —C(=NH)NH$_2$, —OC(=NH)N(C$_{1\text{-}6}$ alkyl)$_2$, —OC(NH)NH(C$_{1\text{-}6}$ alkyl), —OC(NH)NH$_2$, —NHC(NH)N(C$_{1\text{-}6}$ alkyl)$_2$, —NHC(=NH)NH$_2$, —NHSO$_2$(C$_{1\text{-}6}$ alkyl), —SO$_2$N(C$_{1\text{-}6}$ alkyl)$_2$, —SO$_2$NH(C$_{1\text{-}6}$ alkyl), —SO$_2$NH$_2$, —SO$_2$C$_{1\text{-}6}$ alkyl, —SO$_2$OC$_{1\text{-}6}$ alkyl, —OSO$_2$C$_{1\text{-}6}$ alkyl, —SOC$_{1\text{-}6}$ alkyl, —Si(C$_{1\text{-}6}$ alkyl)$_3$, —OSi(C$_{1\text{-}6}$ alkyl)$_3$ —C(=S)N(C$_{1\text{-}6}$ alkyl)$_2$, C(=S)NH(C$_{1\text{-}6}$ alkyl), C(=S)NH$_2$, —C(=O)S($C_{1-6}$ alkyl), —C(=S)S$C_{1-6}$ alkyl, SC(=S) S$C_{1-6}$ alkyl, P(=O)$_2$($C_{1-6}$ alkyl), P(=O)($C_{1-6}$ alkyl)$_2$, —OP (=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "amino" refers to a group of the formula (—NH$_2$). A "substituted amino" refers either to a monosubstituted amine (—NHR$^h$) of a disubstituted amine (—NR$^h_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the di-substituted amino group (—NR$^h_2$) form a 5- to 6-membered heterocyclic ring.

The term "alkoxy" refers to a "substituted hydroxyl" of the formula (—OR$^i$), wherein R$^i$ is an optionally substituted alkyl group as defined herein, and the oxygen moiety is directly attached to the parent molecule.

The term "alkylthioxy" refers to a "substituted thiol" of the formula (—SR$^r$), wherein R$^r$ is an optionally substituted alkyl group as defined herein, and the sulfur moiety is directly attached to the parent molecule.

The term "alkylamino" refers to a "substituted amino" of the formula (—NR$^h_2$), wherein R$^h$ is, independently, a hydrogen or an optionally substituted alkyl group as defined herein, and the nitrogen moiety is directly attached to the parent molecule.

The term "aryl" refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl" refers to an aryl substituted alkyl group, wherein the terms "aryl" and "alkyl" are defined herein, and wherein the aryl group is attached to the alkyl group, which in turn is attached to the parent molecule. Exemplary arylalkyl groups are benzyl and phenethyl.

The term "aryloxy" refers to a "substituted hydroxyl" of the formula (—OR$^i$), wherein R$^i$ is an optionally substituted aryl group as defined herein, and the oxygen moiety is directly attached to the parent molecule.

The term "arylamino," refers to a "substituted amino" of the formula (—NR$^h_2$), wherein R$^h$ is, independently, a hydrogen or an optionally substituted aryl group as defined herein, and the nitrogen moiety is directly attached to the parent molecule.

The term "arylthioxy" refers to a "substituted thiol" of the formula (—SR$^r$), wherein R$^r$ is an optionally substituted aryl group as defined herein, and the sulfur moiety is directly attached to the parent molecule.

The terms "halo" and "halogen" refer to an atom selected from fluorine (fluoro, —F), chlorine (chloro, —Cl), bromine (bromo, —Br), and iodine (iodo, —I).

The term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, the terms "heteroalkyl", "heteroalkenyl", "heteroalkynyl", and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" refers to an alkyl moiety, as defined herein, which contain one or more oxygen, sulfur, nitrogen, phosphorus, or silicon atoms, e.g., in place of carbon atoms.

The term "heteroalkenyl" refers to an alkenyl moiety, as defined herein, which contain one or more oxygen, sulfur, nitrogen, phosphorus, or silicon atoms, e.g., in place of carbon atoms.

The term "heteroalkynyl" refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—NR$^h_2$), wherein R$^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—OR$^i$), wherein R$^i$ is an optionally substituted heteroalkyl group, as defined herein, and the oxygen moiety is directly attached to the parent molecule.

The term "heteroalkylthioxy" refers to a "substituted thiol" of the formula (—SR$^r$), wherein R$^r$ is an optionally substituted heteroalkyl group, as defined herein, and the sulfur moiety is directly attached to the parent molecule.

The term "heterocyclic," "heterocycles," or "heterocyclyl" refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl" refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothi- azolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—NR$^h_2$), wherein R$^h$ is, independently, hydrogen or an optionally substituted heteroaryl group, as defined herein, and the nitrogen moiety is directly attached to the parent molecule.

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "heteroarylthioxy" refers to a "substituted thiol" of the formula (—SR$^r$), wherein R$^r$ is an optionally substituted heteroaryl group, as defined herein, and the sulfur moiety is directly attached to the parent molecule.

The term "hydroxy" or "hydroxyl" refers to a group of the formula (—OH). A "substituted hydroxyl" refers to a group of the formula (—OR$^i$), wherein R$^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino" refers to a group of the formula (=NR$^r$), wherein R$^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein R$^r$ is hydrogen.

The term "nitro" refers to a group of the formula (—NO$_2$).

The term "oxo" refers to a group of the formula (=O).

A "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain C$^A$H(C$^B$H$_2$C$^C$H$_3$)— includes only one carbon unit C$^A$. The term "C$_R$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

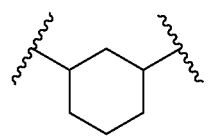 [SMILES: *C1CCCC(*)C1]

is a C$_3$ hydrocarbon chain. When a range of values is used, e.g., a C$_{1-6}$ hydrocarbon chain, the meaning of the range is as described herein. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH(CH$_2$)$_2$—, —CH$_2$—C≡C—CH$_2$—, and —C≡C—CH=CH are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

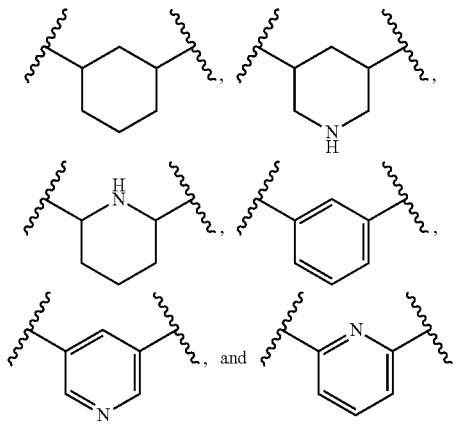

are all examples of a hydrocarbon chain. In contrast, in certain embodiments

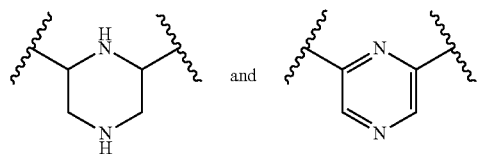 [SMILES: *C1CNCC(*)N1 ; *c1cncc(*)n1]

are not within the scope of the hydrocarbon chains described herein.

A "protecting group" is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference. Suitable "amino-protecting groups" (also referred to as "nitrogen protecting groups") include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyborl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), O-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "hydroxyl protecting group" (also referred to as an "oxygen protecting group") is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxcyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(mmethoxyphenyl)phenylmethyl, tri(mmethoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., Ca(OH)$_2$), magnesium (by using, e.g., Mg(OH)$_2$ and magnesium acetate), zinc, (by using, e.g., Zn(OH)$_2$ and zinc acetate), and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids (e.g., 1-glycine and 1-arginine) and amino acids which may be zwitterionic at neutral pH (e.g., betaine (N,N,N-trimethylglycine)) are also contemplated.

The term "tautomer" refers to a particular isomer of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, lactam-lactim forms, ketene-ynol forms, enamine-enamine forms, and pyridione-hydroxypyridine forms.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "electron withdrawing group" refers to an atom or group capable of withdrawing electrons away (in other words, decreasing the electron density) from another atom or group to which the atom or group is attached. Electron withdrawing groups may be electron withdrawing either by the inductive effect or the mesomeric effect. In one embodiment, the electron withdrawing group is electron withdrawing via the inductive effect. In another embodiment, the electron withdrawing group is electron withdrawing via the mesomeric effect. Examples of suitable electron withdrawing groups include halogen, —CN, —NO$_2$, acyl (e.g., an aldehyde, ketone, ester, amide, urea, carbonate, carbamate, or imide), a sulfoxide, a sulfone, a sulfinate, a sulfinamide, a sulfonate, a sulfonamide, or heteroaryl.

The term "intracellular conditions" refers to conditions of the internal milieu that occur in a subject (e.g., a human) naturally, as opposed to artificial laboratory conditions. In certain embodiments, intracellular conditions include a temperature range of about 20 to about 40° C. (e.g., about 37° C.), pressure of about 1 atmosphere, pH of about 6 to about 8 (e.g., about 7), glucose concentration of about 1 to about 20 mM, atmospheric oxygen concentration, and earth gravity. In certain embodiments, intracellular conditions are conditions that occur in a cyst cell (e.g., a cyst cell that causes polycystic kidney disease (PKD) or polycystic liver disease (PLD).

The term "stable under intracellular conditions" refers to a compound or a moiety of a compound (e.g., linker L of a compound of Formula (I) or (II)) showing a long half-life under intracellular conditions. The concentration of the compound or the moiety at the inception of the half-life measurement is a concentration effective for the intended use of the compound. In certain embodiments, the concentration of the compound or the moiety at the inception of the half-life measurement is the half maximal inhibitory concentration ($IC_{50}$) of the compound in inhibiting the growth of a cyst cell (e.g., a cyst cell that causes PKD or PLD). In certain embodiments, a long half-life is at least about 6 hours, at least about 12 hours, or at least about 24 hours. The term "hydrolytically unstable" refers to a compound or a moiety of a compound, each of which is not hydrolytically stable.

The term "hydrophobic" or "non-polar" refers to the ability of a compound to dissolve, or the ability of a moiety of a compound to assist the compound in dissolving in fats, oils, lipids, and/or non-polar solvents (e.g., hexane or toluene). Hydrophobic moieties include, but are not limited to, substituted or unsubstituted, branched or unbranched alkyl or alkylene groups having 1 to 50 carbon atoms. In certain embodiments, the hydrophobic moiety is an alkyl or alkylene group including at least 1, at least 6, at least 12, at least 18, at least 24, at least 36, or at least 50 carbon atoms. In certain embodiments, the hydrophobic moiety is unsubstituted alkyl or alkylene. In certain embodiments, the hydrophobic moiety is unsubstituted alkyl or alkylene. In certain embodiments, the hydrophobic moiety is unsubstituted $C_{1-24}$ alkyl or alkylene.

The term "hydrophilic" or "polar" refers to the ability of a compound to dissolve, or the ability of a moiety of a compound to assist the compound in dissolving in water. A hydrophilic compound or moiety typically includes one or more heteroatoms (e.g., atoms that are not carbon or hydrogen). In certain embodiments, the water solubility of a hydrophilic compound is at least about 1 mg/ml, at least about 3 mg/ml, or at least about 10 mg/ml at 25° C. and 1 atmosphere. A hydrophilic compound or moiety is not hydrophobic.

The term "subject" refers to any animal. In certain embodiments, the subject is a mammal. In certain embodiments, the subject is a human (e.g., a man, a woman, or a child). The human may be of either sex and may be at any stage of development. In certain embodiments, the subject has been diagnosed with the condition or disease to be treated. In other embodiments, the subject is at risk of developing the condition or disease. In certain embodiments, the subject is an experimental animal (e.g., mouse, rat, rabbit, dog, pig, or primate). The experimental animal may be genetically engineered. In certain embodiments, the subject is a domesticated animal (e.g., dog, cat, bird, horse, cow, goat, sheep).

The terms "administer," "administering," or "administration" refers to implanting, absorbing, ingesting, injecting, or inhaling a compound described herein, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of the present invention or a pharmaceutical composition thereof refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutically and prophylactically effective amounts.

A "therapeutically effective amount" of a compound of the present invention or a pharmaceutical composition thereof is an amount sufficient to provide a therapeutic benefit in the treatment of a disease or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound of the present invention is an amount sufficient to prevent a disease or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

BRIEF DESCRIPTION OF THE DRAWINGS

FIG. 3A to FIG. 3F are unlimited examples and show the effects of compound I-1 on the development of polycystic kidney disease (PKD) in Pkhd1-Cre mice. Mice were given daily intraperitoneal injections of compound I-1 between P10 and P24. (FIG. 3A): the staining was hematoxylin and eosin (H&E) stain. (FIG. 3B): the body weight of the mice. (FIG. 3C): the kidney weight of the mice. (FIG. 3D): the kidney/body weight ratio of the mice. (FIG. 3E): the cystic index results. (FIG. 3F): the blood urea nitrogen results.

In FIG. 4A, red or arrow: TUNEL positive; green, or highlight without arrow: DBA positive.

FIG. 6A to FIG. 6C are unlimited examples and show the efficacy of compound I-1 in an adult mouse model. 11 beta: compound I-1. FIG. 6A: images of the kidney of the mouse treated with vehicle (left panel) or compound I-1 (right panel). FIG. 6B: kidney/body weight ratios of the mice treated with vehicle or compound I-1. FIG. 6C: blood urea nitrogen (BUN) levels of the mice treated with vehicle or compound I-1. The legend also applies to FIG. 6B.

FIG. 7A: images of the kidney of the mouse treated with vehicle (left panel) or compound I-3 (right panel). FIG. 7B: kidney/body weight ratios of the mice treated with vehicle or compound I-3. FIG. 7C: blood urea nitrogen (BUN) levels of the mice treated with vehicle or compound I-3. The legend also applies to FIG. 7B.

FIG. 8A: fold changes of mRNA levels (by qPCR) of spliced XBP1 (XBP1s, the activated form of XBP1) in wild-type kidney treated with compound I-1 or in cystic kidney treated with vehicle or with compound I-1. FIG. 8B: protein levels (by Western blotting) of XBP1s and of caspase-12, a downstream effector of XBP1s.

DETAILED DESCRIPTION OF CERTAIN EMBODIMENTS OF THE INVENTION

Figure 1:
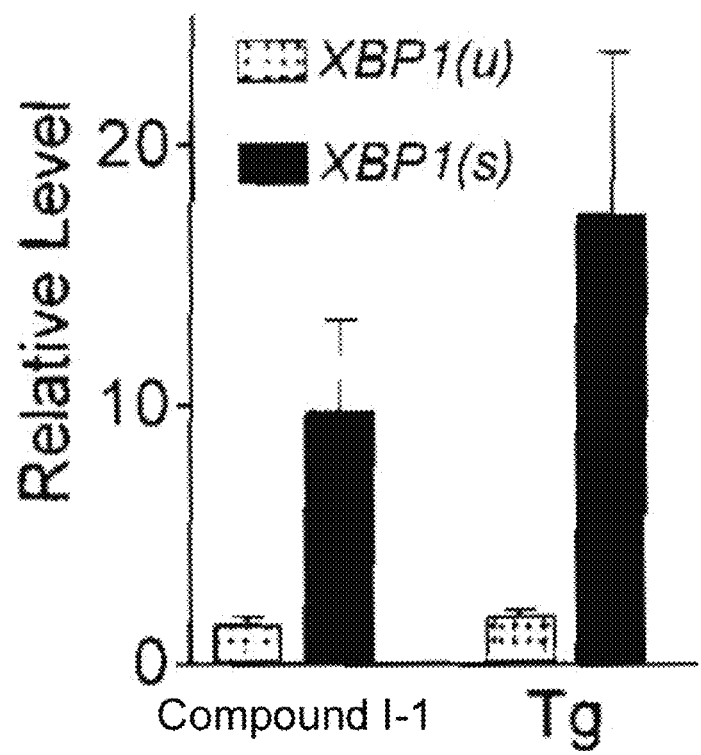
FIG. 1 is an unlimited example and shows the IRE 1 RNase activity in HeLa cells treated with compound I-1 (5 μM) or thapsigargin (Tg) (200 nM). Levels of spliced (s) and unspliced (u) XBP1 transcript relative to untreated cells are shown.
Figure 1:
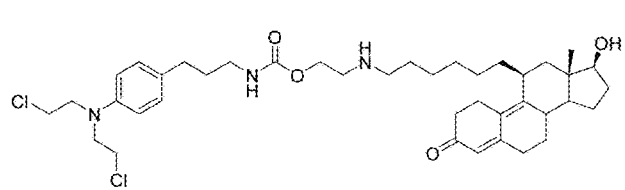
Figure 1:
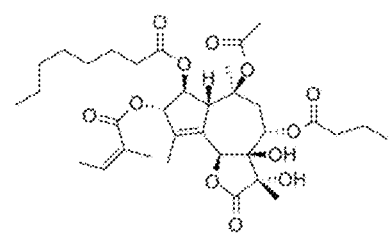

The present invention provides compounds of Formula (I) or (II), which are thought to be able to inhibit mTOR signaling pathway, induce UPR, and/or perturb mitochondrial function of a cyst cell (e.g., a cyst cell causing PKD or PLD). The invention also provides pharmaceutical compositions, kits, and methods involving the compounds described herein for use in treating PKD or PLD, inhibiting the growth of a cyst cell, and/or killing a cyst cell.

Compounds

One aspect of the invention relates to compounds that are useful for treating PKD and/or PLD. In certain embodiments, a compound of the invention is of Formula (I) or (II):

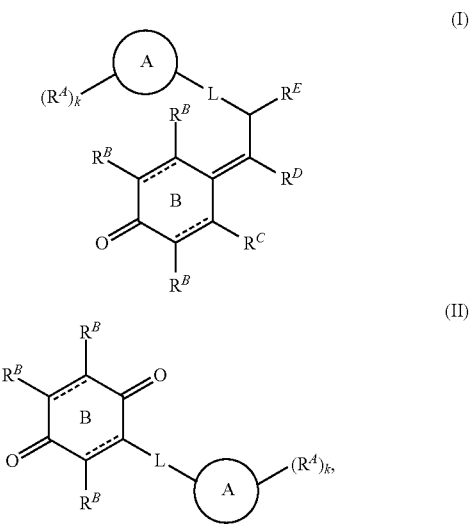

or a pharmaceutically acceptable salt, hydrate, solvate, polymorph, co-crystal, tautomer, or isotopically labeled derivative thereof, wherein:

Ring A is substituted or unsubstituted phenyl or naphthyl, or substituted or unsubstituted, monocyclic or bicyclic heteroaryl, wherein one, two, three, or four atoms in the heteroaryl ring system are independently selected from the group consisting of nitrogen, oxygen, and sulfur;

each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —C(=$NR^{A1}$)$R^{A1}$, —C(=$NR^{A1}$)$OR^{A1}$, —C(=$NR^{A1}$)$N(R^{A1})_2$, —C(=O)$R^{A1}$, —C(=O)$OR^{A1}$, —C(=O)$N(R^{A2})_2$, —$NO_2$, —$NR^{A1}$C(=O)$R^{A1}$, —$NR^{A1}$C(=O)$OR^{A1}$, —$NR^{A1}$C(=O)$N(R^{A1})_2$, —OC(=O)$R^{A1}$, —OC(=O)$OR^{A1}$, —OC(=O)$N(R^{A1})_2$, or a nitrogen protecting group when attached to a nitrogen atom, or optionally two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{A1}$ groups are joined to form a substituted or unsubstituted heterocyclic ring;

k is 0, 1, 2, 3, 4, or 5;

L is a linker stable under intracellular conditions;

one instance of === is a double bond;

the other instance of === is a single or double bond;

each instance of $R^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —SCN, —C(=NR$^{B1}$)R$^{B1}$, —C(=NR$^{B1}$)OR$^{B1}$, —C(=NR$^{N1}$)NR$^{B1}$)$_2$, —C(=O)R$^{B1}$, —C(=O)OR$^{B1}$, —C(=O)N(R$^{B1}$)$_2$, —NO$_2$, —NR$^{B1}$C(=O)R$^{B1}$, —NR$^{B1}$C(=O)OR$^{B1}$, —NR$^{B1}$C(=O)N(R$^{B1}$)$_2$, —OC(=O)R$^{B1}$, —OC(=O)OR$^{B1}$, —OC(=O)N(R$^{B1}$)$_2$, or a nitrogen protecting group when attached to a nitrogen atom, or optionally two R$^{B}$ groups are joined to form a substituted or unsubstituted carbocyclic, substituted or unsubstituted heterocyclic, substituted or unsubstituted aryl, or substituted or unsubstituted heteroaryl ring;

each instance of R$^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two R$^{B1}$ groups are joined to form a substituted or unsubstituted heterocyclic ring;

each instance of R$^{C}$, R$^{D}$, and R$^{E}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C1}$, —N(R$^{C1}$)$_2$, —SR$^{C1}$, —CN, —SCN, —C(=NR$^{C1}$)R$^{C1}$, —C(=NR$^{C1}$)OR$^{C1}$, —C(=NR$^{C1}$)N(R$^{C1}$)$_2$, —C(=O)R$^{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, —OC(=O)N(R$^{C1}$)$_2$, or a nitrogen protecting group when attached to a nitrogen atom;

each instance of R$^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two R$^{C1}$ groups are joined to form a substituted or unsubstituted heterocyclic ring;

optionally R$^{C}$ and R$^{D}$ are joined to form a substituted or unsubstituted, monocyclic carbocyclic ring; and optionally R$^{D}$ and R$^{E}$ are joined to form a substituted or unsubstituted, monocyclic or bicyclic carbocyclic ring.

A compound of Formula (I) or (II) includes Ring A, Ring B, and linker L that directly or indirectly connects Ring A and Ring B. In certain embodiments, Ring A is hydrophobic. In certain embodiments, Ring A is hydrophilic. In certain embodiments, Ring A, along with any substituents thereon, is stable under intracellular conditions. In certain embodiments, Ring A is unsubstituted phenyl. In certain embodiments, Ring A is substituted phenyl. In certain embodiments, Ring A is phenyl substituted with one or more substituents independently selected from the group consisting of halogen, substituted or unsubstituted alkyl, and —OR$^{A1}$. In certain embodiments, Ring A is phenyl substituted with one or more substituents independently selected from the group consisting of halogen, unsubstituted C$_{1-6}$ alkyl, C$_{1-6}$ alkyl substituted with one or more substituents independently selected from the group consisting of halogen and —O(unsubstituted C$_{1-6}$ alkyl), and —OR$^{A1}$, wherein R$^{A1}$ is hydrogen, unsubstituted C$_{1-6}$ alkyl, or C$_{1-6}$ alkyl substituted with one or more substituents independently selected from the group consisting of halogen and —O(unsubstituted C$_{1-6}$ alkyl). In certain embodiments, Ring A is of the formula

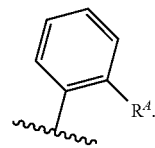

In certain embodiments, Ring A is of the formula:

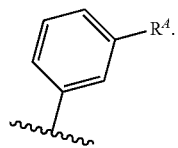

In certain embodiments, Ring A is of the formula

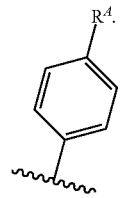

In certain embodiments, Ring A is of the formula:

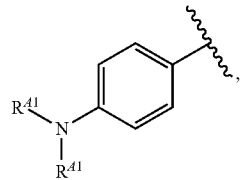

In certain embodiments, Ring A is of the formula:

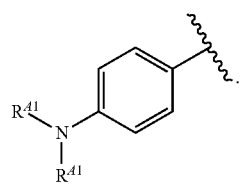

wherein each instance of R$^{A1}$ is independently substituted or unsubstituted C$_{1-6}$ alkyl. In certain embodiments, Ring A is of the formula:

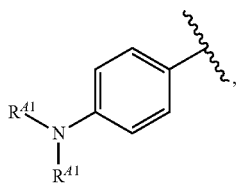

wherein each instance of $R^{A1}$ is independently unsubstituted $C_{1-6}$ alkyl or substituted $C_{1-6}$ alkyl substituted with one or more substituents independently selected from the group consisting of halogen and —O(unsubstituted $C_{1-6}$ alkyl). In certain embodiments, Ring A is of the formula:

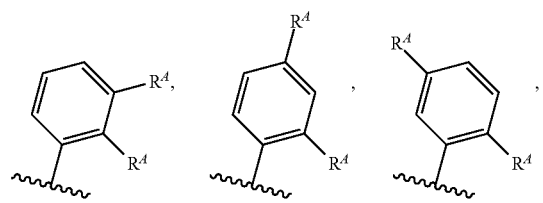

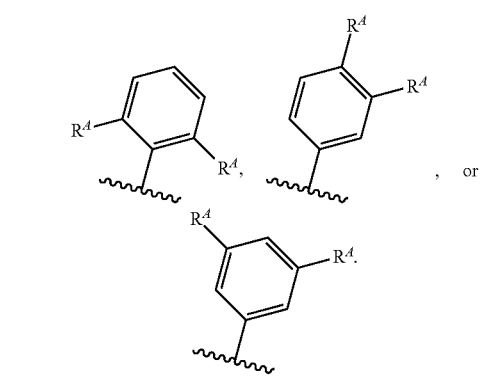

In certain embodiments, Ring A is unsubstituted naphthyl. In certain embodiments, Ring A is substituted naphthyl. In certain embodiments, Ring A is naphthyl substituted with one or more substituents independently selected from the group consisting of halogen, substituted or unsubstituted alkyl, and —OR$^{A1}$. In certain embodiments, Ring A is naphthyl substituted with one or more substituents independently selected from the group consisting of halogen, unsubstituted $C_{1-6}$ alkyl, $C_{1-6}$ alkyl substituted with one or more substituents independently selected from the group consisting of halogen and —O(unsubstituted $C_{1-6}$ alkyl), and —OR$^{A1}$, wherein $R^{A1}$ is hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl).

In certain embodiments, Ring A is substituted or unsubstituted, monocyclic heteroaryl, wherein one, two, three, or four atoms in the heteroaryl ring system are independently selected from the group consisting of nitrogen, oxygen, and sulfur. In certain embodiments, Ring A is substituted or unsubstituted, 5-membered, monocyclic heteroaryl, wherein one, two, three, or four atoms in the heteroaryl ring system are independently selected from the group consisting of nitrogen, oxygen, and sulfur. In certain embodiments, Ring A is of the formula:

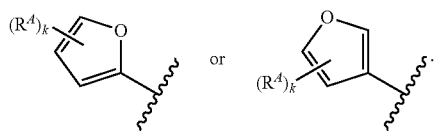

In certain embodiments, Ring A is of the formula:

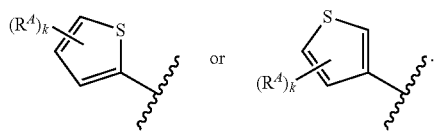

In certain embodiments, Ring A is of the formula:

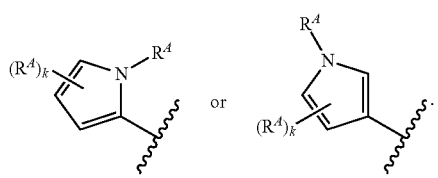

In certain embodiments, Ring A is of the formula:

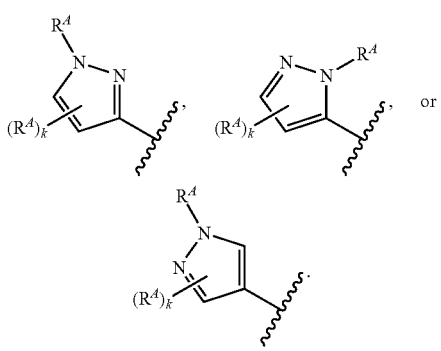

In certain embodiments, Ring A is of the formula:

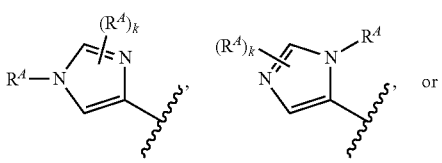

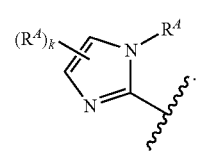

In certain embodiments, Ring A is of the formula:

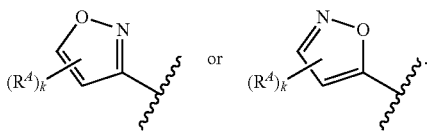 or

In certain embodiments, Ring A is of the formula:

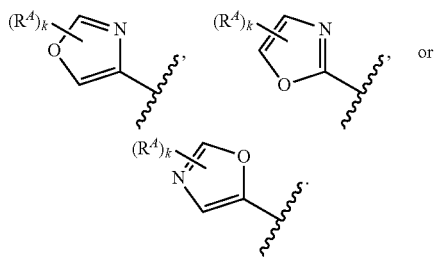

In certain embodiments, Ring A is of the formula:

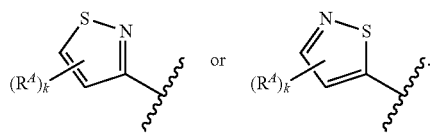 or

In certain embodiments, Ring A is of the formula:

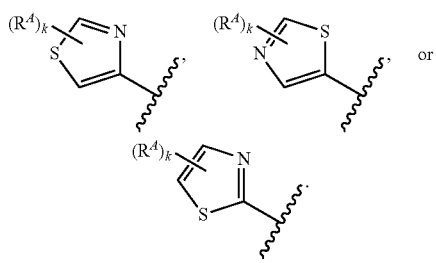 or

In certain embodiments, Ring A is of the formula:

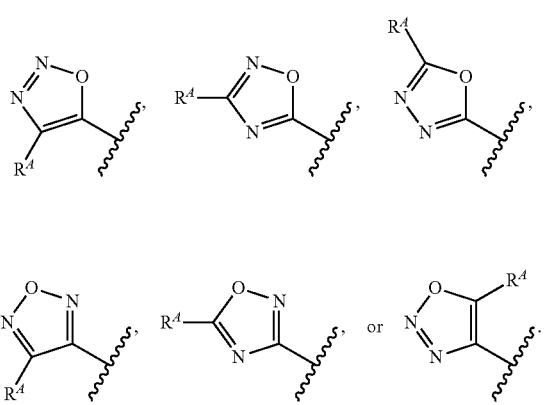

In certain embodiments, Ring A is of the formula:

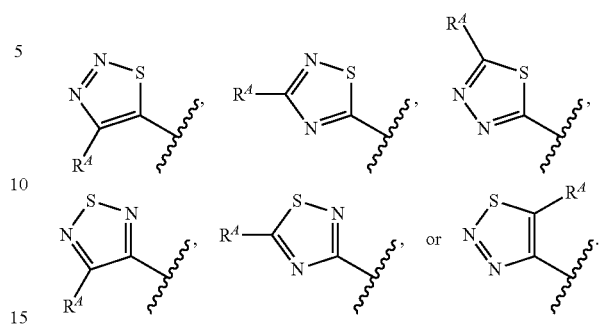

In certain embodiments, Ring A is of the formula:

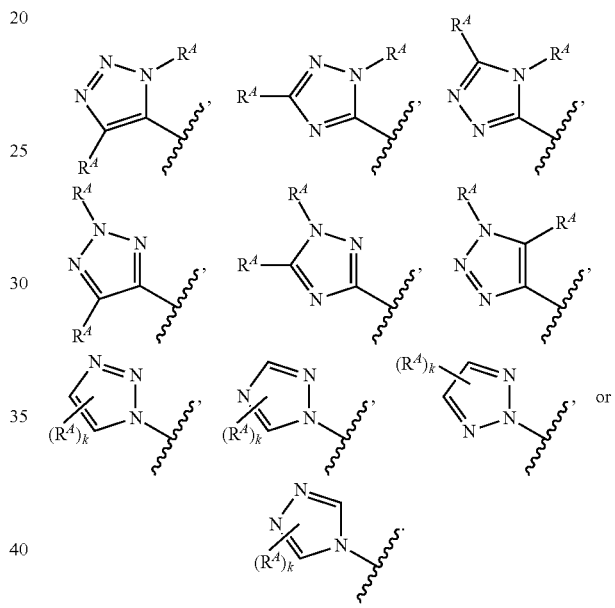

In certain embodiments, Ring A is of the formula:

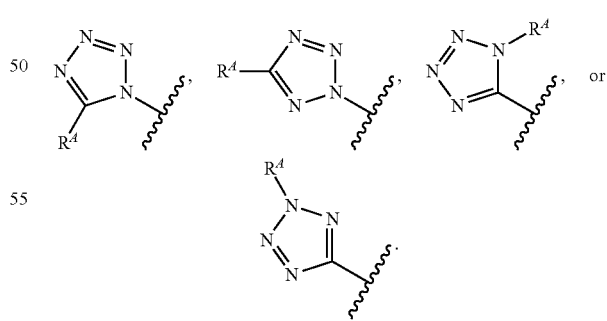

In certain embodiments, Ring A is substituted or unsubstituted, 6-membered, monocyclic heteroaryl, wherein one, two, three, or four atoms in the heteroaryl ring system are independently selected from the group consisting of nitrogen, oxygen, and sulfur. In certain embodiments, Ring A is of the formula

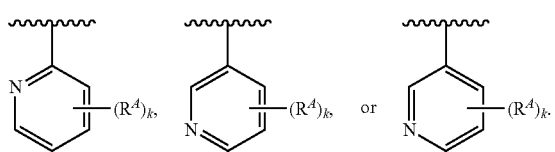

In certain embodiments, Ring A is of the formula:

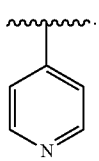

the formula: In certain embodiments, Ring A is of the formula:

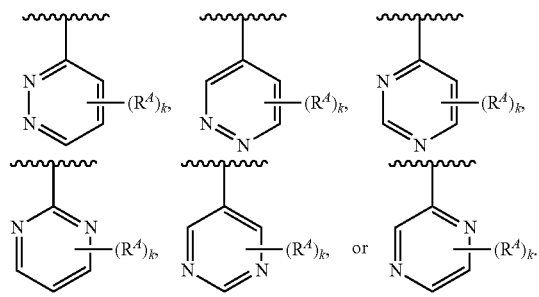

In certain embodiments, Ring A is of the formula:

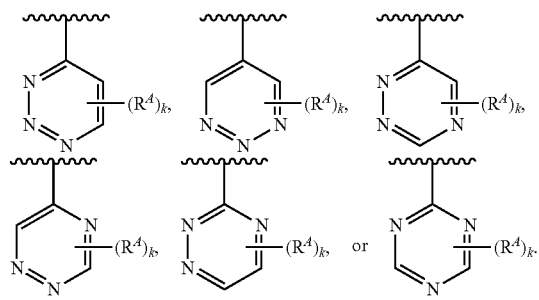

In certain embodiments, Ring A is substituted or unsubstituted, bicyclic heteroaryl, wherein one, two, three, or four atoms in the heteroaryl ring system are independently selected from the group consisting of nitrogen, oxygen, and sulfur. In certain embodiments, Ring A is substituted or unsubstituted, 9-membered, bicyclic heteroaryl, wherein one, two, three, or four atoms in the heteroaryl ring system are independently selected from the group consisting of nitrogen, oxygen, and sulfur. In certain embodiments, Ring A is substituted or unsubstituted, 10-membered, bicyclic heteroaryl, wherein one, two, three, or four atoms in the heteroaryl ring system are independently selected from the group consisting of nitrogen, oxygen, and sulfur. The point of attachment may be on any atom of the bicyclic heteroaryl ring system, as valency permits. In certain embodiments, when Ring A is substituted, monocyclic or bicyclic heteroaryl, the heteroaryl is substituted with one or more substituents independently selected from the group consisting of halogen, substituted or unsubstituted alkyl, and —$OR^{A1}$.

In certain embodiments, when Ring A is substituted, monocyclic or bicyclic heteroaryl, the heteroaryl is substituted with one or more substituents independently selected from the group consisting of halogen, unsubstituted $C_{1-6}$ alkyl, $C_{1-6}$ alkyl substituted with one or more substituents independently selected from the group consisting of halogen and —O(unsubstituted $C_{1-6}$ alkyl), and —$OR^{A1}$, wherein $R^{A1}$ is hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl).

Ring A of Formula (I) or (II) may include one or more substituent $R^A$. In certain embodiments, at least one instance of $R^A$ is H. In certain embodiments, at least one instance of $R^A$ is halogen. In certain embodiments, at least one instance of $R^A$ is F. In certain embodiments, at least one instance of $R^A$ is Cl. In certain embodiments, at least one instance of $R^A$ is Br or I (iodine). In certain embodiments, at least one instance of $R^A$ is substituted acyl. In certain embodiments, at least one instance of $R^A$ is unsubstituted acyl. In certain embodiments, at least one instance of $R^A$ is substituted alkyl. In certain embodiments, at least one instance of $R^A$ is unsubstituted alkyl. In certain embodiments, at least one instance of $R^A$ is $C_{1-12}$ alkyl. In certain embodiments, at least one instance of $R^A$ is $C_{1-6}$ alkyl. In certain embodiments, at least one instance of $R^A$ is unsubstituted methyl. In certain embodiments, at least one instance of $R^A$ is substituted methyl. In certain embodiments, at least one instance of $R^A$ is $CH_2F$, $CHF_2$, or $CF_3$. In certain embodiments, at least one instance of $R^A$ is Bn. In certain embodiments, at least one instance of $R^A$ is ethyl. In certain embodiments, at least one instance of $R^A$ is propyl, butyl, pentyl, or hexyl. In certain embodiments, at least one instance of $R^A$ is substituted alkenyl. In certain embodiments, at least one instance of $R^A$ is unsubstituted alkenyl. In certain embodiments, at least one instance of $R^A$ is vinyl. In certain embodiments, at least one instance of $R^A$ is substituted alkynyl. In certain embodiments, at least one instance of $R^A$ is unsubstituted alkynyl. In certain embodiments, at least one instance of $R^A$ is ethynyl. In certain embodiments, at least one instance of $R^A$ is substituted carbocyclyl. In certain embodiments, at least one instance of $R^A$ is unsubstituted carbocyclyl. In certain embodiments, at least one instance of $R^A$ is saturated carbocyclyl. In certain embodiments, at least one instance of $R^A$ is unsaturated carbocyclyl. In certain embodiments, at least one instance of $R^A$ is carbocyclyl including one, two, or three double bonds in the carbocyclic ring. In certain embodiments, at least one instance of $R^A$ is monocyclic carbocyclyl. In certain embodiments, at least one instance of $R^A$ is 3- to 7-membered, monocyclic carbocyclyl. In certain embodiments, at least one instance of $R^A$ is cylcopropyl. In certain embodiments, at least one instance of $R^A$ is cyclobutyl, cyclopentyl, cyclohexyl, or cycloheptyl. In certain embodiments, at least one instance of $R^A$ is bicyclic carbocyclyl. In certain embodiments, at least one instance of $R^A$ is 5- to 13-membered, bicyclic carbocyclyl. In certain embodiments, at least one instance of $R^A$ is substituted heterocyclyl. In certain embodiments, at least one instance of $R^A$ is unsubstituted heterocyclyl. In certain embodiments, at least one instance of $R^A$ is saturated heterocyclyl. In certain embodiments, at least one instance of $R^A$ is unsaturated heterocyclyl. In certain embodiments, at least one instance of $R^A$ is heterocyclyl including one, two, or three double bonds in the heterocyclic ring. In certain embodiments, at least one instance of $R^A$ is heterocyclyl, wherein one, two, or three atoms in the heterocyclic ring are independently selected from the group consisting of nitrogen, oxygen, and sulfur. In certain embodiments, at least one instance of $R^A$ is monocyclic heterocyclyl. In certain embodiments, at least one instance of $R^A$ is 3- to 7-membered, monocyclic heterocyclyl. In certain embodiments, at least one instance of $R^A$ is bicyclic heterocyclyl. In certain embodiments, at least one instance of $R^A$ is 5- to 13-membered, bicyclic heterocyclyl. In certain embodiments, at least one instance of $R^A$ is substituted aryl. In certain embodiments, at least one instance of $R^A$ is unsubstituted aryl. In certain embodiments, at least one instance of $R^A$ is 6- to 14-membered aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted naphthyl. In certain embodiments, at least one instance of $R^A$ is unsubstituted naphthyl. In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms in the heteroaryl ring are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is pyridyl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9-membered, bicyclic heteroaryl. In certain embodiments, at least one instance of $R^A$ is 10-membered, bicyclic heteroaryl. In certain embodiments, at least one instance of $R^A$ is —$OR^{A1}$. In certain embodiments, at least one instance of $R^A$ is —OMe. In certain embodiments, at least one instance of $R^A$ is —OEt. In certain embodiments, at least one instance of $R^A$ is —OPr, —OBu, —O(pentyl), or —O(hexyl). In certain embodiments, at least one instance of $R^A$ is —OPh. In certain embodiments, at least one instance of $R^A$ is —OBn. In certain embodiments, at least one instance of $R^A$ is —OH. In certain embodiments, at least one instance of $R^A$ is —$SR^{A1}$. In certain embodiments, at least one instance of $R^A$ is —SMe. In certain embodiments, at least one instance of $R^A$ is —SH. In certain embodiments, at least one instance of $R^A$ is —$N(R^{A1})_2$. In certain embodiments, at least one instance of $R^A$ is —$N(R^{A1})_2$, wherein each instance of $R^{A1}$ is independently substituted or unsubstituted $C_{1-6}$ alkyl. In certain embodiments, at least one instance of $R^A$ is —$N(R^{A1})_2$, wherein each instance of $R^{A1}$ is independently unsubstituted $C_{1-6}$ alkyl or $C_{1-6}$ alkyl substituted with one or more substituents independently selected from the group consisting of halogen and —O (unsubstituted $C_{1-6}$ alkyl). In certain embodiments, at least one instance of $R^A$ is —$NMe_2$. In certain embodiments, at least one instance of $R^A$ is —$NH_2$. In certain embodiments, at least one instance of $R^A$ is —CN. In certain embodiments, at least one instance of $R^A$ is —SCN. In certain embodiments, at least one instance of $R^A$ is —$C(=NR^{A1})R^{A1}$, —$C(=NR^{A1})OR^{A1}$, or —$C(=NR^{A1})N(R^{A1})_2$. In certain embodiments, at least one instance of $R^A$ is —$C(=O)R^{A1}$, —$C(=O)OR^{A1}$, or —$C(=O)N(R^{A1})_2$. In certain embodiments, at least one instance of $R^A$ is —$NO_2$. In certain embodiments, at least one instance of $R^A$ is —$NR^{A1}C(=O)R^{A1}$, —$N_{A1}C(=O)O^{A1}$, or —$NR^{A1}C(=O)N(R^{A1})_2$. In certain embodiments, at least one instance of $R^A$ is —$O(=O)R^{A1}$, —$OC(=O)OR^{A1}$, or —$OC(=O)N(R^{A1})_2$.

In compounds of Formula (I) or (II), two $R^A$ groups may be joined to form a substituted or unsubstituted carbocyclic ring. In certain embodiments, two instances of $R^A$ are joined to form a saturated or unsaturated carbocyclic ring. In certain embodiments, two instances of $R^A$ are joined to form a carbocyclic ring including one, two, or three double bonds in the carbocyclic ring. In certain embodiments, two instances of $R^A$ are joined to form a 3- to 7-membered, monocyclic carbocyclic ring. In certain embodiments, two instances of $R^A$ are joined to form a 3-membered carbocyclic ring (e.g., cyclopropyl ring).

In certain embodiments, two instances of $R^A$ are joined to form a substituted or unsubstituted heterocyclic ring. In certain embodiments, two instances of $R^A$ are joined to form a saturated or unsaturated heterocyclic ring. In certain embodiments, two instances of $R^A$ are joined to form a heterocyclic ring including one, two, or three double bonds in the heterocyclic ring. In certain embodiments, two instances of $R^A$ are joined to form a heterocyclic ring, wherein one, two, or three atoms in the heterocyclic ring are independently selected from the group consisting of nitrogen, oxygen, and sulfur. In certain embodiments, two instances of $R^A$ are joined to form a 3- to 7-membered, monocyclic heterocyclic ring. In certain embodiments, two instances of $R^A$ are joined to form a 5- to 13-membered, bicyclic heterocyclic ring.

In certain embodiments, two instances of $R^A$ are joined to form a substituted or unsubstituted aryl ring. In certain embodiments, two instances of $R^A$ are joined to form a 6- to 14-membered aryl ring. In certain embodiments, two instances of $R^A$ are joined to form a 6- to 10-membered aryl ring. In certain embodiments, two instances of $R^A$ are joined to form a monocyclic aryl ring. In certain embodiments, two instances of $R^A$ are joined to form a phenyl. In certain embodiments, two instances of $R^A$ are joined to form a bicyclic aryl ring. In certain embodiments, two instances of $R^A$ are joined to form a naphthyl.

In certain embodiments, two instances of $R^A$ are joined to form a substituted or unsubstituted heteroaryl ring. In certain embodiments, two instances of $R^A$ are joined to form a monocyclic heteroaryl ring, wherein one, two, or three atoms in the heteroaryl ring are independently selected from the group consisting of nitrogen, oxygen, and sulfur. In certain embodiments, two instances of $R^A$ are joined to form a 5-membered, monocyclic heteroaryl ring. In certain embodiments, two instances of $R^A$ are joined to form a 6-membered, monocyclic heteroaryl ring. In certain embodiments, two instances of $R^A$ are joined to form a pyridyl. In certain embodiments, two instances of $R^A$ are joined to form a bicyclic heteroaryl ring, wherein one, two, three, or four atoms in the heteroaryl ring are independently selected from the group consisting of nitrogen, oxygen, and sulfur. In certain embodiments, two instances of $R^A$ are joined to form a 9-membered, bicyclic heteroaryl ring. In certain embodiments, two instances of $R^A$ are joined to form a 10-membered, bicyclic heteroaryl ring.

In certain embodiments, at least one instance of $R^A$ is halogen or substituted or unsubstituted alkyl. In certain embodiments, at least one instance of $R^A$ is halogen, unsubstituted $C_{1-6}$ alkyl, or $C_{1-6}$ alkyl substituted with one or more substituents independently selected from the group consisting of halogen and —O(unsubstituted $C_{1-6}$ alkyl).

In certain embodiments, at least one instance of $R^{A1}$ is H. In certain embodiments, at least one instance of $R^{A1}$ is substituted acyl. In certain embodiments, at least one instance of $R^{A1}$ is unsubstituted acyl. In certain embodiments, at least one instance of $R^{A1}$ is acetyl. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is $C_{1-12}$ alkyl. In certain embodiments, at least one instance of $R^{A1}$ is $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl, butyl, pentyl, or hexyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is vinyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is ethynyl. In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is saturated carbocyclyl. In certain embodiments, at least one instance of $R^{A1}$ is unsaturated carbocyclyl. In certain embodiments, at least one instance of $R^{A1}$ is carbocyclyl including one, two, or three double bonds in the carbocyclic ring. In certain embodiments, at least one instance of $R^{A1}$ is 3- to 7-membered, monocyclic carbocyclyl. In certain embodiments, at least one instance of $R^{A1}$ is cylcopropyl. In certain embodiments, at least one instance of $R^{A1}$ is cyclobutyl, cyclopentyl, cyclohexyl, or cycloheptyl. In certain embodiments, at least one instance of $R^{A1}$ is 5- to 13-membered, bicyclic carbocyclyl. In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is saturated heterocyclyl. In certain embodiments, at least one instance of $R^{A1}$ is unsaturated heterocyclyl. In certain embodiments, at least one instance of $R^{A1}$ is heterocyclyl including one, two, or three double bonds in the heterocyclic ring. In certain embodiments, at least one instance of $R^{A1}$ is heterocyclyl, wherein one, two, or three atoms in the heterocyclic ring are independently selected from the group consisting of nitrogen, oxygen, and sulfur. In certain embodiments, at least one instance of $R^{A1}$ is 3- to 7-membered, monocyclic heterocyclyl. In certain embodiments, at least one instance of $R^{A1}$ is 5- to 13-membered, bicyclic heterocyclyl. In certain embodiments, at least one instance of $R^{A1}$ is substituted or unsubstituted aryl. In certain embodiments, at least one instance of $R^{A1}$ is 6- to 14-membered aryl. In certain embodiments, at least one instance of $R^{A1}$ is 6- to 10-membered aryl. In certain embodiments, at least one instance of $R^{A1}$ is monocyclic aryl. In certain embodiments, at least one instance of $R^{A1}$ is phenyl. In certain embodiments, at least one instance of $R^{A1}$ is bicyclic aryl. In certain embodiments, at least one instance of $R^{A1}$ is naphthyl. In certain embodiments, at least one instance of $R^{A1}$ is substituted or unsubstituted heteroaryl. In certain embodiments, at least one instance of $R^{A1}$ is heteroaryl, wherein one, two, three, or four atoms in the heteroaryl ring are independently selected from the group consisting of nitrogen, oxygen, and sulfur. In certain embodiments, at least one instance of $R^{A1}$ is monocyclic heteroaryl. In certain embodiments, at least one instance of $R^{A1}$ is 5-membered, monocyclic heteroaryl. In certain embodiments, at least one instance of $R^{A1}$ is 6-membered, monocyclic heteroaryl. In certain embodiments, at least one instance of $R^{A1}$ is pyridyl. In certain embodiments, at least one instance of $R^{A1}$ is bicyclic heteroaryl, wherein the point of attachment may be on any atom of the bicyclic heteroaryl ring system, as valency permits. In certain embodiments, at least one instance of $R^{A1}$ is 9-membered, bicyclic heteroaryl. In certain embodiments, at least one instance of $R^{A1}$ is 10-membered, bicyclic heteroaryl. In certain embodiments, at least one instance of $R^{A1}$ is a nitrogen protecting group when attached to a nitrogen atom. In certain embodiments, at least one instance of $R^{A1}$ is Bn, Boc, Cbz, Fmoc, trifluoroacetyl, triphenylmethyl, acetyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{A1}$ are joined to form a substituted or unsubstituted heterocyclic ring. In certain embodiments, two instances of $R^{A1}$ are joined to form a saturated or unsaturated heterocyclic ring. In certain embodiments, two instances of $R^{A1}$ are joined to form a heterocyclic ring including one, two, or three double bonds in the heterocyclic ring. In certain embodiments, two instances of $R^{A1}$ are joined to form a heterocyclic ring, wherein one, two, or three atoms in the heterocyclic ring are independently selected from the group consisting of nitrogen, oxygen, and sulfur. In certain embodiments, two instances of $R^{A1}$ are joined to form a 3- to 7-membered, monocyclic heterocyclic ring. In certain embodiments, two instances of $R^{A1}$ are joined to form a 5- to 13-membered, bicyclic heterocyclic ring.

In certain embodiments, k is 0. In certain embodiments, k is 1. In certain embodiments, k is 2. In certain embodiments, k is 3. In certain embodiments, k is 4. In certain embodiments, k is 5.

In compounds of Formula (I) or (II), L is a linker stable under intracellular conditions. According to aspects of the invention, L may have one or more of the following properties: solubility under intracellular conditions, stability under intracellular conditions, and/or a length (e.g., a length of a carbon alkyl chain) that is therapeutically optimized (e.g., optimized to simultaneously allow the (Ring A)-(target molecule) interaction and the (Ring B)-(target molecule) interaction). In certain embodiments, L is hydrophilic. In certain embodiments, L is hydrophobic. In certain embodiments, both Ring A and L are hydrophilic. In certain embodiments, In certain embodiments, both Ring A and L are hydrophobic. In certain embodiments, Ring A is hydrophobic; and L is hydrophilic. In certain embodiments, Ring A is hydrophilic; and L is hydrophobic. In certain embodiments, a polar or charged moiety (e.g., a carbamate, amine, or sulfate) in L is separated from Ring A and/or Ring B by one or more carbons (e.g., 2, 3, 4, 5, or 6) so that the portion of L adjacent to Ring A and/or the portion of L adjacent to Ring B are relatively non-polar or hydrophobic. This property may be useful to enhance the binding of Ring A and/or Ring B to a non-polar or hydrophobic molecule (e.g., certain steroid receptors). In certain embodiments, L does not contain bonds that are degradable or unstable under intracellular conditions. In certain embodiments, L does not contain urea, ester, or amide moieties.

In certain embodiments, the molecular weight of L is less than about 500. In certain embodiments, the molecular weight of L is less than about 400. In certain embodiments, the molecular weight of L is less than about 300. In certain embodiments, the molecular weight of L is less than about 200. In certain embodiments, the molecular weight of L is less than about 150. In certain embodiments, the molecular weight of L is less than about 100. In certain embodiments, L consists of less than about 100 atoms. In certain embodiments, L consists of less than about 80 atoms. In certain embodiments, L consists of less than about 60 atoms. In certain embodiments, L consists of less than about 50 atoms. In certain embodiments, L consists of less than about 40 atoms. In certain embodiments, L consists of less than about 5 unsaturated bonds. In certain embodiments, L consists of less than 4 unsaturated bonds. In certain embodiments, L consists of less than 3 unsaturated bonds. In certain embodiments, L consists of less than 2 unsaturated bonds.

L may contain one or more polar or charged residues in order to improve solubility under intracellular conditions. L may contain one or more carbamate(s) and/or one or more amine(s) (e.g., secondary amines) in order to increase solubility under intracellular conditions. Alternatively, or in addition, the linker may contain one or more sulfates. In certain embodiments, L is an alkylene-amino-alkylene-carbamate-alkylene chain or an alkylene-carbamate-alkylene-amino-alkylene chain. In certain embodiments, L is a substituted or unsubstituted $C_{1-30}$ hydrocarbon chain, optionally wherein one or more carbon units of the hydrocarbon chain are independently replaced with —O—, —S—, —NR$^L$—, —S(=O)—, or —S(=O)$_2$; and each instance of R$^L$ is independently hydrogen, substituted or unsubstituted $C_{1-6}$ alkyl, or a nitrogen protecting group. In certain embodiments, L is a substituted or unsubstituted $C_{6-22}$ hydrocarbon chain, optionally wherein one or more carbon units of the hydrocarbon chain are independently replaced with —O—, —S—, —NR$^L$—, —S(=O)—, or —S(=O)$_2$—. In certain embodiments, L is a substituted or unsubstituted $C_{14-16}$ hydrocarbon chain, optionally wherein one or more carbon units of the hydrocarbon chain are independently replaced with —O—, —S—, —NR$^L$—, —S(=O)—, or —S(=O)$_2$—. In certain embodiments, 1 to 5 carbon units of L are independently replaced with —O—, —S—, —NR$^L$—, —S(=O)—, or —S(=O)$_2$—. In certain embodiments, 2 to 4 carbon units of L are independently replaced with —O—, —S—, —NR$^L$—, —S(=O)—, or —S(=O)$_2$—. In certain embodiments, 3 carbon units of L are independently replaced with —O— or —NR$^L$—.

In certain embodiments, at least one instance of R$^L$ is hydrogen. In certain embodiments, at least one instance of R$^L$ is substituted alkyl. In certain embodiments, at least one instance of R$^L$ is unsubstituted alkyl. In certain embodiments, at least one instance of R$^L$ is $C_{1-12}$ alkyl. In certain embodiments, at least one instance of R$^L$ is $C_{1-6}$ alkyl. In certain embodiments, at least one instance of R$^L$ is unsubstituted methyl. In certain embodiments, at least one instance of R$^L$ is substituted methyl. In certain embodiments, at least one instance of R$^L$ is —CHF, —CHF, or —CF$_3$. In certain embodiments, at least one instance of R$^L$ is Bn. In certain embodiments, at least one instance of R$^L$ is ethyl, propyl, butyl, pentyl, or hexyl. In certain embodiments, at least one instance of R$^L$ is a nitrogen protecting group. In certain embodiments, at least one instance of R$^L$ is Bn, Boc, Cbz, Fmoc, trifluoroacetyl, triphenylmethyl, acetyl, or Ts. In certain embodiments, at least one instance of R$^L$ is hydrogen, unsubstituted $C_{1-6}$ alkyl, and $C_{1-6}$ alkyl substituted with one or more substituents independently selected from the group consisting of halogen and —O (unsubstituted $C_{1-6}$ alkyl).

In linker L, each instance of the carbon units of the $C_{1-30}$ hydrocarbon chain may be independently substituted. In certain embodiments, at least one instance of the carbon units of the $C_{1-30}$ hydrocarbon chain is substituted with hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, =O, —OR$^{L1}$, —N(R$^{L1}$)$_2$, —SR$^{L1}$, —CN, —SCN, —C(=NR$^{L1}$)R$^{L1}$, —C(=NR$^{L1}$)OR$^{L1}$, —C(=NR$^{L1}$)N(R$^{L1}$)$_2$, —C(=O)R$^{L1}$, —C(=O)OR$^{L1}$, —C(=O)N(R$^{L1}$)$_2$, —S(=O)R$^{L1}$, —S(=O)OR$^{L1}$, —S(=O)N(R$^{L1}$)$_2$, —S(=O)$_2$R$^{L1}$, —S(=O)$_2$OR$^{L1}$, —S(=O)$_2$N(R$^{L1}$)$_2$, —NO$_2$, —NR$^{L1}$C(=O)R$^{id}$, —NR$^{L1}$C(=O)OR$^{L1}$, —NR$^{L1}$C(=O)N(R$^{L1}$)$_2$, —NR$^{L1}$S(=O)R$^{L1}$, —NR$^{L1}$S(=O)OR$^{L1}$, —NR$^{L1}$S(=O)N(R$^{L1}$)$_2$, —NR$^{L1}$S(=O)$_2$R$^{L1}$, —NR$^{L1}$S(=O)$_2$OR$^{L1}$, —NR$^{L1}$S(=O)$_2$N(R$^{L1}$)$_2$, —OC(=O)R$^{L1}$, —OC(=O)OR$^{L1}$, —OC(=O)N(R$^{L1}$)$_2$, —OS(=O)R$^{L1}$, —OS(=O)OR$^{L1}$, —OS(=O)N(R$^{L1}$)$_2$, —OS(=O)$_2$R$^{L1}$, —OS(=O)$_2$OR$^{L1}$, —OS(=O)$_2$N(R$^{L1}$)$_2$ wherein each occurrence of R$^{L1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{L1}$ groups are joined to form an substituted or unsubstituted heterocyclic ring. In certain embodiments, at least one instance of the carbon units of the $C_{1-30}$ hydrocarbon chain is substituted with halogen, =O, or substituted or unsubstituted alkyl. In certain embodiments, at least one instance of the carbon units of the $C_{1-30}$ hydrocarbon chain is substituted with halogen, =O, unsubstituted $C_{1-6}$ alkyl, or $C_{1-6}$ alkyl substituted with one or more substituents independently selected from the group consisting of halogen and —O(unsubstituted $C_{1-6}$ alkyl). In certain embodiments, at least one instance of the carbon units of the $C_{1-30}$ hydrocarbon chain is substituted with =O.

In certain embodiments, L is of the formula:

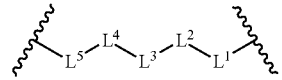

wherein:

$L^1$, $L^3$, and $L^5$ are independently a bond or substituted or unsubstituted $C_{1-10}$ hydrocarbon chain (e.g., $C_{1-10}$ hydrocarbon chain substituted with at least one instance of F); and $L^2$ and $L^4$ are independently a bond, —O—, —NR$^L$— (e.g., —NH— or —N(CF$_3$)—), —NR$^1$C(=O)O—, —OC(=O)NR$^1$—, —CHF—NR$^1$— (e.g., CHF—NH—), —NR$^1$—CHF— (e.g., —NH—CHF)—), —CF$_2$—NR$^L$— (e.g., —CF$_2$—NH—), —NR$^L$—CF$_2$— (e.g., —NH—CF$_2$—),

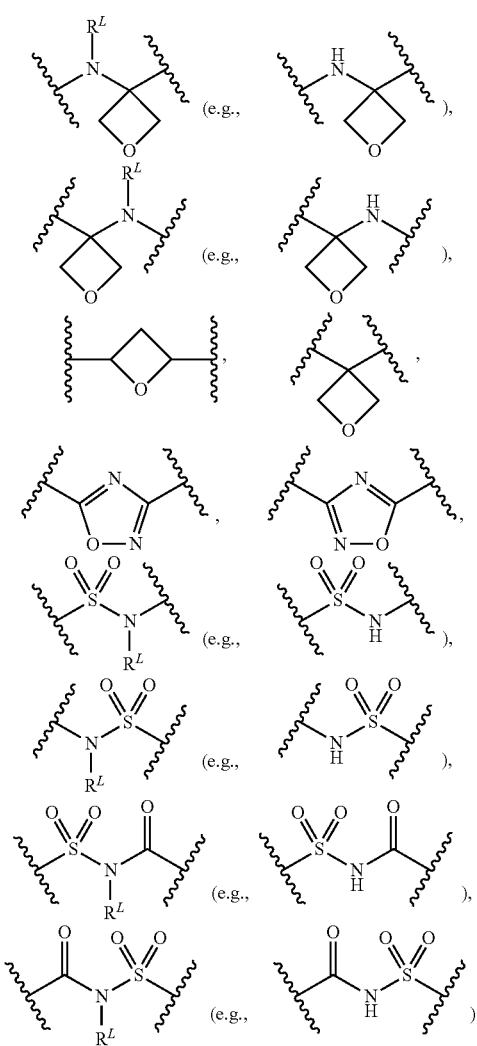

provided that at least one of $L^2$ and $L^4$ is not a bond. In certain embodiments, L is of the formula:

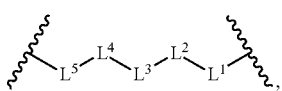

wherein $L^1$, $L^3$, and $L^5$ are independently a substituted or unsubstituted $C_{1-10}$ hydrocarbon chain (e.g., $C_{1-10}$ hydrocarbon chain substituted with at least one instance of F); and $L^2$ and $L^4$ are independently —O—, —NR$^L$— (e.g., —NH— or —N(CF$_3$)—), —NR$^L$—C(=O)O—, or —OC(=O)NR$^L$—. In certain embodiments, L is of the formula:

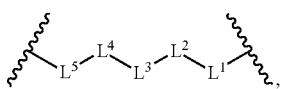

wherein $L^1$, $L^3$, and $L^5$ are independently a substituted or unsubstituted $C_{1-10}$ hydrocarbon chain (e.g., $C_{1-10}$ hydrocarbon chain substituted with at least one instance of F); and $L^2$ and $L^4$ are independently —NR$^L$— (e.g., —NH— or —N(CF$_3$)—), —NR$^L$C(=O)O—, or —OC(=O)NR$^L$—. In certain embodiments, L is of the formula:

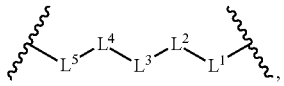

wherein $L^1$, $L^3$, and $L^5$ are independently an unsubstituted $C_{1-8}$ hydrocarbon chain or a $C_{1-8}$ hydrocarbon chain substituted with one or more substituents independently selected from the group consisting of halogen (e.g., F) and —O(unsubstituted $C_{1-6}$ alkyl); $L^2$ and $L^4$ are independently —NR$^L$—, —NR$^L$C(=O)O—, or —OC(=O)NR$^L$—; and each instance of R$^L$ is independently hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl). In certain embodiments, L is of the formula:

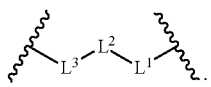

In certain embodiments, L is of the formula:

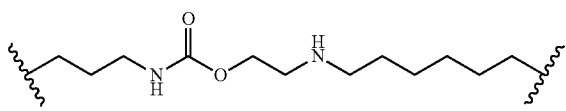 [SMILES: *CCCCCCNCCOC(=O)NCCC*]

In certain embodiments, L is of the formula:

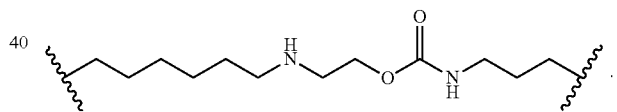

In certain embodiments, L is of the formula:

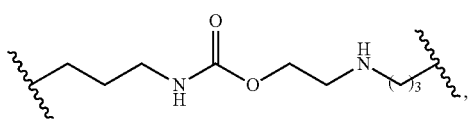

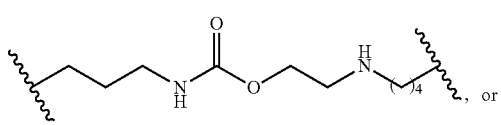

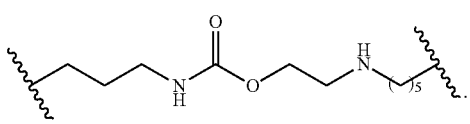

In certain embodiments, L is of the formula:

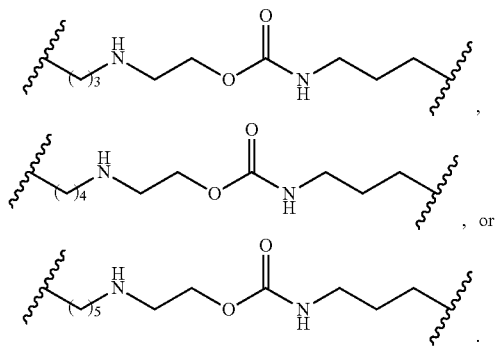

,

In certain embodiments, L is of the formula:

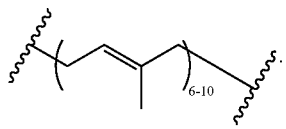

.

In certain embodiments, $L^1$, $L^3$, and $L^5$ are each independently an unsubstituted $C_{2-6}$ hydrocarbon chain or a $C_{2-6}$ hydrocarbon chain substituted with at least one instance of F.

A compound of Formula (I) or (II) includes substituted or unsubstituted Ring B. In certain embodiments, one instance of ═══ is a double bond; the other instance of ═══ is a single bond. In certain embodiments, each instances of ═══ is a double bond.

A compound of Formula (I) or (II) may include one or more substituents $R^B$ on Ring B. In certain embodiments, at least one instance of $R^B$ is H. In certain embodiments, at least one instance of $R^B$ is halogen. In certain embodiments, at least one instance of $R^B$ is F. In certain embodiments, at least one instance of $R^B$ is Cl. In certain embodiments, at least one instance of $R^B$ is Br or I (iodine). In certain embodiments, at least one instance of $R^B$ is substituted acyl. In certain embodiments, at least one instance of $R^B$ is unsubstituted acyl. In certain embodiments, at least one instance of $R^B$ is substituted alkyl. In certain embodiments, at least one instance of $R^B$ is unsubstituted alkyl. In certain embodiments, at least one instance of $R^B$ is $C_{1-12}$ alkyl. In certain embodiments, at least one instance of $R^B$ is $C_{1-6}$ alkyl. In certain embodiments, at least one instance of $R^B$ is unsubstituted methyl. In certain embodiments, at least one instance of $R^B$ is substituted methyl. In certain embodiments, at least one instance of $R^B$ is —$CH_2F$, —$CHF_2$, or —$CF_3$. In certain embodiments, at least one instance of $R^B$ is Bn. In certain embodiments, at least one instance of $R^B$ is ethyl. In certain embodiments, at least one instance of $R^B$ is propyl, butyl, pentyl, or hexyl. In certain embodiments, at least one instance of $R^B$ is substituted alkenyl. In certain embodiments, at least one instance of $R^B$ is unsubstituted alkenyl. In certain embodiments, at least one instance of $R^B$ is vinyl. In certain embodiments, at least one instance of $R^B$ is substituted alkynyl. In certain embodiments, at least one instance of $R^B$ is unsubstituted alkynyl. In certain embodiments, at least one instance of $R^B$ is ethynyl. In certain embodiments, at least one instance of $R^B$ is substituted carbocyclyl. In certain embodiments, at least one instance of $R^B$ is unsubstituted carbocyclyl. In certain embodiments, at least one instance of $R^B$ is saturated carbocyclyl. In certain embodiments, at least one instance of $R^B$ is unsaturated carbocyclyl. In certain embodiments, at least one instance of $R^B$ is carbocyclyl including one, two, or three double bonds in the carbocyclic ring. In certain embodiments, at least one instance of $R^B$ is monocyclic carbocyclyl. In certain embodiments, at least one instance of $R^B$ is 3- to 7-membered, monocyclic carbocyclyl. In certain embodiments, at least one instance of $R^B$ is cylcopropyl. In certain embodiments, at least one instance of $R^B$ is cyclobutyl, cyclopentyl, cyclohexyl, or cycloheptyl. In certain embodiments, at least one instance of $R^B$ is bicyclic carbocyclyl. In certain embodiments, at least one instance of $R^B$ is 5- to 13-membered, bicyclic carbocyclyl. In certain embodiments, at least one instance of $R^B$ is substituted heterocyclyl. In certain embodiments, at least one instance of $R^B$ is unsubstituted heterocyclyl. In certain embodiments, at least one instance of $R^B$ is saturated heterocyclyl. In certain embodiments, at least one instance of $R^B$ is unsaturated heterocyclyl. In certain embodiments, at least one instance of $R^B$ is heterocyclyl including one, two, or three double bonds in the heterocyclic ring. In certain embodiments, at least one instance of $R^B$ is heterocyclyl, wherein one, two, or three atoms in the heterocyclic ring are independently selected from the group consisting of nitrogen, oxygen, and sulfur. In certain embodiments, at least one instance of $R^B$ is monocyclic heterocyclyl. In certain embodiments, at least one instance of $R^B$ is 3- to 7-membered, monocyclic heterocyclyl. In certain embodiments, at least one instance of $R^B$ is bicyclic heterocyclyl. In certain embodiments, at least one instance of $R^B$ is 5- to 13-membered, bicyclic heterocyclyl. In certain embodiments, at least one instance of $R^B$ is substituted aryl. In certain embodiments, at least one instance of $R^B$ is unsubstituted aryl. In certain embodiments, at least one instance of $R^B$ is 6- to 14-membered aryl. In certain embodiments, at least one instance of $R^B$ is 6- to 10-membered aryl. In certain embodiments, at least one instance of $R^B$ is substituted phenyl. In certain embodiments, at least one instance of $R^B$ is unsubstituted phenyl. In certain embodiments, at least one instance of $R^B$ is substituted naphthyl. In certain embodiments, at least one instance of $R^B$ is unsubstituted naphthyl. In certain embodiments, at least one instance of $R^B$ is substituted heteroaryl. In certain embodiments, at least one instance of $R^B$ is unsubstituted heteroaryl. In certain embodiments, at least one instance of $R^B$ is heteroaryl, wherein one, two, three, or four atoms in the heteroaryl ring are independently selected from the group consisting of nitrogen, oxygen, and sulfur. In certain embodiments, at least one instance of $R^B$ is monocyclic heteroaryl. In certain embodiments, at least one instance of $R^B$ is 5-membered, monocyclic heteroaryl. In certain embodiments, at least one instance of $R^B$ is 6-membered, monocyclic heteroaryl. In certain embodiments, at least one instance of $R^B$ is pyridyl. In certain embodiments, at least one instance of $R^B$ is bicyclic heteroaryl, wherein the point of attachment may be on any atom of the bicyclic heteroaryl ring system, as valency permits. In certain embodiments, at least one instance of $R^B$ is 9-membered, bicyclic heteroaryl. In certain embodiments, at least one instance of $R^B$ is 10-membered, bicyclic heteroaryl. In certain embodiments, at least one instance of $R^B$ is $OR^{B1}$. In certain embodiments, at least one instance of $R^B$ is OMe. In certain embodiments, at least one instance of $R^B$ is OEt. In certain embodiments, at least one instance of $R^B$ is —OPr, —OBu, —O(pentyl), or —O(hexyl). In certain embodiments, at least one instance of $R^B$ is —OPh. In certain embodiments, at least one instance of $R^B$ is OBn. In certain embodiments, at least one instance of $R^B$ is —OH. In certain embodiments, at least one instance of $R^B$ is —$SR^{B1}$. In certain embodiments, at least one instance of $R^B$ is SMe. In certain embodiments, at least one instance of $R^B$ is —SH. In certain embodiments, at least one instance of $R^B$ is —$N(R^{B1})_2$. In certain embodiments, at least one instance of $R^B$ is $NMe_2$. In certain embodiments, at least one instance of $R^B$ is —$NH_2$. In certain embodiments, at least one instance of $R^B$ is —CN. In certain embodiments, at least one instance of $R^B$ is —SCN. In certain embodiments, at least one instance of $R^B$ is —$C(=NR^{B1})R^{B1}$, —$C(=NR^{B1})OR^{B1}$, or —$C(=NR^{B1})N(R^{B1})_2$. In certain embodiments, at least one instance of $R^B$ is —$C(=O)R^{B1}$, —$C(=O)OR^{B1}$, or —$C(=O)N(R^{B1})_2$. In certain embodiments, at least one instance of $R^B$ is —$NO_2$. In certain embodiments, at least one instance of $R^B$ is —$NR^{B1}C(=O)R^{B1}$, —$NR^{B1}C(=O)OR^{B1}$, or —$NR^{B1}C(=O)N(R^{B1})_2$. In certain embodiments, at least one instance of $R^B$ is —OC$(=O)R^{B1}$, —$OC(=O)OR^{B1}$ or —$OC(=O)N(R^{B1})_2$.

In compounds of Formula (I) or (II), two $R^B$ groups may be joined to form a substituted or unsubstituted carbocyclic ring. In certain embodiments, two instances of $R^B$ are joined to form a saturated or unsaturated carbocyclic ring. In certain embodiments, two instances of $R^B$ are joined to form a carbocyclic ring including one, two, or three double bonds in the carbocyclic ring. In certain embodiments, two instances of $R^B$ are joined to form a 3- to 7-membered, monocyclic carbocyclic ring. In certain embodiments, two instances of $R^B$ are joined to form a 3-membered carbocyclic ring (e.g., cyclopropyl ring).

In certain embodiments, two instances of $R^B$ are joined to form a substituted or unsubstituted heterocyclic ring. In certain embodiments, two instances of $R^B$ are joined to form a saturated or unsaturated heterocyclic ring. In certain embodiments, two instances of $R^B$ are joined to form a heterocyclic ring including one, two, or three double bonds in the heterocyclic ring. In certain embodiments, two instances of $R^B$ are joined to form a heterocyclic ring, wherein one, two, or three atoms in the heterocyclic ring are independently selected from the group consisting of nitrogen, oxygen, and sulfur. In certain embodiments, two instances of $R^B$ are joined to form a 3- to 7-membered, monocyclic heterocyclic ring. In certain embodiments, two instances of $R^B$ are joined to form a 5- to 13-membered, bicyclic heterocyclic ring.

In certain embodiments, two instances of $R^B$ are joined to form a substituted or unsubstituted aryl ring. In certain embodiments, two instances of $R^B$ are joined to form a 6- to 14-membered aryl ring. In certain embodiments, two instances of $R^B$ are joined to form a 6- to 10-membered aryl ring. In certain embodiments, two instances of $R^B$ are joined to form a monocyclic aryl ring. In certain embodiments, two instances of $R^B$ are joined to form a phenyl. In certain embodiments, two instances of $R^B$ are joined to form a bicyclic aryl ring. In certain embodiments, two instances of $R^B$ are joined to form a naphthyl.

In certain embodiments, two instances of $R^B$ are joined to form a substituted or unsubstituted heteroaryl ring. In certain embodiments, two instances of $R^B$ are joined to form a monocyclic heteroaryl ring, wherein one, two, or three atoms in the heteroaryl ring are independently selected from the group consisting of nitrogen, oxygen, and sulfur. In certain embodiments, two instances of $R^B$ are joined to form a 5-membered, monocyclic heteroaryl ring. In certain embodiments, two instances of $R^B$ are joined to form a 6-membered, monocyclic heteroaryl ring. In certain embodiments, two instances of $R^B$ are joined to form a pyridyl. In certain embodiments, two instances of $R^B$ are joined to form a bicyclic heteroaryl ring, wherein one, two, three, or four atoms in the heteroaryl ring are independently selected from the group consisting of nitrogen, oxygen, and sulfur. In certain embodiments, two instances of $R^B$ are joined to form a 9-membered, bicyclic heteroaryl ring. In certain embodiments, two instances of $R^B$ are joined to form a 10-membered, bicyclic heteroaryl ring.

In certain embodiments, at least one instance of $R^B$ is halogen, substituted or unsubstituted alkyl, or $OR^{B1}$. In certain embodiments, at least one instance of $R^B$ is halogen, unsubstituted $C_{1-6}$ alkyl, $C_{1-6}$ alkyl substituted with one or more substituents independently selected from the group consisting of halogen and —O(unsubstituted $C_{1-6}$ alkyl), or —$OR^{B1}$, wherein $R^{B1}$ is hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl).

In certain embodiments, at least one instance of $R^{B1}$ is H. In certain embodiments, at least one instance of $R^{B1}$ is substituted acyl. In certain embodiments, at least one instance of $R^{B1}$ is unsubstituted acyl. In certain embodiments, at least one instance of $R^{B1}$ is acetyl. In certain embodiments, at least one instance of $R^{B1}$ is substituted alkyl. In certain embodiments, at least one instance of $R^{B1}$ is unsubstituted alkyl. In certain embodiments, at least one instance of $R^{B1}$ is $C_{1-12}$ alkyl. In certain embodiments, at least one instance of $R^{B1}$ is $C_{1-6}$ alkyl. In certain embodiments, at least one instance of $R^{B1}$ is methyl. In certain embodiments, at least one instance of $R^{B1}$ is ethyl. In certain embodiments, at least one instance of $R^{B1}$ is propyl, butyl, pentyl, or hexyl. In certain embodiments, at least one instance of $R^{B1}$ is substituted alkenyl. In certain embodiments, at least one instance of $R^{B1}$ is unsubstituted alkenyl. In certain embodiments, at least one instance of $R^{B1}$ is vinyl. In certain embodiments, at least one instance of $R^{B1}$ is substituted alkynyl. In certain embodiments, at least one instance of $R^{B1}$ is unsubstituted alkynyl. In certain embodiments, at least one instance of $R^{B1}$ is ethynyl. In certain embodiments, at least one instance of $R^{B1}$ is substituted carbocyclyl. In certain embodiments, at least one instance of $R^{B1}$ is unsubstituted carbocyclyl. In certain embodiments, at least one instance of $R^{B1}$ is saturated carbocyclyl. In certain embodiments, at least one instance of $R^{B1}$ is unsaturated carbocyclyl. In certain embodiments, at least one instance of $R^{B1}$ is carbocyclyl including one, two, or three double bonds in the carbocyclic ring. In certain embodiments, at least one instance of $R^{B1}$ is 3- to 7-membered, monocyclic carbocyclyl. In certain embodiments, at least one instance of $R^{B1}$ is cylcopropyl. In certain embodiments, at least one instance of $R^{B1}$ is cyclobutyl, cyclopentyl, cyclohexyl, or cycloheptyl. In certain embodiments, at least one instance of $R^{B1}$ is 5- to 13-membered, bicyclic carbocyclyl. In certain embodiments, at least one instance of $R^{B1}$ is substituted heterocyclyl. In certain embodiments, at least one instance of $R^{B1}$ is unsubstituted heterocyclyl. In certain embodiments, at least one instance of $R^{B1}$ is saturated heterocyclyl. In certain embodiments, at least one instance of $R^{B1}$ is unsaturated heterocyclyl. In certain embodiments, at least one instance of $R^{B1}$ is heterocyclyl including one, two, or three double bonds in the heterocyclic ring. In certain embodiments, at least one instance of $R^{B1}$ is heterocyclyl, wherein one, two, or three atoms in the heterocyclic ring are independently selected from the group consisting of nitrogen, oxygen, and sulfur. In certain embodiments, at least one instance of $R^{B1}$ is 3- to 7-membered, monocyclic heterocyclyl. In certain embodiments, at least one instance of $R^{B1}$ is 5- to 13-membered, bicyclic heterocyclyl. In certain embodiments, at least one instance of $R^{B1}$ is substituted or unsubstituted aryl. In certain embodiments, at least one instance of $R^{B1}$ is 6- to 14-membered aryl. In certain embodiments, at least one instance of $R^{B1}$ is 6- to 10-membered aryl. In certain embodiments, at least one instance of $R^{B1}$ is monocyclic aryl. In certain embodiments, at least one instance of $R^{B1}$ is phenyl. In certain embodiments, at least one instance of $R^{B1}$ is bicyclic aryl. In certain embodiments, at least one instance of $R^{B1}$ is naphthyl. In certain embodiments, at least one instance of $R^{B1}$ is substituted or unsubstituted heteroaryl. In certain embodiments, at least one instance of $R^{B1}$ is heteroaryl, wherein one, two, three, or four atoms in the heteroaryl ring are independently selected from the group consisting of nitrogen, oxygen, and sulfur. In certain embodiments, at least one instance of $R^{B1}$ is monocyclic heteroaryl. In certain embodiments, at least one instance of $R^{B1}$ is 5-membered, monocyclic heteroaryl. In certain embodiments, at least one instance of $R^{B1}$ is 6-membered, monocyclic heteroaryl. In certain embodiments, at least one instance of $R^{B1}$ is pyridyl. In certain embodiments, at least one instance of $R^{B1}$ is bicyclic heteroaryl, wherein the point of attachment may be on any atom of the bicyclic heteroaryl ring system, as valency permits. In certain embodiments, at least one instance of $R^{B1}$ is 9-membered, bicyclic heteroaryl. In certain embodiments, at least one instance of $R^{B1}$ is 10-membered, bicyclic heteroaryl. In certain embodiments, at least one instance of $R^{B1}$ is a nitrogen protecting group when attached to a nitrogen atom. In certain embodiments, at least one instance of $R^{B1}$ is Bn, Boc, Cbz, Fmoc, trifluoroacetyl, triphenylmethyl, acetyl, or Ts when attached to a nitrogen atom. In certain embodiments, $R^{B1}$ is an oxygen protecting group when attached to an oxygen atom. In certain embodiments, $R^{B1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1}$ is a sulfur protecting group when attached to a sulfur atom. In certain embodiments, $R^{B1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{B1}$ are joined to form a substituted or unsubstituted heterocyclic ring. In certain embodiments, two instances of $R^{B1}$ are joined to form a saturated or unsaturated heterocyclic ring. In certain embodiments, two instances of $R^{B1}$ are joined to form a heterocyclic ring including one, two, or three double bonds in the heterocyclic ring. In certain embodiments, two instances of $R^{B1}$ are joined to form a heterocyclic ring, wherein one, two, or three atoms in the heterocyclic ring are independently selected from the group consisting of nitrogen, oxygen, and sulfur. In certain embodiments, two instances of $R^{B1}$ are joined to form a 3- to 7-membered, monocyclic heterocyclic ring. In certain embodiments, two instances of $R^{B1}$ are joined to form a 5- to 13-membered, bicyclic heterocyclic ring.

A compound of Formula (I) or (II) may include one or more substituents $R^C$, $R^D$, and/or $R^E$. In certain embodiments, at least one instance of $R^C$, $R^D$, and $R^E$ is H. In certain embodiments, at least one instance of $R^C$, $R^D$, and $R^E$ is halogen. In certain embodiments, at least one instance of $R^C$, $R^D$, and $R^E$ is F. In certain embodiments, at least one instance of $R^C$, $R^D$, and $R^E$ is Cl. In certain embodiments, at least one instance of $R^C$, $R^D$, and $R^E$ is Br or I (iodine). In certain embodiments, at least one instance of $R^C$, $R^D$, and $R^E$ is substituted acyl. In certain embodiments, at least one instance of $R^C$, $R^D$, and $R^E$ is unsubstituted acyl. In certain embodiments, at least one instance of $R^C$, $R^D$, and $R^E$ is substituted alkyl. In certain embodiments, at least one instance of $R^C$, $R^D$, and $R^E$ is unsubstituted alkyl. In certain embodiments, at least one instance of $R^C$, $R^D$, and $R^E$ is $C_{1-12}$ alkyl. In certain embodiments, at least one instance of $R^C$, $R^D$, and $R^E$ is $C_{1-6}$ alkyl. In certain embodiments, at least one instance of $R^C$, $R^D$, and $R^E$ is unsubstituted methyl. In certain embodiments, at least one instance of $R^C$, $R^D$, and $R^E$ is substituted methyl. In certain embodiments, at least one instance of $R^C$, $R^D$, and $R^E$ is $CH_2F$, $CHF_2$, or $CF_3$. In certain embodiments, at least one instance of $R^C$, $R^D$, and $R^E$ is Bn. In certain embodiments, at least one instance of $R^C$, $R^D$, and $R^E$ is ethyl. In certain embodiments, at least one instance of $R^C$, $R^D$, and $R^E$ is propyl, butyl, pentyl, or hexyl. In certain embodiments, at least one instance of $R^C$, $R^D$, and $R^E$ is substituted alkenyl. In certain embodiments, at least one instance of $R^C$, $R^D$, and $R^E$ is unsubstituted alkenyl. In certain embodiments, at least one instance of $R^C$, $R^D$, and $R^E$ is vinyl. In certain embodiments, at least one instance of $R^C$, $R^D$, and $R^E$ is substituted alkynyl. In certain embodiments, at least one instance of $R^C$, $R^D$, and $R^E$ is unsubstituted alkynyl. In certain embodiments, at least one instance of $R^C$, $R^D$, and $R^E$ is ethynyl. In certain embodiments, at least one instance of $R^C$, $R^D$, and $R^E$ is substituted carbocyclyl. In certain embodiments, at least one instance of $R^C$, $R^D$, and $R^E$ is unsubstituted carbocyclyl. In certain embodiments, at least one instance of $R^C$, $R^D$, and $R^E$ is saturated carbocyclyl. In certain embodiments, at least one instance of $R^C$, $R^D$, and $R^E$ is unsaturated carbocyclyl. In certain embodiments, at least one instance of $R^C$, $R^D$, and $R^E$ is carbocyclyl including one, two, or three double bonds in the carbocyclic ring. In certain embodiments, at least one instance of $R^C$, $R^D$, and $R^E$ is monocyclic carbocyclyl. In certain embodiments, at least one instance of $R^C$, $R^D$, and $R^E$ is 3- to 7-membered, monocyclic carbocyclyl. In certain embodiments, at least one instance of $R^C$, $R^D$, and $R^E$ is cylcopropyl. In certain embodiments, at least one instance of $R^C$, $R^D$, and $R^E$ is cyclobutyl, cyclopentyl, cyclohexyl, or cycloheptyl. In certain embodiments, at least one instance of $R^C$, $R^D$, and $R^E$ is bicyclic carbocyclyl. In certain embodiments, at least one instance of $R^C$, $R^D$, and $R^E$ is 5- to 13-membered, bicyclic carbocyclyl. In certain embodiments, at least one instance of $R^C$, $R^D$, and $R^E$ is substituted heterocyclyl. In certain embodiments, at least one instance of $R^C$, $R^D$, and $R^E$ is unsubstituted heterocyclyl. In certain embodiments, at least one instance of $R^C$, $R^D$, and $R^E$ is saturated heterocyclyl. In certain embodiments, at least one instance of $R^C$, $R^D$, and $R^E$ is unsaturated heterocyclyl. In certain embodiments, at least one instance of $R^C$, $R^D$, and $R^E$ is heterocyclyl including one, two, or three double bonds in the heterocyclic ring. In certain embodiments, at least one instance of $R^C$, $R^D$, and $R^E$ is heterocyclyl, wherein one, two, or three atoms in the heterocyclic ring are selected from the group consisting of nitrogen, oxygen, and sulfur. In certain embodiments, at least one instance of $R^C$, $R^D$, and $R^E$ is monocyclic heterocyclyl. In certain embodiments, at least one instance of $R^C$, $R^D$, and $R^E$ is 3- to 7-membered, monocyclic heterocyclyl. In certain embodiments, at least one instance of $R^C$, $R^D$, and $R^E$ is bicyclic heterocyclyl. In certain embodiments, at least one instance of $R^C$, $R^D$, and $R^E$ is 5- to 13-membered, bicyclic heterocyclyl. In certain embodiments, at least one instance of $R^C$, $R^D$, and $R^E$ is substituted aryl. In certain embodiments, at least one instance of $R^C$, $R^D$, and $R^E$ is unsubstituted aryl. In certain embodiments, at least one instance of $R^C$, $R^D$, and $R^E$ is 6- to 14-membered aryl. In certain embodiments, at least one instance of $R^C$, $R^D$, and $R^E$ is 6- to 10-membered aryl. In certain embodiments, at least one instance of $R^C$, $R^D$, and $R^E$ is substituted phenyl. In certain embodiments, at least one instance of $R^C$, $R^D$, and $R^E$ is unsubstituted phenyl. In certain embodiments, at least one instance of $R^C$, $R^D$, and $R^E$ is substituted naphthyl. In certain embodiments, at least one instance of $R^C$, $R^D$, and $R^E$ is unsubstituted naphthyl. In certain embodiments, at least one instance of $R^C$, $R^D$, and $R^E$ is substituted heteroaryl. In certain embodiments, at least one instance of $R^C$, $R^D$, and $R^E$ is unsubstituted heteroaryl. In certain embodiments, at least one instance of $R^C$, $R^D$, and $R^E$ is heteroaryl, wherein one, two, three, or four atoms in the heteroaryl ring are selected from the group consisting of nitrogen, oxygen, and sulfur. In certain embodiments, at least one instance of $R^C$, $R^D$, and $R^E$ is monocyclic heteroaryl. In certain embodiments, at least one instance of $R^C$, $R^D$, and $R^E$ is 5-membered, monocyclic heteroaryl. In certain embodiments, at least one instance of $R^C$, $R^D$, and $R^E$ is 6-membered, monocyclic heteroaryl. In certain embodiments, at least one instance of $R^C$, $R^D$, and $R^E$ is pyridyl. In certain embodiments, at least one instance of $R^C$, $R^D$, and $R^E$ is bicyclic heteroaryl, wherein the point of attachment may be on any atom of the bicyclic heteroaryl ring system, as valency permits. In certain embodiments, at least one instance of $R^C$, $R^D$, and $R^E$ is 9-membered, bicyclic heteroaryl. In certain embodiments, at least one instance of $R^C$, $R^D$, and $R^E$ is 10-membered, bicyclic heteroaryl. In certain embodiments, at least one instance of $R^C$, $R^D$, and $R^E$ is —$OR^{C1}$. In certain embodiments, at least one instance of $R^C$, $R^D$, and $R^E$ is —OMe. In certain embodiments, at least one instance of $R^C$, $R^D$, and $R^E$ is —OEt. In certain embodiments, at least one instance of $R^C$, $R^D$, and $R^E$ is —OPr, —OBu, —O(pentyl), or —O(hexyl). In certain embodiments, at least one instance of $R^C$, $R^D$, and $R^E$ is —OPh. In certain embodiments, at least one instance of $R^C$, $R^D$, and $R^E$ is OBn. In certain embodiments, at least one instance of $R^C$, $R^D$, and $R^E$ is OH. In certain embodiments, at least one instance of $R^C$, $R^D$, and $R^E$ is $SR^{C1}$. In certain embodiments, at least one instance of $R^C$, $R^D$, and $R^E$ is SMe. In certain embodiments, at least one instance of $R^C$, $R^D$, and $R^E$ is —SH. In certain embodiments, at least one instance of $R^C$, $R^D$, and $R^E$ is $N(R^{C1})_2$. In certain embodiments, at least one instance of $R^C$, $R^D$, and $R^E$ is $NMe_2$. In certain embodiments, at least one instance of $R^C$, $R^D$, and $R^E$ is —$NH_2$. In certain embodiments, at least one instance of $R^C$, $R^D$, and $R^E$ is —CN. In certain embodiments, at least one instance of $R^C$, $R^D$, and $R^E$ is SCN. In certain embodiments, at least one instance of $R^C$, $R^D$, and $R^E$ is —C(=$NR^{C1}$)$R^{C1}$, —C(=$NR^{C1}$)$OR^{C1}$, or —C(=$NR^{C1}$)N($R^{C1}$)$_2$. In certain embodiments, at least one instance of $R^C$, $R^D$, and $R^E$ is —C(=O)$R^{C1}$, —C(=O)$OR^{C1}$, or —C(=O)N($R^{C1}$)$_2$. In certain embodiments, at least one instance of $R^C$, $R^D$, and $R^E$ is —$NO_2$. In certain embodiments, at least one instance of $R^C$, $R^D$, and $R^E$ is —$NR^{C1}$C(=O)$R^{C1}$, —$NR^{C1}$C(=O)$OR^{C1}$, or —$NR^{C1}$C(=O)N($R^{C1}$)$_2$. In certain embodiments, at least one instance of $R^C$, $R^D$, and $R^E$ is —OC(=O)$R^{C1}$, —OC(=O)$OR^{C1}$, or —OC(=O)N($R^{C1}$)$_2$.

In certain embodiments, at least one instance of $R^C$, $R^D$, and $R^E$ is halogen, substituted or unsubstituted alkyl, or $OR^{C1}$. In certain embodiments, at least one instance of $R^C$, $R^D$, and $R^E$ is halogen, unsubstituted $C_{1-6}$ alkyl, $C_{1-6}$ alkyl substituted with one or more substituents independently selected from the group consisting of halogen and —O(unsubstituted $C_{1-6}$ alkyl), or —$OR^{C1}$, wherein $R^{C1}$ is hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl).

In compounds of Formula (I), $R^C$ and $R^D$ may be joined to form a substituted or unsubstituted, monocyclic carbocyclic ring. In certain embodiments, $R^C$ and $R^D$ are joined to form a saturated or unsaturated carbocyclic ring. In certain embodiments, $R^C$ and $R^D$ are joined to form a carbocyclic ring including one, two, or three double bonds in the carbocyclic ring. In certain embodiments, $R^C$ and $R^D$ are joined to form a 3- to 7-membered carbocyclic ring. In certain embodiments, $R^C$ and $R^D$ are joined to form a 6-membered carbocyclic ring. In certain embodiments, when $R^C$ and $R^D$ are joined to form a substituted monocyclic carbocyclic ring, the carbocyclic ring formed by joining $R^C$ and $R^D$ is substituted with one or more substituents $R^{D1}$, wherein each instance of $R^{D1}$ is independently selected from the group consisting of halogen, unsubstituted $C_{1-6}$ alkyl, $C_{1-6}$ alkyl substituted with one or more substituents independently selected from the group consisting of halogen and —O(unsubstituted $C_{1-6}$ alkyl), or —$OR^{D1a}$, wherein —$R^{D1a}$ is hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl). In certain embodiments, when $R^C$ and $R^D$ are joined to form a substituted or unsubstituted, monocyclic carbocyclic ring, Ring B includes the substituted or unsubstituted, monocyclic carbocyclic ring formed by joining $R^C$ and $R^D$ to form a bicyclic ring.

In compounds of Formula (I), $R^D$ and $R^E$ may be joined to form a substituted or unsubstituted, monocyclic or bicyclic carbocyclic ring. In certain embodiments, $R^D$ and $R^E$ are joined to form a saturated or unsaturated carbocyclic ring. In certain embodiments, $R^D$ and $R^E$ are joined to form a carbocyclic ring including one, two, or three double bonds in the carbocyclic ring. In certain embodiments, $R^D$ and $R^E$ are joined to form a 3- to 7-membered, monocyclic carbocyclic ring. In certain embodiments, $R^D$ and $R^E$ are joined to form a 6-membered, monocyclic carbocyclic ring. In certain embodiments, $R^D$ and $R^E$ are joined to form a 7- to 13-membered, bicyclic carbocyclic ring. In certain embodiments, $R^D$ and $R^E$ are joined to form a 9-membered, bicyclic carbocyclic ring. In certain embodiments, $R^D$ and $R^E$ are joined to form a 10-membered, bicyclic carbocyclic ring. In certain embodiments, when $R^D$ and $R^E$ are joined to form a substituted carbocyclic ring, the carbocyclic ring formed by joining $R^D$ and $R^E$ is substituted with one or more substituents $R^{E1}$, wherein each instance of $R^{E1}$ is independently selected from the group consisting of halogen, unsubstituted $C_{1-6}$ alkyl, $C_{1-6}$ alkyl substituted with one or more substituents independently selected from the group consisting of halogen and —O(unsubstituted $C_{1-6}$ alkyl), or $OR^{E1a}$, wherein $R^{E1a}$ is hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl).

In certain embodiments, when $R^C$ and $R^D$ are joined to form a substituted or unsubstituted, monocyclic carbocyclic ring, and when $R^D$ and $R^E$ are joined to form a substituted or unsubstituted, monocyclic or bicyclic carbocyclic ring, Ring B includes the substituted or unsubstituted, monocyclic carbocyclic ring formed by joining $R^C$ and $R^D$ and includes the substituted or unsubstituted, monocyclic or bicyclic carbocyclic carbocyclic ring formed by joining $R^D$ and $R^E$ to form a tricyclic or tetracyclic ring.

In certain embodiments, at least one instance of $R^{C1}$ is H. In certain embodiments, at least one instance of $R^{C1}$ is substituted acyl. In certain embodiments, at least one instance of $R^{C1}$ is unsubstituted acyl. In certain embodiments, at least one instance of $R^{C1}$ is acetyl. In certain embodiments, at least one instance of $R^{C1}$ is substituted alkyl. In certain embodiments, at least one instance of $R^{C1}$ is unsubstituted alkyl. In certain embodiments, at least one instance of $R^{C1}$ is $C_{1-12}$ alkyl. In certain embodiments, at least one instance of $R^{C1}$ is $C_{1-6}$ alkyl. In certain embodiments, at least one instance of $R^{C1}$ is methyl. In certain embodiments, at least one instance of $R^{C1}$ is ethyl. In certain embodiments, at least one instance of $R^{C1}$ is propyl, butyl, pentyl, or hexyl. In certain embodiments, at least one instance of $R^{C1}$ is substituted alkenyl. In certain embodiments, at least one instance of $R^{C1}$ is unsubstituted alkenyl. In certain embodiments, at least one instance of $R^{C1}$ is vinyl. In certain embodiments, at least one instance of $R^{C1}$ is substituted alkynyl. In certain embodiments, at least one instance of $R^{C1}$ is unsubstituted alkynyl. In certain embodiments, at least one instance of $R^{C1}$ is ethynyl. In certain embodiments, at least one instance of $R^{C1}$ is substituted carbocyclyl. In certain embodiments, at least one instance of $R^{C1}$ is unsubstituted carbocyclyl. In certain embodiments, at least one instance of $R^{C1}$ is saturated carbocyclyl. In certain embodiments, at least one instance of $R^{C1}$ is unsaturated carbocyclyl. In certain embodiments, at least one instance of $R^{C1}$ is carbocyclyl including one, two, or three double bonds in the carbocyclic ring. In certain embodiments, at least one instance of $R^{C1}$ is 3- to 7-membered, monocyclic carbocyclyl. In certain embodiments, at least one instance of $R^{C1}$ is cylcopropyl. In certain embodiments, at least one instance of $R^{C1}$ is cyclobutyl, cyclopentyl, cyclohexyl, or cycloheptyl. In certain embodiments, at least one instance of $R^{C1}$ is 5- to 13-membered, bicyclic carbocyclyl. In certain embodiments, at least one instance of $R^{C1}$ is substituted heterocyclyl. In certain embodiments, at least one instance of $R^{C1}$ is unsubstituted heterocyclyl. In certain embodiments, at least one instance of $R^{C1}$ is saturated heterocyclyl. In certain embodiments, at least one instance of $R^{C1}$ is unsaturated heterocyclyl. In certain embodiments, at least one instance of $R^{C1}$ is heterocyclyl including one, two, or three double bonds in the heterocyclic ring. In certain embodiments, at least one instance of $R^{C1}$ is heterocyclyl, wherein one, two, or three atoms in the heterocyclic ring are independently selected from the group consisting of nitrogen, oxygen, and sulfur. In certain embodiments, at least one instance of $R^{C1}$ is 3- to 7-membered, monocyclic heterocyclyl. In certain embodiments, at least one instance of $R^{C1}$ is 5- to 13-membered, bicyclic heterocyclyl. In certain embodiments, at least one instance of $R^{C1}$ is substituted or unsubstituted aryl. In certain embodiments, at least one instance of $R^{C1}$ is 6- to 14-membered aryl. In certain embodiments, at least one instance of $R^{C1}$ is 6- to 10-membered aryl. In certain embodiments, at least one instance of $R^{C1}$ is monocyclic aryl. In certain embodiments, at least one instance of $R^{C1}$ is phenyl. In certain embodiments, at least one instance of $R^{C1}$ is bicyclic aryl. In certain embodiments, at least one instance of $R^{C1}$ is naphthyl. In certain embodiments, at least one instance of $R^{C1}$ is substituted or unsubstituted heteroaryl. In certain embodiments, at least one instance of $R^{C1}$ is heteroaryl, wherein one, two, three, or four atoms in the heteroaryl ring are independently selected from the group consisting of nitrogen, oxygen, and sulfur. In certain embodiments, at least one instance of $R^{C1}$ is monocyclic heteroaryl. In certain embodiments, at least one instance of $R^{C1}$ is 5-membered, monocyclic heteroaryl. In certain embodiments, at least one instance of $R^{C1}$ is 6-membered, monocyclic heteroaryl. In certain embodiments, at least one instance of $R^{C1}$ is pyridyl. In certain embodiments, at least one instance of $R^{C1}$ is bicyclic heteroaryl, wherein the point of attachment may be on any atom of the bicyclic heteroaryl ring system, as valency permits. In certain embodiments, at least one instance of $R^{C1}$ is 9-membered, bicyclic heteroaryl. In certain embodiments, at least one instance of $R^{C1}$ is 10-membered, bicyclic heteroaryl. In certain embodiments, at least one instance of $R^{C1}$ is a nitrogen protecting group when attached to a nitrogen atom. In certain embodiments, at least one instance of $R^{C1}$ is Bn, Boc, Cbz, Fmoc, trifluoroacetyl, triphenylmethyl, acetyl, or Ts when attached to a nitrogen atom. In certain embodiments, at least one instance of $R^{C1}$ is an oxygen protecting group when attached to an oxygen atom. In certain embodiments, at least one instance of $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one instance of $R^{C1}$ is a sulfur protecting group when attached to a sulfur atom. In certain embodiments, at least one instance of $R^{C1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{C1}$ are joined to form a substituted or unsubstituted heterocyclic ring. In certain embodiments, two instances of $R^{C1}$ are joined to form a saturated or unsaturated heterocyclic ring. In certain embodiments, two instances of $R^{C1}$ are joined to form a heterocyclic ring including one, two, or three double bonds in the heterocyclic ring. In certain embodiments, two instances of $R^{C1}$ are joined to form a heterocyclic ring, wherein one, two, or three atoms in the heterocyclic ring are independently selected from the group consisting of nitrogen, oxygen, and sulfur. In certain embodiments, two instances of $R^{C1}$ are joined to form a 3- to 7-membered, monocyclic heterocyclic ring. In certain embodiments, two instances of $R^{C1}$ are joined to form a 5- to 13-membered, bicyclic heterocyclic ring.

In certain embodiments, the compound of Formula (I) is of the formula:

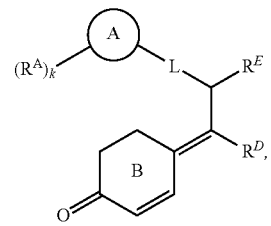

or a pharmaceutically acceptable salt, hydrate, solvate, polymorph, co-crystal, tautomer, or isotopically labeled derivative thereof.

In certain embodiments, the compound of Formula (I) is of the formula:

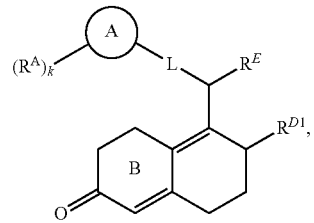

or a pharmaceutically acceptable salt, hydrate, solvate, polymorph, co-crystal, tautomer, or isotopically labeled derivative thereof.

In certain embodiments, the compound of Formula (I) is of the formula:

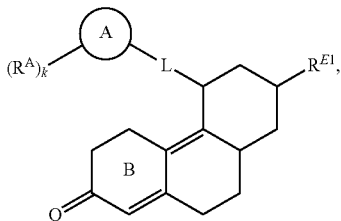

or a pharmaceutically acceptable salt, hydrate, solvate, polymorph, co-crystal, tautomer, or isotopically labeled derivative thereof.

In certain embodiments, the compound of Formula (I) is of the formula:

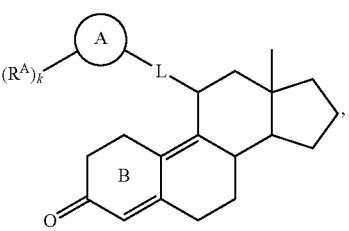

or a pharmaceutically acceptable salt, hydrate, solvate, polymorph, co-crystal, tautomer, or isotopically labeled derivative thereof.

In certain embodiments, the compound of Formula (I) is of the formula:

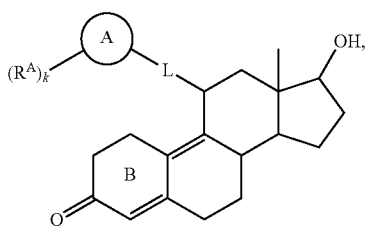

or a pharmaceutically acceptable salt, hydrate, solvate, polymorph, co-crystal, tautomer, or isotopically labeled derivative thereof.

In certain embodiments, the compound of Formula (I) is of the formula:

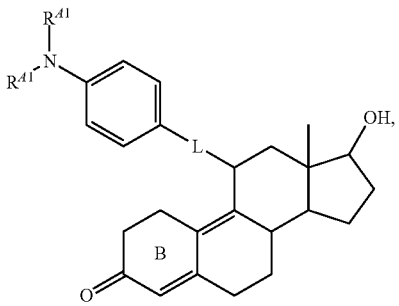

or a pharmaceutically acceptable salt, hydrate, solvate, polymorph, co-crystal, tautomer, or isotopically labeled derivative thereof.

In certain embodiments, the compound of Formula (I) is of the formula:

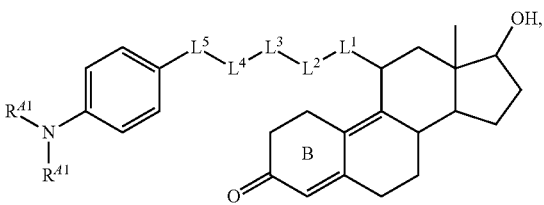

or a pharmaceutically acceptable salt, hydrate, solvate, polymorph, co-crystal, tautomer, or isotopically labeled derivative thereof.

In certain embodiments, the compound of Formula (I) is of the formula:

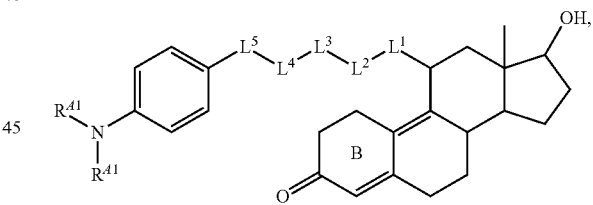

or a pharmaceutically acceptable salt, hydrate, solvate, polymorph, co-crystal, tautomer, or isotopically labeled derivative thereof, wherein:

each instance of $R^{A1}$ is independently unsubstituted $C_{1-6}$ alkyl or $C_{1-6}$ alkyl substituted with one or more substituents independently selected from the group consisting of halogen and —O(unsubstituted $C_{1-6}$ alkyl);

$L^1$, $L^3$, and $L^5$ are independently an unsubstituted $C_{1-8}$ hydrocarbon chain or a $C_{1-8}$ hydrocarbon chain substituted with one or more substituents independently selected from the group consisting of halogen and —O(unsubstituted $C_{1-6}$ alkyl); and $L^2$ and $L^4$ are independently —$NR^L$—, —$NR^LC(=O)O$—, or —$OC(=O)NR^L$—, wherein each instance of $R^L$ is independently hydrogen, unsubstituted $C_{1-6}$ alkyl, or $C_{1-6}$ alkyl substituted with one or more substituents independently selected from the group consisting of halogen and —O(unsubstituted $C_{1-6}$ alkyl).

In certain embodiments, the compound of Formula (I) is of the formula:
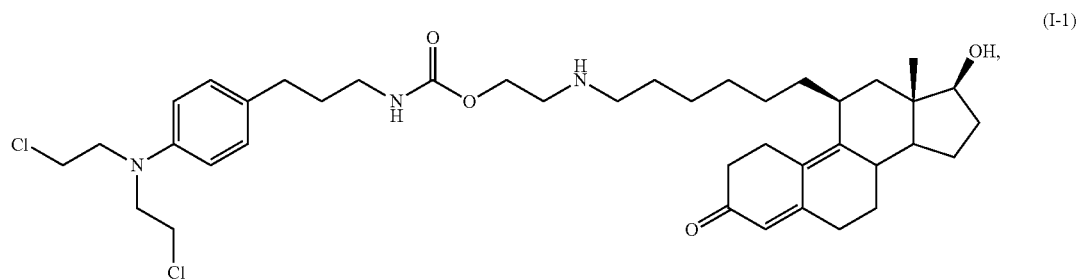
(I-1)
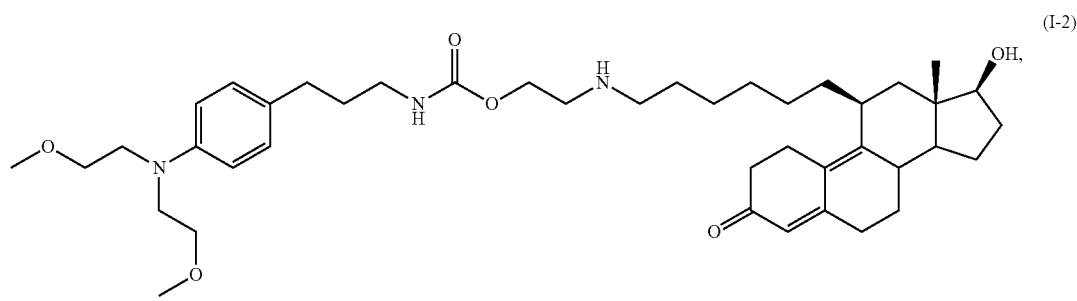
(I-2)
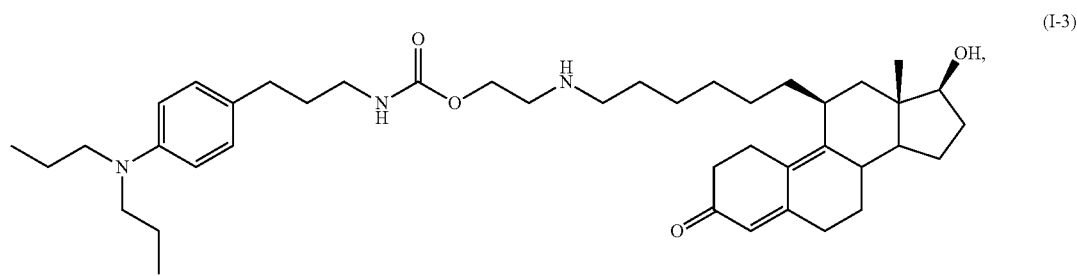
(I-3)
or a pharmaceutically acceptable salt, hydrate, solvate, polymorph, co-crystal, tautomer, or isotopically labeled derivative thereof.
In certain embodiments, the compound of Formula (I) is of the formula:
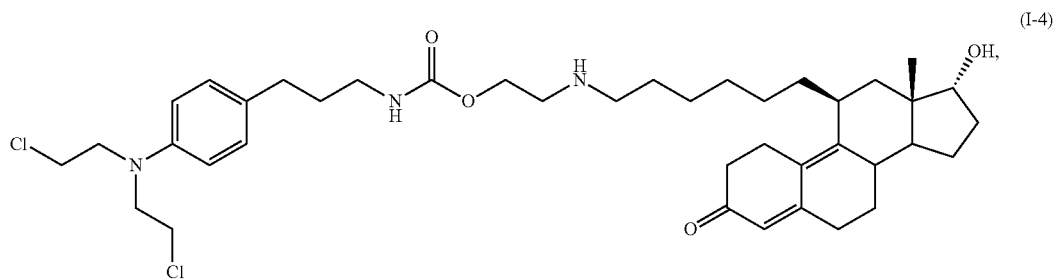 [SMILES: C[C@]12C[C@H](CCCCCCNCCOC(=O)NCCCc3ccc(N(CCCl)CCCl)cc3)C3=C4CCC(=O)C=C4CCC3C1CC[C@H]2O]
(I-4)

In certain embodiments, the compound of Formula (I) is of the formula:

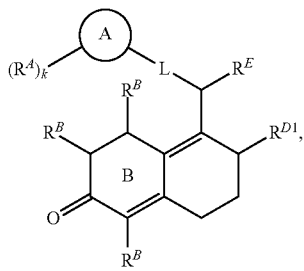

or a pharmaceutically acceptable salt, hydrate, solvate, polymorph, co-crystal, tautomer, or isotopically labeled derivative thereof.

In certain embodiments, the compound of Formula (I) is of the formula:

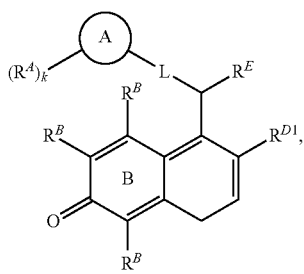

or a pharmaceutically acceptable salt, hydrate, solvate, polymorph, co-crystal, tautomer, or isotopically labeled derivative thereof.

In certain embodiments, the compound of Formula (I) is of the formula:

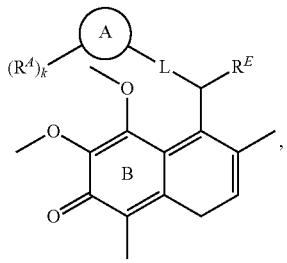

or a pharmaceutically acceptable salt, hydrate, solvate, polymorph, co-crystal, tautomer, or isotopically labeled derivative thereof.

In certain embodiments, the compound of Formula (II) is of the formula:

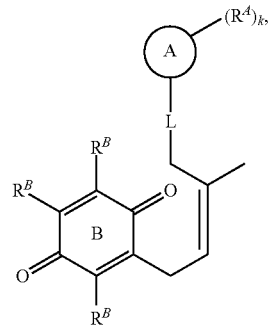

or a pharmaceutically acceptable salt, hydrate, solvate, polymorph, co-crystal, tautomer, or isotopically labeled derivative thereof.

In certain embodiments, the compound of Formula (II) is of the formula:

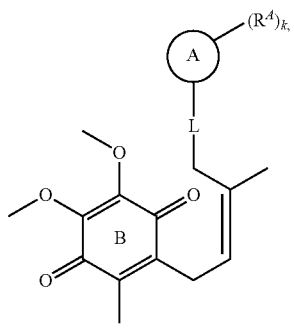

or a pharmaceutically acceptable salt, hydrate, solvate, polymorph, co-crystal, tautomer, or isotopically labeled derivative thereof.

In certain embodiments, the compound of Formula (I) is a ubiquinone (shown below)

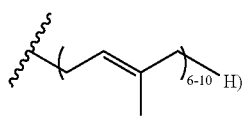

derivative. Ubiquinone uses the hydrophobic tail (e.g., to reside in the mitochondrial inner membrane. The quinone moiety of ubiquinone is a redox-active moiety. In certain embodiments, the compound of Formula (I) is substituted ubiquinone. In certain embodiments, the compound of Formula (I) is an electron carrier. Ring B (including the optional substituents on Ring B) of a compound of Formula (I) may be a redox-active moiety, and L and/or Ring A (including the optional substituents on Ring A) may be hydrophobic. In certain embodiments, the compound of Formula (I) competes with ubiquinone as an electron carrier from enzyme complex I and/or enzyme complex II to complex III. In certain embodiments, Ring B is electron deficient. In certain embodiments, at least one substituent (e.g., at least one instance of $R^B$, $R^C$, $R^{D1}$, or $R^{E1}$) on Ring B is an electron withdrawing group.

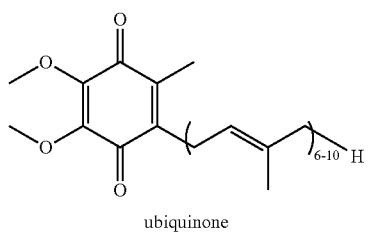

ubiquinone

In certain embodiments, the compounds of the invention are compounds of Formula (I), and pharmaceutically acceptable salts and stereoisomers thereof. In certain embodiments, the compounds of the invention are compounds of Formula (I), and pharmaceutically acceptable salts thereof. In certain embodiments, a compound of Formula (I) is a mixture of stereoisomers. In certain embodiments, a compound of Formula (I) is a racemic mixture of stereoisomers. In certain embodiments, a compound of Formula (I) is a substantially pure stereoisomer. In certain embodiments, the compounds of the invention are compounds of Formula (II), and pharmaceutically acceptable salts and stereoisomers thereof. In certain embodiments, the compounds of the invention are compounds of Formula (II), and pharmaceutically acceptable salts thereof. In certain embodiments, a compound of Formula (II) is a mixture of stereoisomers. In certain embodiments, a compound of Formula (II) is a racemic mixture of stereoisomers. In certain embodiments, a compound of Formula (II) is a substantially pure stereoisomer. In certain embodiments, a compound of the invention is not a compound of Formula (I-1), (I-2), or (I-3), or a pharmaceutically acceptable salt, hydrate, solvate, polymorph, co-crystal, tautomer, or isotopically labeled derivative thereof. In certain embodiments, a compound of the invention is not a compound of Formula (I-1), (I-2), (I-3), or (I-4), or a pharmaceutically acceptable salt, hydrate, solvate, polymorph, co-crystal, tautomer, or isotopically labeled derivative thereof.

Pharmaceutical Compositions, Kits, and Administration

The present invention provides pharmaceutical compositions comprising a compound described herein (e.g., a compound of Formula (I) or (II), or a pharmaceutically acceptable salt, solvate, hydrate, polymorph, co-crystal, tautomer, stereoisomer, or isotopically labeled derivative thereof), and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the pharmaceutical composition of the invention comprises a compound of Formula (I), or a pharmaceutically acceptable salt thereof, and a pharmaceutically acceptable excipient. In certain embodiments, the pharmaceutical composition of the invention comprises the compound of Formula (II), or a pharmaceutically acceptable salt thereof, and optionally a pharmaceutically acceptable excipient. In certain embodiments, the pharmaceutical composition of the invention comprises the compound of Formula (II), or a pharmaceutically acceptable salt thereof, and a pharmaceutically acceptable excipient. In certain embodiments, a pharmaceutical composition of the invention does not include a compound of Formula (I-1), (I-2), or (I-3).

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing polycystic kidney disease (PKD) or polycystic liver disease (PLD). In certain embodiments, the effective amount is an amount effective for treating PKD (e.g., ADPKD or ARPKD). In certain embodiments, the effective amount is an amount effective for treating PLD (e.g., ADPLD or ARPLD). An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, German® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound of this invention may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition of the invention is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating PKD or PLD), bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, an inventive pharmaceutical composition including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, anti-diabetic agents, anti-allergic agents, and pain-relieving agents.

In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the additional pharmaceutical agent is a mitochondrial respiration inhibitor (e.g., a complex 1 inhibitor), an oxidative-stress inducer, an mTOR (mammalian target of rapamycin) inhibitor, or an activator of unfolded protein response (UPR). In certain embodiments, the inventive compounds or pharmaceutical compositions can be administered in combination with an anti-cancer therapy including, but not limited to, surgery, radiation therapy, and chemotherapy.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, or isotopically labeled derivative thereof, or a pharmaceutical composition thereof. In certain embodiments, the kits are useful for treating and/or preventing PKD or PLD in a subject in need thereof. In certain embodiments, the kits are useful for treating PKD (e.g., ADPKD or ARPKD) or PLD (ADPLD or ARPLD) in a subject in need thereof. In certain embodiments, the kits are useful for screening a library of compounds to identify a compound that is useful in the methods of the invention (e.g., useful for treating PKD or PLD). In certain embodiments, the kits further include instructions for administering the compound or pharmaceutical composition of the invention. The kits may also include information as required by a regulatory agency such as the U.S. Food and Drug Administration (FDA). In certain embodiments, the information included in the kits is prescribing information. In certain embodiments, the kits and instructions provide for treating and/or preventing PKD or PLD in a subject in need thereof. In certain embodiments, the kits and instructions provide for treating PKD (e.g., ADPKD or ARPKD) or PLD (ADPLD or ARPLD) in a subject in need thereof. In certain embodiments, the kits and instructions provide for inhibiting the growth of a cyst cell (e.g., a cyst cell causing PKD or PLD). In certain embodiments, the kits and instructions provide for killing a cyst cell (e.g., a cyst cell causing PKD or PLD). In certain embodiments, the kits and instructions provide for screening a library of compounds to identify a compound that is useful in the methods of the invention (e.g., useful for treating PKD or PLD). The kit of the invention may include one or more additional pharmaceutical agents described herein as a separate composition.

Methods of Treatment and Uses

Another aspect of the present invention relates to methods of using the compounds, pharmaceutical compositions, and kits described herein, in treating and/or preventing polycystic kidney disease (PKD) or polycystic liver disease (PLD), in inhibiting the growth of a cyst cell, and in killing a cyst cell.

There have been a number of approaches used to define the cellular pathways associated with PKD, such as ADPKD. The role of polycystin-2 (PC2) as a calcium channel and of polycystin-1 (PC1) as a receptor regulating its activity has led to a focus on calcium in the cellular ADPKD phenotype. Direct assessment of any calcium effects in the cilia compartment has been limited, but studies examining total cellular calcium have provided some insights. As a member of the TRP family of ion channel proteins abundantly expressed in the endoplasmic reticulum (ER), functional studies showed that PC2 over-expression enhances the release of $Ca^{2+}$ from intracellular stores (Koulen P, Cai Y, Geng L, Maeda Y, Nishimura S, Witzgall R, Ehrlich B E, Somlo S. Polycystin-2 is an intracellular calcium release channel. Nat. Cell Biol 2002; 4:191-197). PC2 associates with a number of $Ca^{2+}$ channel proteins (TRPC1 and TRPV4) and homo-multimerizes with itself via its C-terminus (Qian F, Germino F J, Cai Y, Zhang X, Somlo S, Germino G G. PKD1 interacts with PKD2 through a probable coiled-coil domain. Nat. Genet 1997; 16:179-183; Kottgen M, Buchholz B, Garcia-Gonzalez M A, Kotsis F, Fu X, Doerken M, Boehlke C, Stall D, Tauber R, Wegierski T, et al. TRPP2 and TRPV4 form a polymodal sensory channel complex. J. Cell Biol 2008; 182:437-447; Tsiokas L, Arnould T, Zhu C, Kim E, Walz G, Sukhatme V P. Specific association of the gene product of PKD2 with the TRPC1 channel. Proc. Natl. Acad. Sci. U.S.A 1999; 96:3934-3939; Zhang P, Luo Y, Chasan B, Gonzalez-Perrett S, Montalbetti N, Timpanaro G A, Cantero M R, Ramos A J, Goldmann W H, Zhou J, et al. The multimeric structure of polycystin-2 (TRPP2): structuralfunctional correlates of homo- and hetero-multimers with TRPC1. Hum. Mol. Genet 2009; 18:1238-1251). In keeping with its putative role in regulating cellular $Ca^{2+}$ homeostasis via intracellular $Ca^{2+}$ pools, PC2 interacts directly with the inositol 1,4,5-trisphosphate receptor (IP3R) (Li Y, Wright J M, Qian F, Germino G G, Guggino W B. Polycystin 2 interacts with type I inositol 1,4,5-trisphosphate receptor to modulate intracellular Ca2+ signaling. J. Biol. Chem 2005; 280:41298-41306) regulates the activity of the ryanodine receptor through direct interaction (Anyatonwu G I, Estrada M, Tian X, Somlo S, Ehrlich B E. Regulation of ryanodine receptor-dependent calcium signaling by polycystin-2. Proc. Natl. Acad. Sci. U.S.A 2007; 104:6454-6459) and has its own activity regulated by association with syntaxin-5 (Geng L, Boehmerle W, Maeda Y, Okuhara D Y, Tian X, Yu Z, Choe C U, Anyatonwu G I, Ehrlich B E, Somlo S. Syntaxin 5 regulates the endoplasmic reticulum channel-release properties of polycystin-2. Proc. Natl. Acad. Sci. U.S.A 2008; 105:15920-15925). Overexpression of PC1 also appears to modulate the properties of intracellular $Ca^{2+}$ stores by inhibiting capacitative $Ca^{2+}$ entry and rate of $Ca^{2+}$ re-uptake by the endoplasmic reticulum (Hooper K M, Boletta A, Germino G G, Hu Q, Ziegelstein R C, Sutters M. Expression of polycystin-1 enhances endoplasmic reticulum calcium uptake and decreases capacitative calcium entry in ATPstimulated MDCK cells. Am. J. Physiol Renal Physiol 2005; 289:F521-F530). While the interdependence of PC2 and PC1 in these process and the significance these effects on intracellular $Ca^{2+}$ homeostasis in the pathophysiology of cystic disease remains to be determined, these studies do lend support to the hypothesis that the polycystins impact a physiologically critical second messenger pathway that may influence a broad array of cellular functions. Several studies report that cAMP levels are elevated in cyst epithelial cells and furthermore that cAMP stimulates cyst fluid and electrolyte secretion (Belibi F A, Reif G, Wallace D P, Yamaguchi T, Olsen L, Li H, Helmkamp G M Jr. Grantham J J. Cyclic AMP promotes growth and secretion in human polycystic kidney epithelial cells. Kidney In need thereof 2004; 66:964-973; Yamaguchi T, Pelling J C, Ramaswamy N T, Eppler J W, Wallace D P, Nagao S, Rome L A, Sullivan L P, Grantham J J. cAMP stimulates the in vitro proliferation of renal cyst epithelial cells by activating the extracellular signal-regulated kinase pathway. Kidney Int 2000; 57:1460-1471). CFTR has been proposed as the apical chloride channel responsible for driving fluid secretion, providing a possible molecular explanation for cAMP's pro-secretory effects (Brill S R, Ross K E, Davidow C J, Ye M, Grantham J J, Caplan M J. Immunolocalization of ion transport proteins in human autosomal dominant polycystic kidney epithelial cells. Proc. Natl. Acad. Sci. U.S.A 1996; 93:10206-10211; Sullivan L P, Wallace D P, Grantham J J. Epithelial transport in polycystic kidney disease. Physiol Rev 1998; 78:1165-1191). A report that small-molecule inhibitors of CFTR reduced cyst growth in a murine model of PKD (Yang B, Sonawane N D, Zhao D, Somlo S, Verkman A S. Small-molecule CFTR inhibitors slow cyst growth in polycystic kidney disease. J. Am. Soc. Nephrol 2008; 19:1300-1310) support a role for CFTR in cyst growth. In vivo genetic studies combining CFTR and PKD mutant mice have not been reported. Whether CFTR is the sole channel responsible for fluid secretion in cysts is uncertain since CFTR does not appear to be expressed in all cysts (Lebeau C, Hanaoka K, Moore-Hoon M L, Guggino W B, Beauwens R, Devuyst O. Basolateral chloride transporters in autosomal dominant polycystic kidney disease. Pflugers Arch 2002; 444:722-731). The reasons for the high cytosolic cAMP concentrations in cyst cells is not well understood. It is possible that the perturbations in cytosolic $Ca^{2+}$ levels may in part account for dysregulation of cAMP in cyst cells. The polycystin proteins may directly or indirectly alter the activities of G-protein coupled receptors that signal through cAMP. Expression and activity of the V2 vasopressin receptor, for example, is elevated in a number of animal models of PKD (Belibi F A, Reif G, Wallace D P, Yamaguchi T, Olsen L, Li H, Helmkamp G M Jr. Grantham J J. Cyclic AMP promotes growth and secretion in human polycystic kidney epithelial cells. Kidney In need thereof 2004; 66:964-973; Gattone V H, Wang X, Harris P C, Torres V E. Inhibition of renal cystic disease development and progression by a vasopressin V2 receptor antagonist. Nat. Med 2003; 9:1323-1326). This fact is being exploited through the development of V2 receptor antagonists as potential therapeutic agents that can potentially slow or prevent cyst fluid accumulation by reducing cytosolic cAMP levels (Gattone V H, Wang X, Harris P C, Tones V E. Inhibition of renal cystic disease development and progression by a vasopressin V2 receptor antagonist. Nat. Med 2003; 9:1323-1326; Tones V E, Wang X, Qian Q, Somlo S, Harris P C, Gattone V H. Effective treatment of an orthologous model of autosomal dominant polycystic kidney disease. Nat. Med 2004; 10:363-364).

The mitogen activated protein kinase/extracellular regulated kinase (MAPK/ERK) cascade couples extracellular signals received by a variety of surface receptors, through the activation of small G-proteins and the involvement of a variety of adaptors, to the successive phosphorylation of Raf, MEK, and MAP kinase/ERK. Activated MAPK/ERK can modulate protein translation and can enter the nucleus to regulate the activities of transcription factors and the cell cycle. Activation of the MAPK/ERK pathway occurs in cell culture based models of ADPKD (Yamaguchi T, Nagao S, Wallace D P, Belibi F A, Cowley B D, Pelling J C, Grantham J J. Cyclic AMP activates B-Raf and ERK in cyst epithelial cells from autosomal-dominant polycystic kidneys. Kidney Int 2003; 63:1983-1994; Yamaguchi T, Wallace D P, Magenheimer B S, Hempson S J, Grantham J J, Calvet J P. Calcium restriction allows cAMP activation of the B-Raf/ERK pathway, switching cells to a cAMP-dependent growth-stimulated phenotype. J. Biol. Chem 2004; 279:40419-40430) as well as in vivo mouse models of the disease (Shibazaki S, Yu Z, Nishio S, Tian X, Thomson R B, Mitobe M, Louvi A, Velazquez H, Ishibe S, Cantley L G, et al. Cyst formation and activation of the extracellular regulated kinase pathway after kidney specific inactivation of Pkd1. Hum. Mol. Genet 2008; 17:1505-1516). ERK activation observed in cultured ADPKD patient cyst-derived cells has been attributed to cAMP-dependent activation of B-Raf (Yamaguchi T, Nagao S, Wallace D P, Belibi F A, Cowley B D, Pelling J C, Grantham J J. Cyclic AMP activates B-Raf and ERK in cyst epithelial cells from autosomal-dominant polycystic kidneys. Kidney Int 2003; 63:1983-1994; Yamaguchi T, Wallace D P, Magenheimer B S, Hempson S J, Grantham J J, Calvet J P. Calcium restriction allows cAMP activation of the B-Raf/ERK pathway, switching cells to a cAMP-dependent growth-stimulated phenotype. J. Biol. Chem 2004; 279:40419-40430). Inhibition of the MAPK/ERK cascade has slowed cyst formation in a murine cystic model based on a gene for human nephronophthisis (Omori S, Hida M, Fujita H, Takahashi H, Tanimura S, Kohno M, Awazu M. Extracellular signalregulated kinase inhibition slows disease progression in mice with polycystic kidney disease. J. Am. Soc. Nephrol 2006; 17:1604-1614) but the MEK1/2 inhibitor U0126 failed to alter the course of ADPKD in a conditional PKD1 gene inactivation model (Shibazaki S, Yu Z, Nishio S, Tian X, Thomson R B, Mitobe M, Louvi A, Velazquez H, Ishibe S, Cantley L G, et al. Cyst formation and activation of the extracellular regulated kinase pathway after kidney specific inactivation of PKD1. Hum. Mol. Genet 2008; 17:1505-1516). In light of the observations that the MAPK/ERK cascade is active in a variety of cell and animal models of PKD, the MAPK/ERK cascade kinases may be potential targets for future therapies in ADPKD.

The mTOR (mammalian target of rapamycin) protein is a kinase whose activation leads to increased protein translation and cell growth. The mTOR pathway is stimulated by cell surface receptors that signal through PI3 kinase to activate the AKT kinase. Activated AKT phosphorylates the tuberous sclerosis complex (TSC), composed of the TSC1 and TSC2 proteins (hamartin and tuberin). It is interesting to note that the TSC2/tuberin gene lies close to the PKD1 gene on chromosome 16 and occasionally results in a contiguous gene deletion syndrome manifesting severe ADPKD and features of TSC as well. Support for link between the mTOR pathway and ADPKD is provided by studies demonstrating that downstream effectors of the mTOR pathway are inappropriately activated in cyst lining cells (Shillingford J M, Murcia N S, Larson C H, Low S H, Hedgepeth R, Brown N, Flask C A, Novick A C, Goldfarb D A, Kramer-Zucker A, et al. The mTOR pathway is regulated by polycystin-1, and its inhibition reverses renal cystogenesis in polycystic kidney disease. Proc. Natl. Acad. Sci. U.S.A 2006; 103:5466-5471). Administration of rapamycin in rodent models of PKD has slowed cyst development suggesting the possibility that inappropriate activation of the mTOR pathway is associated with or in part responsible for the excessive proliferation of renal epithelial cells that characterizes PKD (Shillingford J M, Murcia N S, Larson C H, Low S H, Hedgepeth R, Brown N, Flask C A, Novick A C, Goldfarb D A, Kramer-Zucker A, et al. The mTOR pathway is regulated by polycystin-1, and its inhibition reverses renal cystogenesis in polycystic kidney disease. Proc. Natl. Acad. Sci. U.S.A 2006; 103:5466-5471; Tao Y, Kim J, Schrier R W, Edelstein C L. Rapamycin markedly slows disease progression in a rat model of polycystic kidney disease. J. Am. Soc. Nephrol 2005; 16:46-51; Wahl P R, Serra A L, Le H M, Molle K D, Hall M N, Wuthrich R P. Inhibition of mTOR with sirolimus slows disease progression in Han:SPRD rats with autosomal dominant polycystic kidney disease (ADPKD). Nephrol. Dial. Transplant 2006; 21:598-604). Recent evidence suggests that PC-1 inhibits the mTOR pathway in a Tsc2-dependent manner and thereby regulates cell size as well (Distefano G, Boca M, Rowe I, Wodarczyk C, Ma L, Piontek K B, Germino G G, Pandolfi P P, Boletta A. Polycystin-1 regulates extracellular signal-regulated kinase-dependent phosphorylation of tuberin to control cell size through mTOR and its downstream effectors S6K and 4EBP1. Mol. Cell Biol 2009; 29:2359-2371). Taken together, these data suggest that under normal circumstances the PC1 exerts an inhibitory influence on the strength of mTOR signaling. This pathway represents another potential target for therapy in ADPKD.

Oriented cell division (OCD) is controlled by the planar cell polarity (PCP) pathway through non-canonical Wnt signaling (Gong Y, Mo C, Fraser S E. Planar cell polarity signalling controls cell division orientation during zebrafish gastrulation. Nature 2004; 430:689-693). Several lines of evidence support the role of oriented cell division in shaping tissues (Ahringer J. Control of cell polarity and mitotic spindle positioning in animal cells. Curr. Opin. Cell Biol 2003; 15:73-81) and a role for loss of OCD in cyst formation has been proposed (Fischer E, Legue E, Doyen A, Nato F, Nicolas J F, Tones V, Yaniv M, Pontoglio M. Defective planar cell polarity in polycystic kidney disease. Nat. Genet 2006; 38:21-23; Germino G G. Linking cilia to Wnts. Nat. Genet 2005; 37:455-457). The elongating nephron of the developing kidney shows significant cellular proliferation yet the tubules grow in a longitudinal direction without an appreciable increase in cross section (Fischer E, Legue E, Doyen A, Nato F, Nicolas J F, Torres V, Yaniv M, Pontoglio M. Defective planar cell polarity in polycystic kidney disease. Nat. Genet 2006; 38:21-23). The mitotic spindles during this tubular elongation phase appear to orient along the long axis of the tubule and cell division takes place in this orientation. Loss of OCD occurs prior to cyst formation in two cystic animal models, Hnflo deficient mice and the pck rat (orthologous ARPKD model (Fischer E, Legue E, Doyen A, Nato F, Nicolas J F, Torres V, Yaniv M, Pontoglio M. Defective planar cell polarity in polycystic kidney disease. Nat. Genet 2006; 38:21-23). Consistent with these findings, disruption of the PCPrelated protocadherin Fat4 results in tubular cysts in kidney development, a process further exacerbated by reduction in the dose of the core PCP gene, Vang12 (Saburi S, Hester I, Fischer E, Pontoglio M, Eremina V, Gessler M, Quaggin S E, Harrison R, Mount R, McNeill H. Loss of Fat4 disrupts PCP signaling and oriented cell division and leads to cystic kidney disease. Nat. Genet 2008; 40:1010-1015). Recent data suggests a more complex view of PCP processes in the kidney. During tubular condensation in the earliest stages of kidney development, convergent extension movements, not OCD, seem to drive establishment of tissue polarity (Kamer C M, Chirumamilla R, Aoki S, Igarashi P, Wallingford J B, Carroll T J. Wnt9b signaling regulates planar cell polarity and kidney tubule morphogenesis. Nat. Genet 2009; 41:793-799). A mouse model with a hypomorphic ARPKD gene mutation shows similar loss of OCD but never develops cysts, suggesting that loss of OCD is not sufficient for cyst formation. Conversely, PKD1 and PKD2 mouse models that develop cystic kidneys have normal OCD in pre-cystic tubules but lose this property as the tubules start to dilate. Loss of OCD is a marker for dysregulated PCP activity and some cystic disease genes (e.g., Pkhd1) may impact PCP phenotypes, but loss of OCD may not be a direct cause of cystic expansion.

While PCP uses components of the non-canonical Wnt signaling pathway, the role of the canonical Wnt pathway is more compelling in ADPKD. The canonical Wnt pathway functions through β-catenin and controls cell proliferation and differentiation during development (Moon R T. Wnt/beta-catenin pathway. Sci. STKE 2005; 2005:cm1). The canonical Wnt pathway actively regulates the availability of β-catenin for nuclear translocation. Evidence for a role of canonical Wnt signaling in PKD comes from studies showing that transgenic expression of constitutively active β-catenin or kidney-specific inactivation of the APC gene results in cyst formation (Karner C M, Chirumamilla R, Aoki S, Igarashi P, Wallingford J B, Carroll T J. Wnt9b signaling regulates planar cell polarity and kidney tubule morphogenesis. Nat. Genet 2009; 41:793-799; Qian C N, Knol J, Igarashi P, Lin F, Zylstra U, Teh B T, Williams B O. Cystic renal neoplasia following conditional inactivation of apc in mouse renal tubular epithelium. J. Biol. Chem 2005; 280:3938-3945; Saadi-Kheddouci S, Berrebi D, Romagnolo B, Cluzeaud F, Peuchmaur M, Kahn A, Vandewalle A, Perret C. Early development of polycystic kidney disease in transgenic mice expressing an activated mutant of the beta-catenin gene. Oncogene 2001; 20:5972-5981). The direct connection between ADPKD and canonical Wnt signaling remains speculative since conflicting reports state in one case that the C-terminus of PC1 acts as an activator of β-catenin transcription (Kim E, Arnould T, Sellin L K, Benzing T, Fan M J, Gruning W, Sokol S Y, Drummond I, Walz G. The polycystic kidney disease 1 gene product modulates Wnt signaling. J. Biol. Chem 1999; 274:4947-4953) whereas a more recent study implicates the C-terminal tail of PC1 as an inhibitor of β-catenin-TCF mediated transcription (Lal M, Song X, Pluznick J L, Di G, V, Merrick D M, Rosenblum N D, Chauvet V, Gottardi C J, Pei Y, Caplan M J. Polycystin-1 C-terminal tail associates with beta-catenin and inhibits canonical Wnt signaling. Hum. Mol. Genet 2008; 17:3105-3117). Taken together, it appears that Wnt signaling constitutes a plausible downstream effecter mechanism for some aspects of PKD and that the balance between canonical and non-canonical signaling may be a factor (Simons M, Gloy J, Ganner A, Bullerkotte A, Bashkurov M, Kronig C, Schermer B, Benzing T, Cabello O A, Jenny A, et al. Inversin, the gene product mutated in nephronophthisis type II, functions as a molecular switch between Wnt signaling pathways. Nat. Genet 2005; 37:537-543).

The cellular pathways associated with PLD (e.g., ADPLD or ARPLD) are similar to those associated with PKD. For example, the absence of PC1, PC2, and fibrocystin/polyductin, normally localized to primary cilia, represent a potential mechanism leading to cyst formation, associated with increased cell proliferation and apoptosis, enhanced fluid secretion, abnormal cell-matrix interactions, and alterations in cell polarity. Proliferative and secretive activities of cystic epithelium can be regulated by estrogens either directly or by synergizing growth factors including nerve growth factor, IGF1, FSH and VEGF. The abnormalities of primary cilia and the sensitivity to proliferative effects of estrogens and different growth factors in PLD cystic epithelium provide the morpho-functional basis for future treatment targets, based on the possible modulation of the formation and progression of hepatic cysts.

Certain compounds described herein (e.g., compounds of any one of Formulae (I-1) to (I-3)) have been reported as anti-tumor agents. See, e.g., Fedeles et al., *Journal of Biological Chemistry*, 2011, 286(39) 33910-33920; U.S. patent application publication, US 2006/0019936, each of which is incorporated herein by reference). Compounds of described herein, such as compounds of Formula (I) or (II), and pharmaceutically acceptable salts, hydrates, solvates, polymorphs, co-crystals, tautomers, and isotopically labeled derivatives thereof, may be useful in treating PKD and PLD. Without wishing to be bound by any particular theory, compounds described herein may be mTOR inhibitors, mitochondrial respiration inhibitors (e.g., complex 1 inhibitors), oxidative-stress inducers, and/or activators of unfolded protein response (UPR). For example, compounds described herein may act on the mitochondria. Compounds described herein may inhibit complex I in the respiratory chain resulting in mitochondrial dysfunction and production of excess reactive oxygen species (ROS) (Fedeles et al., *J. Biol. Chem.* 2011, 286, 33910-33920; Wilson, *Biochim. Biophys. Acta* 2011, 1812, 1201). Structure-activity studies surprisingly revealed that compounds described herein inhibited complex I. In contrast, complex I inhibition was not observed in cells treated with the comparative compounds, where each one of the comparative compounds included a substituted or unsubstituted Ring A or substituted or unsubstituted Ring B as described herein, but not both Rings A and B. Therefore, the compounds described herein may be useful in killing cells sensitive to oxidative stress and/or in inhibiting the growth of such cells. One example of non-cancerous cells sensitive to oxidative stress are the cyst cells that cause PKD or PLD (Wilson, *Biochim. Biophys. Acta* 2011, 1812, 1201). ROS and/or mitochondrial dysregulation may be responsible for inducing UPR. Complex I inhibition and/or mitochondrial dysregulation may lead to increased ROS, which in turn activates the ASK- (apoptosis signal-regulating kinase-) JNK (c-Jun N-terminal kinase) pathway by changing the redox state of thioredoxin, a cellular redox sensor. This may be sufficient for the UPR induction. Alternatively, UPR may be induced independently of ROS. Nevertheless, the ASK-JNK pathway may amplify the XBP1s response and initiates apoptosis in part via Caspase-12. Zhang et al., *Neurology*. 2006; 66 (2 Suppl 1):S102-S109; Kaser et al., *Cell*. 2008; 134(5):743-756.

Additionally, the mTOR pathway may play a role in the cytotoxicity of compounds described herein. It was observed that exposure of a cyst cell to a compound described herein (e.g., compound of Formula (I-1)) leads to a rapid loss of phosphorylation on P70S6 kinase, a downstream target of mTOR, suggesting that a compound described herein may be an inhibitor of the mTOR pathway. Inhibition of the mTOR pathway have also been associated to endoplasmic reticulum (ER) stress which triggers the unfolded protein response (UPR). Specifically, UPR-dependent apoptosis is sensitive to rapamycin, a well-known inhibitor of the mTOR pathway (Ozcan, U., Ozcan, L., Yilmaz, E., Dlivel, K., Sahin, M., Manning, B. D., and Hotamisligil, G. S. (2008) Loss of the tuberous sclerosis complex tumor suppressors triggers the unfolded protein response to regulate insulin signaling and apoptosis, *Mol. Cell* 29, 541-551). It was found that compounds described herein (e.g., compound of Formula (I-1) or (I-2)) are potent activators of the IRE1/ JNK/XBP1 branch of the UPR as evidenced by endoribonucleolytic processing of XPB1 See, e.g., Example 2. ER stress-induced oligmerization of IREI induces its ribonuclease and kinase activities. The latter has been coupled with activation of the ASKI/JNK protein kinase pathways and apoptosis. These results provided a strong indication that compounds described herein may be effective against PKD and PLD, because PKD and PLD cells are already under ER stress due to a dysregulated mTOR pathway. Moreover, compounds described herein (e.g., compound of Formula (I-1)) was also effective in preventing cyst formation in a PKD1 knockout (PKD1 KO) mouse model. See, e.g., Example 3. Therefore, compounds described herein, and pharmaceutical compositions thereof, may be useful in treating PKD and PLD, in inhibiting the growth of a cyst cell, and in killing a cyst cell. Possibly having multiple mechanisms of action, which include mTOR inhibition, induction of UPR, and perturbation of mitochondrial (e.g., complex I and/or complex II) function, the compounds described herein hold great promise for being clinically efficacious.

In one aspect, the present invention provides methods of treating and/or preventing PKD or PLD in a subject in need thereof using a compound described herein, or a pharmaceutical composition thereof. In certain embodiments, provided are methods of treating ADPKD. In certain embodiments, provided are methods of treating ARPKD. In certain embodiments, provided are methods of treating ADPLD. In certain embodiments, provided are methods of treating ARPLD.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Another aspect of the present invention relates to methods of inhibiting the growth of a cyst cell using a compound described herein, or a pharmaceutical composition thereof. In certain embodiments, an inventive method specifically inhibits the growth of a cyst cell, compared to a non-cyst cell. In certain embodiments, an inventive method specifically inhibits the growth of a cyst cell that causes PKD or PLD, compared to a cyst cell that does not cause PKD or PLD. In certain embodiments, the growth of a cyst cell is inhibited by the inventive methods. In certain embodiments, the growth of a cyst cell is specifically inhibited by the inventive methods, compared to a non-cyst cell. In certain embodiments, the growth of a cyst cell that causes PKD or PLD is specifically inhibited by the inventive methods, compared to a cyst cell that does not cause PKD or PLD.

Another aspect of the present invention relates to methods of killing a cyst cell using a compound described herein, or a pharmaceutical composition thereof. In certain embodiments, an inventive method specifically kills a cyst cell, compared to a non-cyst cell. In certain embodiments, an inventive method specifically kills a cyst cell that causes PKD or PLD, compared to a cyst cell that does not cause PKD or PLD. In certain embodiments, a cyst cell is killed by the inventive methods. In certain embodiments, a cyst cell is specifically killed by the inventive methods, compared to a non-cyst cell. In certain embodiments, a cyst cell that causes PKD or PLD is specifically killed by the inventive methods, compared to a cyst cell that does not cause PKD or PLD.

In certain embodiments, the cyst cell described herein is a cyst cell causing PKD (e.g., ADPKD or ARPKD). In certain embodiments, the cyst cell is a cyst cell causing PLD (e.g., ADPLD or ARPLD). In certain embodiments, the cyst cell is a PKD1 null cell. In certain embodiments, the cyst cell is a PKD2 null cell. In certain embodiments, the cyst cell described herein is in vivo. In certain embodiments, the cyst cell is in vitro. In certain embodiments, the cyst cell is ex vivo.

In certain embodiments, the specificity described herein (e.g., the specificity in inhibiting the growth of or killing a cyst cell, compared to a non-cyst cell, or the specificity in inhibiting the growth of or killing a cyst cell causing PKD or PLD, compared to a cyst cell not causing PKD or PLD) is at least about 1-fold, at least about 1.5-fold, at least about 2-fold, at least about 4-fold, at least about 10-fold, at least about 30-fold, or at least about 100-fold. In certain embodiments, the specificity is at least about 2-fold.

In certain embodiments, the methods of the invention include administering to a subject in need thereof an effective amount of a compound described herein, or a pharmaceutical composition thereof. In certain embodiments, the methods of the invention include administering to a subject in need thereof a therapeutically effective amount of a compound described herein, or a pharmaceutical composition thereof. In certain embodiments, the methods of the invention include contacting a cell with an effective amount of a compound described herein, or a pharmaceutical composition thereof. In certain embodiments, the methods of the invention include contacting a cell with a therapeutically effective amount of a compound described herein, or a pharmaceutical composition thereof.

Another aspect of the invention relates to methods of screening a library of compounds to identify one or more compounds that are useful in the methods of the invention. In certain embodiments, the one or more compounds identified are useful for treating and/or preventing PKD (e.g., ADPKD or ARPKD) in a subject in need thereof. In certain embodiments, the one or more compounds identified are useful for treating and/or preventing PLD (e.g., ADPLD or ARPLD) in a subject in need thereof. In certain embodiments, the one or more compounds identified are useful for inhibiting the growth of a cyst cell (e.g., a cyst cell causing PKD or PLD). In certain embodiments, the one or more compounds identified are useful for killing a cyst cell (e.g., a cyst cell causing PKD or PLD). In certain embodiments, the library of compounds is a library of compounds described herein. In certain embodiments, the methods of screening a library include providing at least two different compounds described herein; and performing at least one assay using the different compounds described herein, to identify one or more compounds that are useful in the inventive methods.

Typically, the methods of screening a library of compounds involve at least one assay. In certain embodiments, the assay is performed to detect one or more characteristics associated with the treatment and/or prevention of PKD or PLD, with the inhibition of the growth of a cyst cell, and/or with the killing of a cyst cell. The characteristics may be desired (e.g., PKD or PLD being treated or prevented, or a cyst cell being killed) or undesired (e.g., PKD or PLD not being treated or prevented, or a cyst cell not being killed) characteristics. The assay may be an immunoassay, such as a sandwich-type assay, competitive binding assay, one-step direct test, two-step test, or blot assay. The step of performing at least one assay may be performed robotically or manually.

In another aspect, the present invention provides the compounds described herein, and pharmaceutical compositions thereof, for use in the treatment and/or prevention of PKD or PLD in a subject in need thereof.

In still another aspect, the present invention provides the compounds described herein, and pharmaceutical compositions thereof, for use in inhibiting the growth of a cyst cell (e.g., a cyst cell causing PKD or PLD).

In yet another aspect, the present invention provides the compounds described herein, and pharmaceutical compositions thereof, for use in killing a cyst cell (e.g., a cyst cell causing PKD or PLD).

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds

Any of the compounds described herein can be prepared by routine methods known in the art. For example, one can use synthetic chemistry transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. One exemplary synthesis of the compounds described herein is reported in Fedeles et al., *Journal of Biological Chemistry*, 2011, 286(39) 33910-33920 and in U.S. patent application publication, US 2006/0019936.

Example 2. Compound I-1 is an Activator of the XBP1 (X-Box Binding Protein 1) Branch of the UPR (Unfolded Protein Response) as Evidenced by Endoribonucleolytic Processing of XBP1

Endoribonucleolytic processing of XBP1 in HeLa cells were performed according to methods known in the art. See, e.g., U.S. Patent Application Publication, US 2004/0170622, which is incorporated herein by reference. In an exemplary set of experiments, the HeLa cells were treated with compound I-1 at 5 µM or thapsigargin (Tg) at 200 nM, or not treated with either compound. Levels of spliced and unspliced XBP1 transcript relative to untreated cells were measured. The results indicate that compound I-1 is a potent activator of the XBP1 branch of the UPR (FIG. 1).

Figure 2:
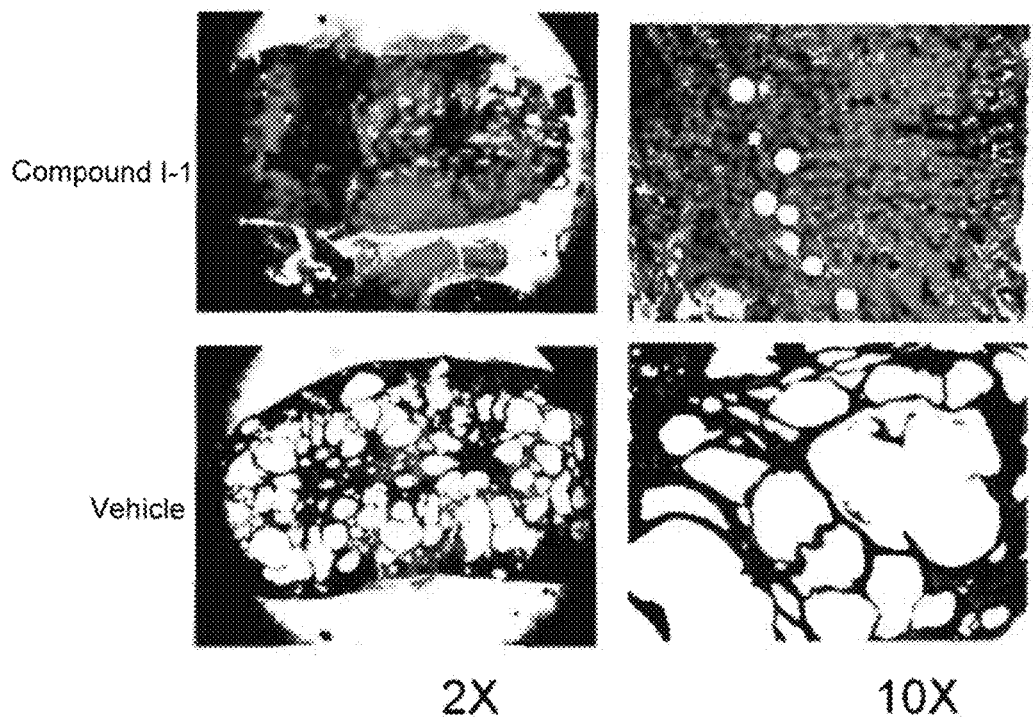
FIG. 2 is an unlimited example and shows the effects of compound I-1 on the development of polycystic kidney disease (PKD) in PKD/1$^{flow/flox}$; Pkhd1 Cre mice. Neonate mice were treated IP daily, with compound I-1 at a dose of 10 mg/kg starting on day 10 post birth for 7 days. The results shown were from day P16. The staining was hematoxylin and eosin (H&E) stain.

Example 3. Compound I-1 was Effective in Preventing Cyst Formation in a PKD1 Knockout (PKD1 KO) Mouse Model PKD1$^{flox/flox}$: Pkhd1Cre mice were used. Neonate mice were treated IP (intraperitoneally) daily, with compound I-1 at a dose of 10 mg/kg starting on day 10 post birth for 7 days. The results shown were from day P16 (the 16$^{th}$ day postbirth). The staining was hematoxylin and eosin (H&E) stain. The results are shown in FIG. 2. Compared to the vehicle-treated mice, the mice treated with compound I-1 showed significantly fewer cysts, which translated into kidney sizes closer to normal, smaller average cyst size, significantly lower cystic index (a score based on histologic evaluation), and a significantly improved kidney function, as evidenced by lower BUN (blood urea nitrogen).

Figure 3A:
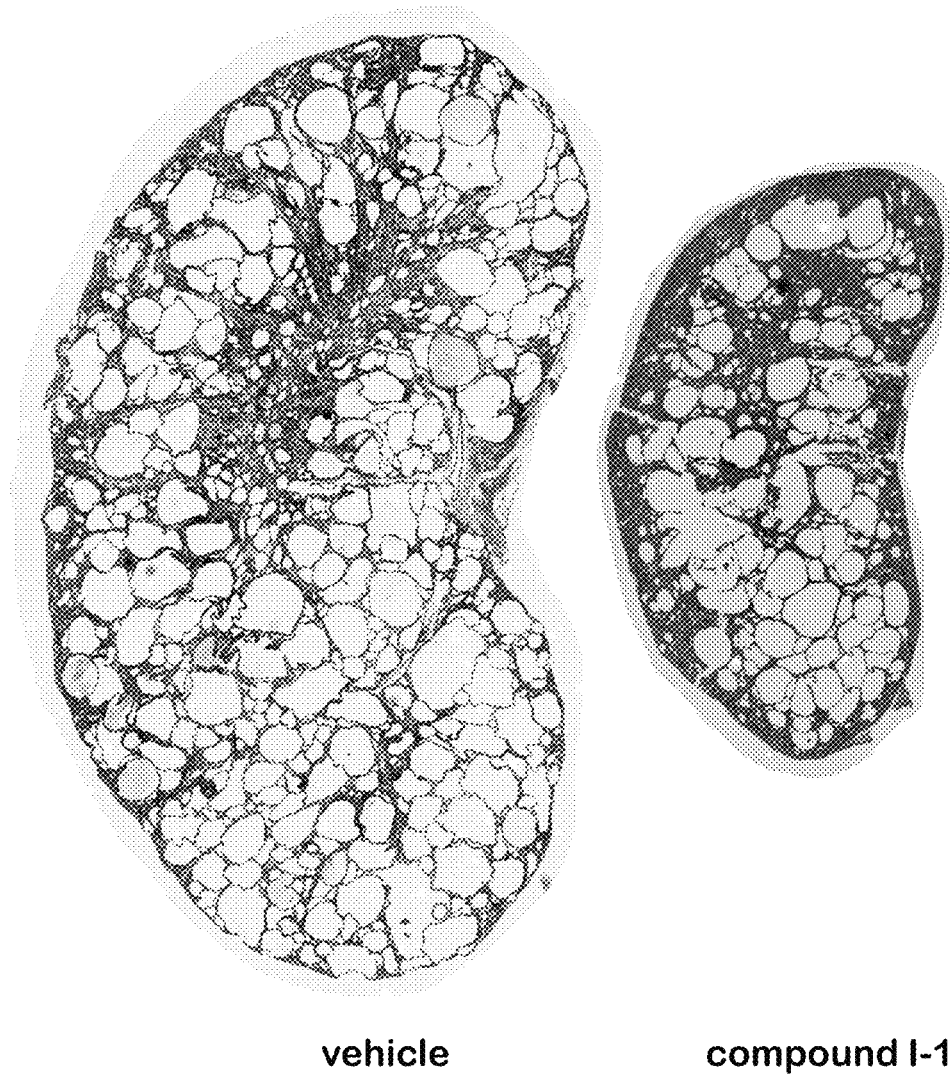
Figure 3E:
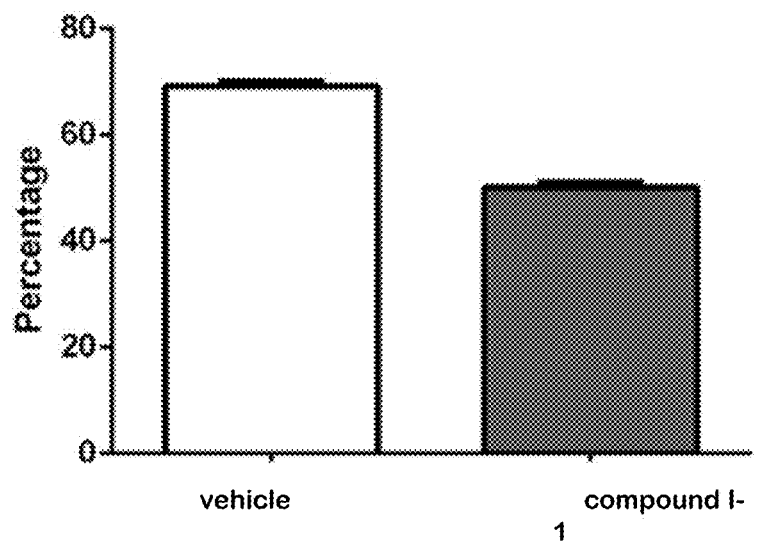
Figure 3F:
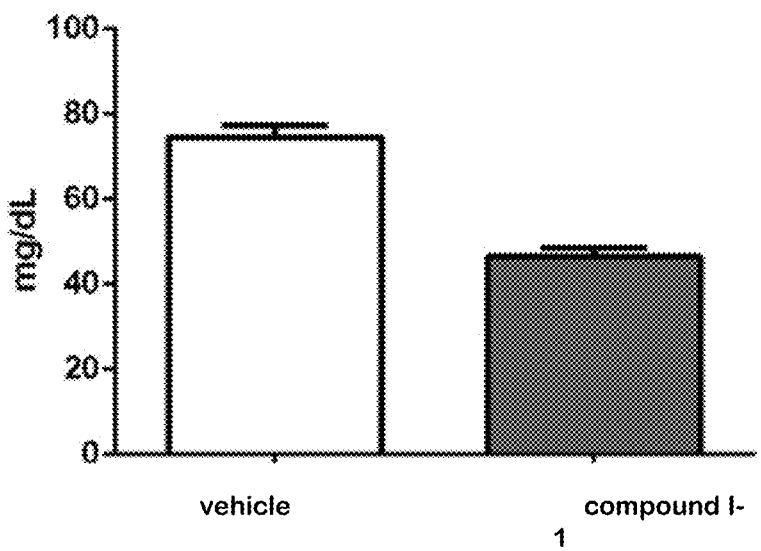
Figure 4A:
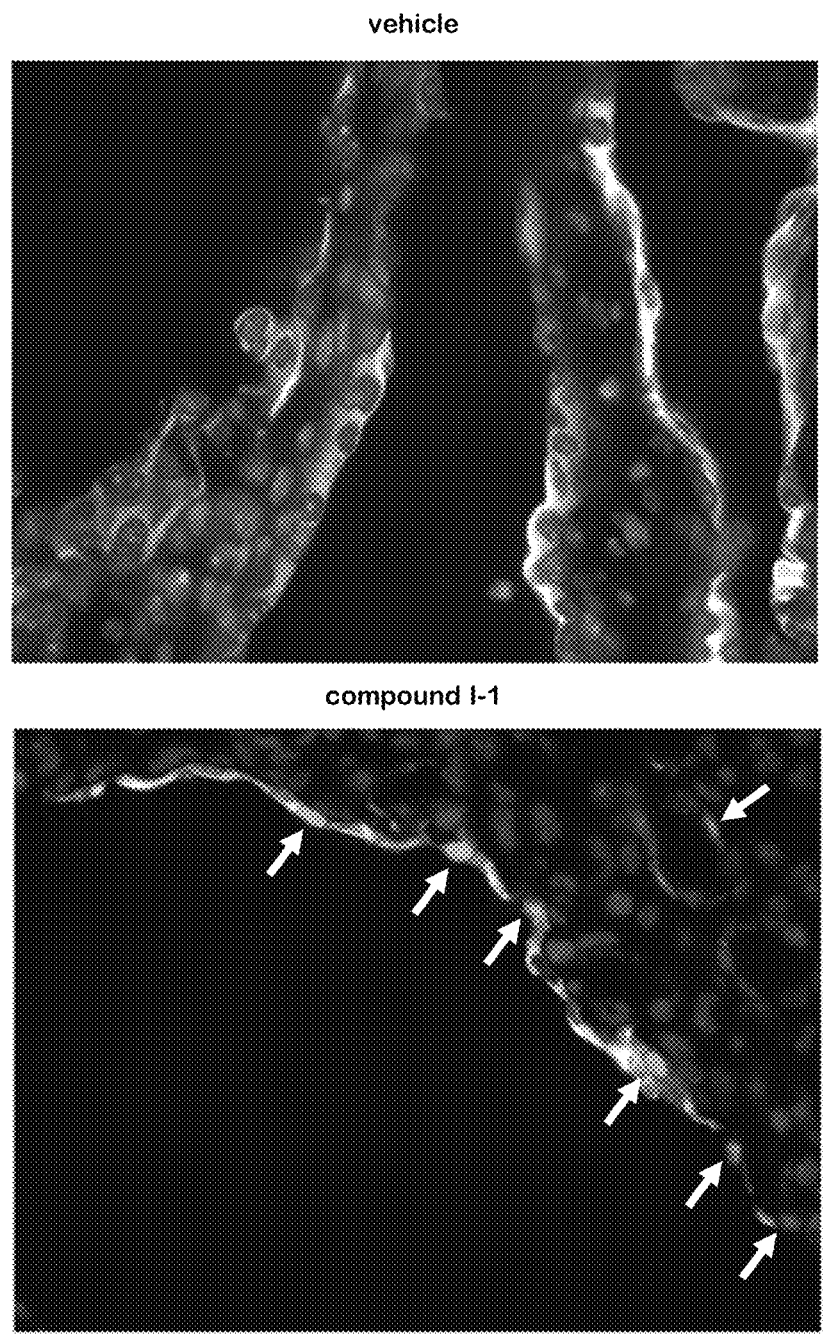
FIG. 4A to FIG. 4B are unlimited examples and show that compound I-1 specifically increased the apoptosis of PKD1 null cells compared to control in vitro as well as in vivo as assessed by the cell-titer blue viability assay (in vitro) or TUNEL staining (in vivo).
Figure 4B:
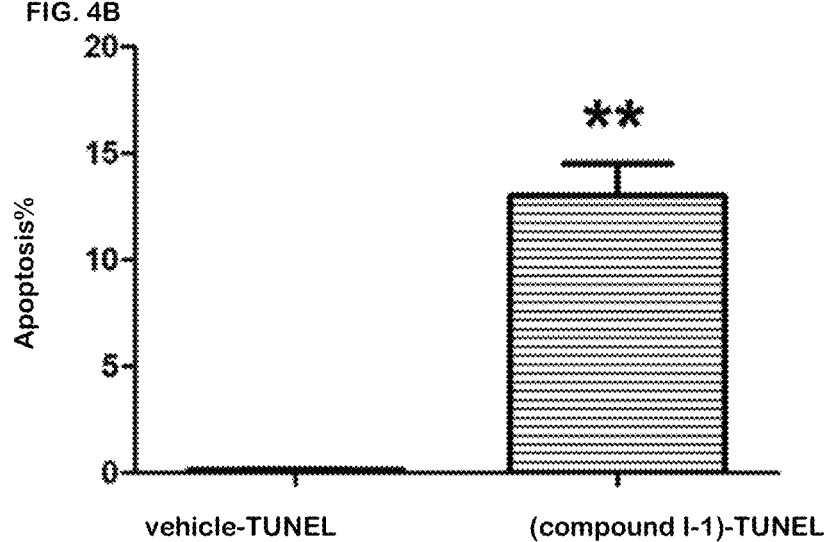
Figure 4C:
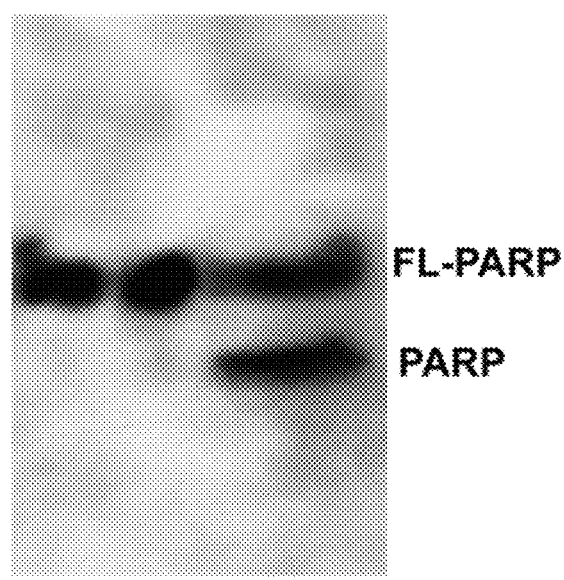
FIG. 4C is an unlimited example and shows that the cleaved PARP (an apoptosis marker) significantly increased in the treated tissues in vivo.

Example 4. Compound I-1 is a Potent and Specific Inducer of Apoptosis of PKD1 Null Cells Both In Vitro and In Vivo in Mice An orthologous PKD1 model was used where PC1 was conditionally inactivated in the collecting duct using Pkhd1-Cre mice. Mice were given daily intraperitoneal injections of compound I-1 between P10 (the 10$^{th}$ day post-birth) and P24 (the 24$^{th}$ day post-birth). Morphological and biochemical parameters, such as the ratio of kidney weight to body weight (KW/BW), cystic index, BUN and apoptosis were examined. The results shown in FIG. 3A to FIG. 3F demonstrate that an administration of compound I-1 to PKD1 mutant mice resulted in fewer cysts and smaller average cyst size (FIG. 3A), a dramatic decrease in kidney weight (KW, FIG. 3C) and KW/BW ratio (FIG. 3D) as compared to vehicle injected controls (3 fold decrease in KW and KW/BW;*$p<0.001$); importantly, the body weight of treated mice was not statistically lower than that of the controls (FIG. 3B). These changes were accompanied by a 1.5-fold decrease in cystic index (*$p<0.001$; FIG. 3E) and a 2-fold decrease in BUN levels (*$p<0.001$; FIG. 3F). Compound I-1 specifically increased the apoptosis of PKD1 null cells compared to control (2-fold; *$p<0.001$) in vitro as well as in vivo (4-fold; *$p<0.001$) as assessed by the cell-titer blue viability assay (in vitro) or TUNEL staining (in vivo) (FIG. 4A and FIG. 4B). Apoptosis markers, such as cleaved PARP were also significantly increased in the treated tissues, in vivo (FIG. 4C). Importantly, the effect of compound I-1 was specific in vivo, as the vast majority of apoptotic cells stained positive for DBA (where the Cre is active; FIG. 4A**) whereas LTA-positive cells did not exhibit increased apoptosis in compound I-1 compared to the control. These data indicate that compound I-1 is a potent and specific inducer of apoptosis of PKD1 null cells both in vitro and in vivo.

Figure 5:
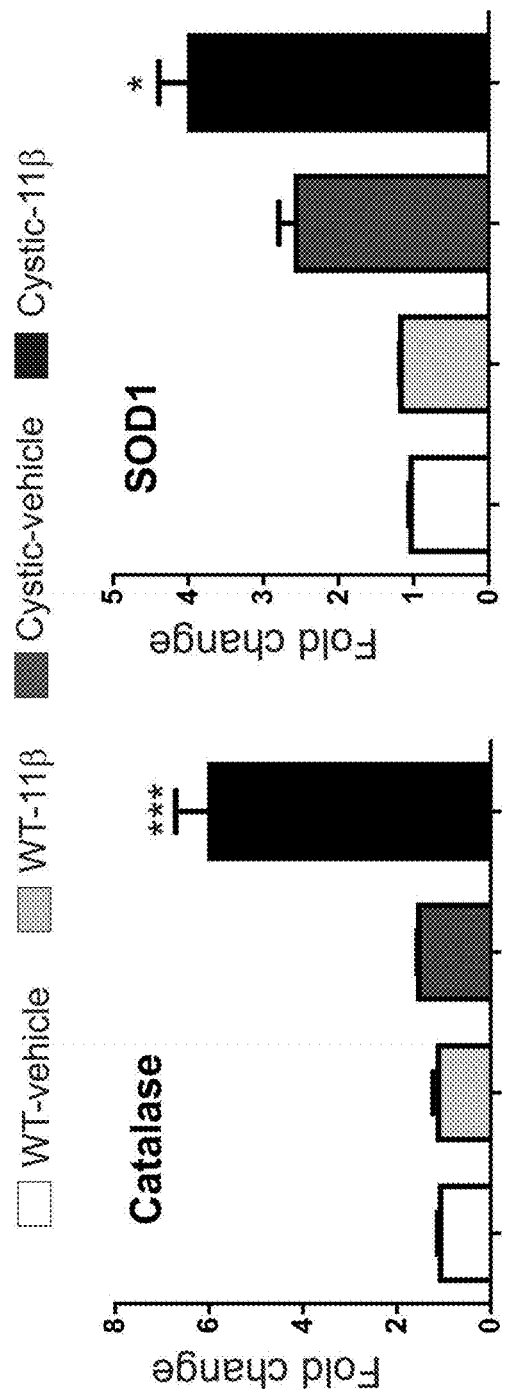
FIG. 5 is an unlimited example and shows the mRNA levels of oxidative stress responsive genes Catalase (left panel) and superoxide dismutase (SOD1; right panel) analyzed by qPCR. WT-1113: mouse WT- (wild type-) kidney cells treated with compound I-1. Cystic-1113: mouse cystic kidney cells treated with compound I-1.

Example 5. Oxidative Stress in Kidneys Treated with Compound I-1 mRNA levels of oxidative stress responsive genes Catalase and superoxide dismutase (SOD1) were analyzed by qPCR. Exemplary results are shown in FIG. 5. mRNA levels were increased (6-fold (***$p<0.001$) and 4-fold (*$p<0.05$), respectively) when mouse (the early model) cystic kidneys were treated with compound I-1. This suggests that the ability of compound I-1 to induce oxidative stress was selective for the cystic cells and did not happen in the normal (wild-type) cells.

Example 6. Efficacy of Compound I-1 in an Adult Mouse Model

Figure 6B:
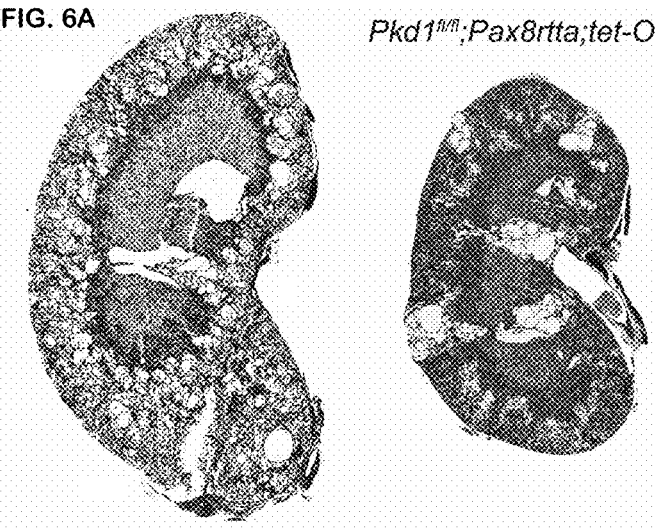
Figure 6B:
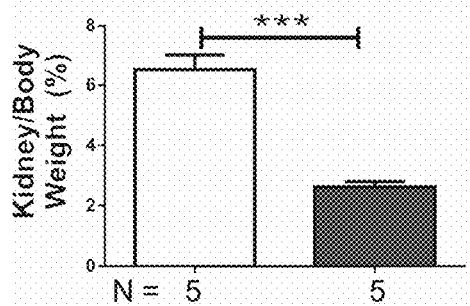
Figure 6C:
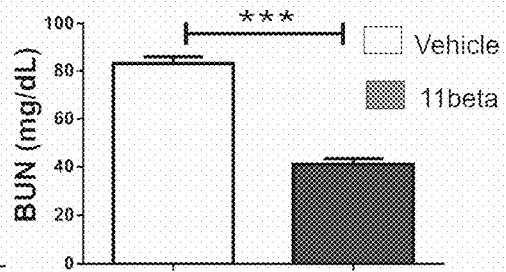

An adult model ("adult Pax8"), the doxycycline inducible Pax8rtTA; Tet O-Cre; Pkd1flox/flox mouse, was used (Ma et al., *Nat. Genet.* 2013, 45(9):1004-1012). These mice received doxycycline in the drinking water from P28-P42 to induce Cre and inactivate Pkd1. The adult mouse model inactivates the PKD1 gene (which causes PKD) after the mice are adult, and thus the adult mouse model mimics the human with PKD. This is considered the gold standard mouse model in the PKD field. Treatment was started at P42 with 3×/week i.p. injection of compound I-1 for 12 weeks. The mice were examined at the end of that period at the age of 18 weeks. It was observed that compound I-1 was very effective at slowing down cyst growth, as evidenced by kidney morphology, a significant 2.5 fold (*$p<0.001$) decrease in the kidney/body ratio and a 2-fold (*$p<0.001$) decrease in BUN (indicating improved kidney function). Exemplary results are shown in FIG. 6A to FIG. 6C.

Example 7. Efficacy of Compound I-3 in an Early Mouse Model

Figure 7A:
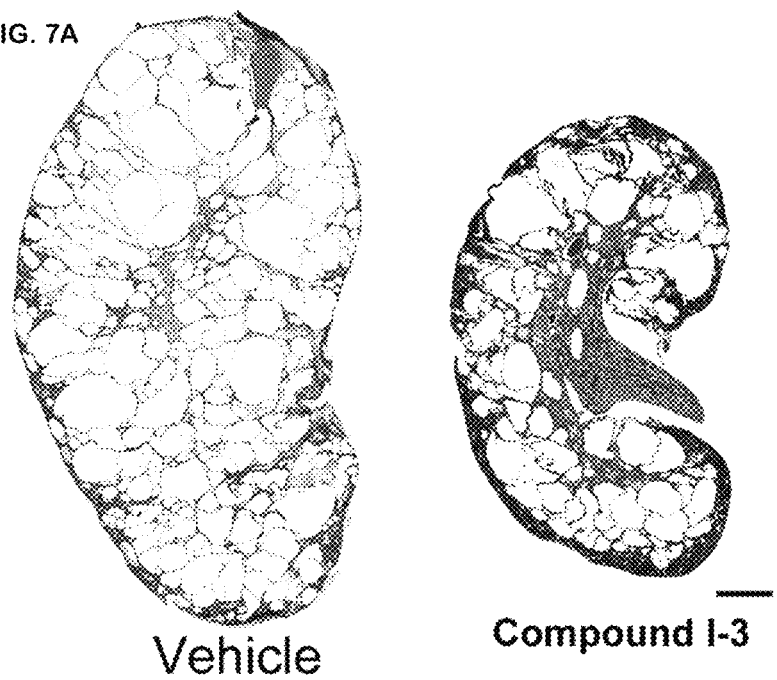
FIG. 7A to FIG. 7C are unlimited examples and show the efficacy of compound I-3 in an early mouse model.
Figure 7B:
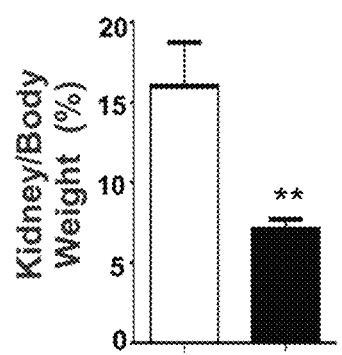
Figure 7C:
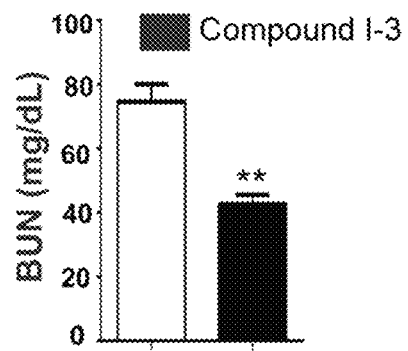

Compound I-3 was tested using the methods described in Example 4. Exemplary results are shown in FIG. 7A to FIG. 7C. Compound 1-3 worked very well, as shown by the smaller kidney morphology (FIG. 7A), a 2-fold ($p<0.01$) decrease in the kidney/body ratio (FIG. 7B), and 1.5 fold ($p<0.01$) decrease in BUN (improved kidney function) (FIG. 7C). Compound 1-3 may be even more active than compound I-1, as in this experiment, mice were treated with compound I-3 at a 5 mg/kg dose, half of the dose of compound I-1. It was also shown that the ability of compounds I-1 to damage DNA (the aniline mustard group) was not necessary for the activity of the compounds against PKD.

Figure 8A:
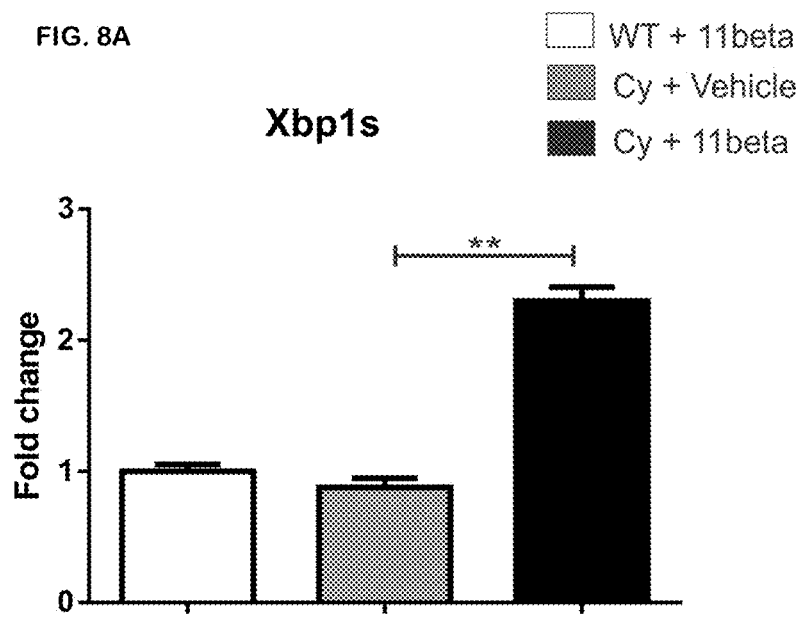
FIG. 8A and FIG. 8B are unlimited examples and show that compound I-1 up-regulated the unfolded protein response (UPR) in mouse cystic kidneys. 11beta: compound I-1. WT: wild type. Cy: cystic.
Figure 8B:
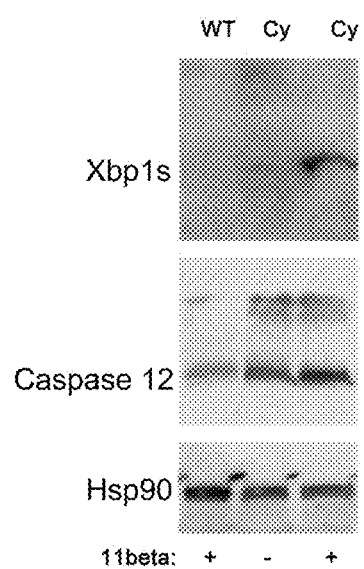

Example 8. Compound I-1 Up-Regulated the Unfolded Protein Response (UPR) in the Cystic Kidneys Increased (2.5 fold, $p<0.01$) mRNA levels (by qPCR) of spliced XBP1 (XBP1s, the activated form of XBP1) were observed when mouse (the early model) cystic kidney was treated with compound I-1 (FIG. 8A). This result signified up-regulated UPR. What were also observed include increased protein levels (by Western blotting) of XBP1s and of caspase-12, a downstream effector of XBP1s (FIG. 8B**). The upregulation of caspase-12 may be through the mechanism by which activation of UPR leads to cell death.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or

What is claimed is:

1. A method of treating polycystic kidney disease in a subject in need thereof, the method comprising administering to the subject a therapeutically effective amount of a compound, wherein the compound is of the formula:

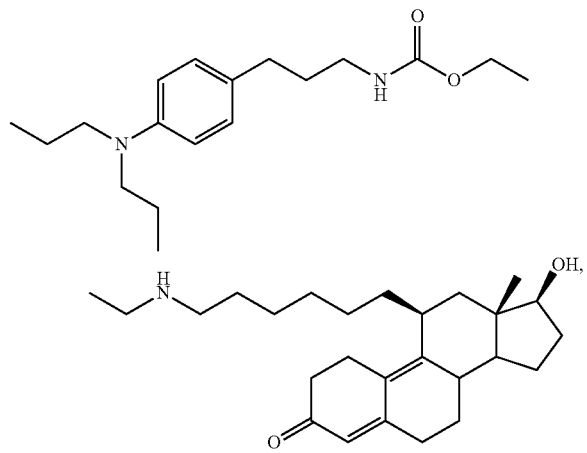

or a pharmaceutically acceptable salt thereof, or a pharmaceutical composition of said compound.

2. The method of claim 1, wherein the polycystic kidney disease is autosomal dominant polycystic kidney disease.

3. The method of claim 1, wherein the polycystic kidney disease is autosomal recessive polycystic kidney disease.

4. A method of treating polycystic liver disease in a subject in need thereof, the method comprising administering to the subject a therapeutically effective amount of a compound, wherein the compound is of formula:

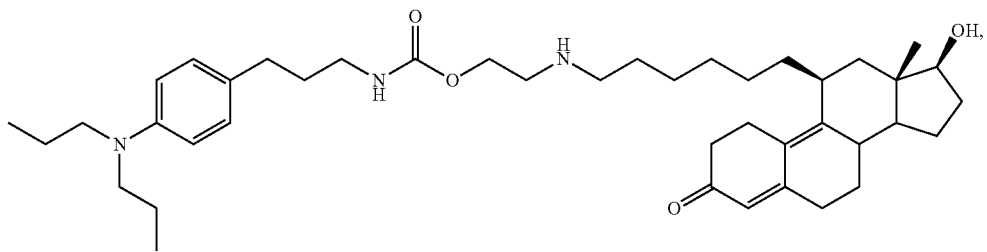 [SMILES: CCCN(CCC)c1ccc(CCCNC(=O)OCCNCCCCCC[C@H]2C[C@@]3(C)C(CC[C@@H]3O)C3CCC4=CC(=O)CCC4=C32)cc1]

or a pharmaceutically acceptable salt thereof, or a pharmaceutical composition of said compound.

5. The method of claim 4, wherein the polycystic liver disease is autosomal dominant polycystic liver disease.

6. The method of claim 4, wherein the polycystic liver disease is autosomal recessive polycystic liver disease.

* * * * *